United States Patent
Anderson et al.

(10) Patent No.: US 10,201,618 B2
(45) Date of Patent: Feb. 12, 2019

(54) ALKENYL SUBSTITUTED 2,5-PIPERAZINEDIONES, COMPOSITIONS, AND USES THEREOF

(71) Applicant: Massachusetts Institute of Technology, Cambridge, MA (US)

(72) Inventors: Daniel Griffith Anderson, Framingham, MA (US); Joseph R. Dorkin, Somerville, MA (US); Owen Shea Fenton, Somerville, MA (US); Kevin John Kauffman, Somerville, MA (US); Rebecca L. McClellan, Westwood, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/186,361

(22) Filed: Jun. 17, 2016

(65) Prior Publication Data

US 2016/0367686 A1    Dec. 22, 2016

Related U.S. Application Data

(60) Provisional application No. 62/182,264, filed on Jun. 19, 2015.

(51) Int. Cl.

| A61K 48/00 | (2006.01) |
|---|---|
| A61K 9/127 | (2006.01) |
| A61K 38/17 | (2006.01) |
| C07D 241/08 | (2006.01) |
| A61K 38/18 | (2006.01) |
| A61K 47/54 | (2017.01) |

(52) U.S. Cl.
CPC ...... *A61K 48/0033* (2013.01); *A61K 38/1816* (2013.01); *A61K 47/545* (2017.08); *C07D 241/08* (2013.01)

(58) Field of Classification Search
CPC .......... A61K 38/1816; A61K 47/48061; A61K 48/0033
USPC ........................................ 424/450; 514/44 R
See application file for complete search history.

(56) References Cited

U.S. PATENT DOCUMENTS

| 2,844,629 A | 7/1958 | William et al. |
| 4,022,833 A | 5/1977 | Diana et al. |
| 4,308,085 A | 12/1981 | Hoerhold et al. |
| 4,762,915 A | 8/1988 | Kung et al. |
| 4,873,370 A | 10/1989 | Chiu |
| 4,897,355 A | 1/1990 | Eppstein et al. |
| 4,946,857 A | 8/1990 | Kanehira et al. |
| 4,966,945 A | 10/1990 | Drawert et al. |
| 5,171,678 A | 12/1992 | Behr et al. |
| 5,334,761 A | 8/1994 | Gebeyehu et al. |
| 5,352,461 A | 10/1994 | Feldstein et al. |
| 5,386,028 A | 1/1995 | Tilstam et al. |
| 5,464,924 A | 11/1995 | Silvis et al. |
| 5,503,852 A | 4/1996 | Steiner et al. |
| 5,705,188 A | 1/1998 | Junichi et al. |
| 5,885,613 A | 3/1999 | Holland et al. |
| 5,976,569 A | 11/1999 | Milstein |
| 6,034,056 A | 3/2000 | Dutta |
| 6,071,497 A | 6/2000 | Steiner et al. |
| 6,331,318 B1 | 12/2001 | Milstein |
| 6,444,226 B1 | 9/2002 | Steiner et al. |
| 6,696,424 B1 | 2/2004 | Wheeler |
| 6,998,115 B2 | 2/2006 | Langer et al. |
| 7,427,394 B2 | 9/2008 | Anderson et al. |
| 7,507,859 B2 | 3/2009 | Grinstaff et al. |

(Continued)

FOREIGN PATENT DOCUMENTS

| CA | 2518132 A1 | 3/2006 |
| CA | 2 769 408 A1 | 2/2011 |
| CL | 201301810 A1 | 1/2014 |
| CL | 201400395 A1 | 12/2014 |
| CN | 101506196 A | 8/2009 |
| CN | 100 569 877 C | 12/2009 |
| CN | 101 863 544 B | 9/2011 |
| DE | 1155118 B | 10/1963 |
| DE | 25 20 814 A1 | 11/1976 |
| EP | 0 211 305 A2 | 2/1987 |
| EP | 0545305 A1 | 6/1993 |
| EP | 0673637 A1 | 9/1995 |

(Continued)

OTHER PUBLICATIONS

Invitation to Pay Additional Fees for PCT/US2016/038141, dated Sep. 20, 2016.

(Continued)

*Primary Examiner* — Janet L Epps-Smith
(74) *Attorney, Agent, or Firm* — Wolf, Greenfield & Sacks, P.C.

(57) ABSTRACT

Provided herein are compounds of Formula (I), and salts thereof, wherein each instance of $R^L$ is independently optionally substituted $C_6$-$C_{40}$ alkenyl. Further provided are compositions comprising a compound of Formula (I) and an agent. Further provided are methods and kits using the compositions for delivering an agent to a subject or cell and for treating and/or preventing a range of diseases. Further provided are methods of preparing compounds of Formula (I) and precursors thereof.

(I)

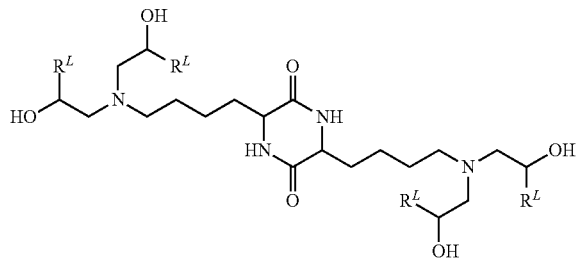

26 Claims, 7 Drawing Sheets

(56) References Cited

U.S. PATENT DOCUMENTS

| | | | |
|---|---|---|---|
| 8,071,082 B2 | 12/2011 | Zugates et al. | |
| RE43,612 E | 8/2012 | Anderson et al. | |
| 8,287,849 B2 | 10/2012 | Langer et al. | |
| 8,450,298 B2 | 5/2013 | Mahon et al. | |
| 8,557,231 B2 | 10/2013 | Langer et al. | |
| 8,562,966 B2 | 10/2013 | Zugates et al. | |
| 8,808,681 B2 | 8/2014 | Anderson et al. | |
| 8,969,353 B2 | 3/2015 | Mahon et al. | |
| 9,006,487 B2 | 4/2015 | Anderson et al. | |
| 9,101,666 B2 | 8/2015 | Langer et al. | |
| 9,193,827 B2 | 11/2015 | Ma et al. | |
| 9,227,197 B2 | 1/2016 | Anderson et al. | |
| 9,238,716 B2 | 1/2016 | Dahlman et al. | |
| 9,315,472 B2 | 4/2016 | Dong et al. | |
| 9,439,968 B2 | 9/2016 | Anderson et al. | |
| 9,512,073 B2 * | 12/2016 | Dong ................... | C12N 15/88 |
| 9,556,110 B2 | 1/2017 | Mahon et al. | |
| 9,629,804 B2 * | 4/2017 | Heartlein ............. | A61K 9/1272 |
| 9,700,627 B2 | 7/2017 | Langer et al. | |
| 2002/0131951 A1 | 9/2002 | Langer et al. | |
| 2003/0215395 A1 | 11/2003 | Yu et al. | |
| 2004/0071654 A1 | 4/2004 | Anderson et al. | |
| 2004/0181077 A1 | 9/2004 | Raymond et al. | |
| 2005/0123596 A1 | 6/2005 | Kohane et al. | |
| 2005/0143332 A1 | 6/2005 | Monahan et al. | |
| 2006/0223939 A1 | 10/2006 | Lange et al. | |
| 2007/0059373 A1 | 3/2007 | Oberg | |
| 2007/0185128 A1 | 8/2007 | Conde-Frieboes et al. | |
| 2007/0196503 A1 | 8/2007 | Wilson et al. | |
| 2007/0275923 A1 | 11/2007 | Chen et al. | |
| 2009/0221684 A1 | 9/2009 | Grinstaff et al. | |
| 2010/0178699 A1 | 7/2010 | Gao et al. | |
| 2010/0240072 A1 | 9/2010 | Wester et al. | |
| 2011/0009641 A1 | 1/2011 | Anderson et al. | |
| 2011/0158935 A1 | 6/2011 | Kraft | |
| 2011/0293703 A1 | 12/2011 | Mahon et al. | |
| 2012/0009222 A1 | 1/2012 | Nguyen et al. | |
| 2012/0065358 A1 | 3/2012 | Langer et al. | |
| 2012/0128760 A1 | 5/2012 | Manoharan et al. | |
| 2012/0196923 A1 | 8/2012 | Rege et al. | |
| 2012/0251560 A1 | 10/2012 | Dahlman et al. | |
| 2013/0158021 A1 | 6/2013 | Dong et al. | |
| 2013/0302401 A1 | 11/2013 | Ma et al. | |
| 2014/0094399 A1 | 4/2014 | Langer et al. | |
| 2014/0161830 A1 | 6/2014 | Anderson et al. | |
| 2014/0329884 A1 | 11/2014 | Dong et al. | |
| 2015/0140070 A1 | 5/2015 | Heartlein et al. | |
| 2015/0203439 A1 | 7/2015 | Mahon et al. | |
| 2016/0002178 A1 | 1/2016 | Fenton et al. | |
| 2016/0009657 A1 | 1/2016 | Anderson et al. | |
| 2016/0022821 A1 | 1/2016 | Langer et al. | |
| 2016/0114042 A1 | 4/2016 | Anderson et al. | |
| 2016/0137785 A1 | 5/2016 | Ma et al. | |
| 2016/0158363 A1 | 6/2016 | Alabi et al. | |
| 2016/0206740 A1 | 7/2016 | Dahlman et al. | |
| 2017/0165290 A1 | 6/2017 | Dong et al. | |
| 2017/0204075 A1 | 7/2017 | Mahon et al. | |
| 2018/0036333 A9 | 2/2018 | Dong et al. | |

FOREIGN PATENT DOCUMENTS

| | | |
|---|---|---|
| EP | 0 959 092 A1 | 11/1999 |
| EP | 1 277 829 A2 | 1/2003 |
| EP | 2 045 251 A1 | 4/2009 |
| EP | 2 532 649 A1 | 12/2012 |
| GB | 1602085 A | 11/1981 |
| JP | S49-127908 A | 12/1974 |
| JP | S51-023537 A | 2/1976 |
| JP | 51-125144 | 11/1976 |
| JP | H06-200073 A | 7/1994 |
| JP | H06-211978 A | 8/1994 |
| JP | H09-505593 A | 6/1997 |
| JP | H10-197978 A | 7/1998 |
| JP | 11-005786 A | 1/1999 |
| JP | 11-080142 A | 3/1999 |
| JP | 2000-501383 A | 2/2000 |
| JP | 2003-519199 A | 6/2003 |
| JP | 2006-515574 A | 6/2006 |
| JP | 2008-247749 A | 10/2008 |
| JP | 2009-544600 A | 12/2009 |
| JP | 2014172827 A | 9/2014 |
| JP | 5777846 B2 | 9/2015 |
| WO | WO 93/18754 A1 | 9/1993 |
| WO | WO 1995/14651 A1 | 6/1995 |
| WO | WO 95/18863 A1 | 7/1995 |
| WO | WO 96/25508 A1 | 8/1996 |
| WO | WO 1996/26179 A1 | 8/1996 |
| WO | WO 96/36314 A2 | 11/1996 |
| WO | WO 97/23457 A1 | 7/1997 |
| WO | WO 1998/16202 A2 | 4/1998 |
| WO | WO 2001/010845 A1 | 2/2001 |
| WO | WO 02/22709 A1 | 3/2002 |
| WO | WO 2002/031025 A2 | 4/2002 |
| WO | WO 2003/070735 A2 | 8/2003 |
| WO | WO 2004/048345 A2 | 6/2004 |
| WO | WO 2004/106411 A2 | 12/2004 |
| WO | WO 2005/055979 A2 | 6/2005 |
| WO | WO 2005/121348 A1 | 12/2005 |
| WO | WO 2006/065266 A2 | 6/2006 |
| WO | WO 2006/082088 A1 | 8/2006 |
| WO | WO 2006/105043 A2 | 10/2006 |
| WO | WO 2006/138380 A2 | 12/2006 |
| WO | WO 2007/096662 A2 | 8/2007 |
| WO | WO 2007/143659 A2 | 12/2007 |
| WO | WO 2008/011561 A2 | 1/2008 |
| WO | WO 2008/113364 A2 | 9/2008 |
| WO | WO 2009/046220 A2 | 4/2009 |
| WO | WO 2009/086547 A1 | 7/2009 |
| WO | WO 2010/042877 A1 | 4/2010 |
| WO | WO 2010/045512 A2 | 4/2010 |
| WO | WO 2010/053572 A2 | 5/2010 |
| WO | WO 2010/078373 A1 | 7/2010 |
| WO | WO 2010/099387 A1 | 9/2010 |
| WO | WO 2010/114789 A1 | 10/2010 |
| WO | WO 2010/129709 A1 | 11/2010 |
| WO | WO 2010/144789 A2 | 12/2010 |
| WO | WO 2011/012746 A2 | 2/2011 |
| WO | WO 2011/068810 A1 | 6/2011 |
| WO | WO 2012/027675 A2 | 3/2012 |
| WO | WO 2012/133737 A1 | 10/2012 |
| WO | WO 2012/135025 A2 | 10/2012 |
| WO | WO 2012/170889 A1 | 12/2012 |
| WO | WO 2012/170930 A1 | 12/2012 |
| WO | WO 2013/063468 A1 | 5/2013 |
| WO | WO-2013063468 A1 * | 5/2013 ............. C12N 15/88 |
| WO | WO 2014/028487 A1 | 2/2014 |
| WO | WO 2014/179562 A1 | 11/2014 |
| WO | WO 2014/210356 A1 | 12/2014 |
| WO | WO 2015/061467 A1 | 4/2015 |
| WO | WO-2015061467 A1 * | 4/2015 ......... A61K 48/0033 |

OTHER PUBLICATIONS

International Search Report and Written Opinion for PCT/US2016/038141, dated Nov. 22, 2016.

Fenton et al., Bioinspired Alkenyl Amino Alcohol Ionizable Lipid Materials for Highly Potent In Vivo mRNA Delivery. Adv Mater. Apr. 20, 2016;28(15):2939-43. doi: 10.1002/adma.201505822. Epub Feb. 18, 2016. With Supporting Information.

Winter et al., Transforming terpene-derived aldehydes into 1,2-epoxides via asymmetric α-chlorination: subsequent epoxide opening with carbon nucleophiles. Chem Commun (Camb). Nov. 28, 2011;47(44):12200-2. doi: 10.1039/c1cc15173h. Epub Oct. 10, 2011.

U.S. Appl. No. 13/662,002, filed Oct. 26, 2012, Dong et al.
U.S. Appl. No. 15/340,082, filed Nov. 1, 2016, Dong et al.
U.S. Appl. No. 11/453,222, filed Jul. 14, 2006, Anderson et al.
U.S. Appl. No. 14/643,845, filed Mar. 10, 2015, Anderson et al.
U.S. Appl. No. 10/446,444, filed May 28, 2003, Anderson et al.
U.S. Appl. No. 12/568,481, filed Sep. 28, 2009, Anderson et al.
U.S. Appl. No. 09/969,431, filed Oct. 2, 2001, Langer et al.
U.S. Appl. No. 11/099,886, filed Apr. 6, 2005, Langer et al.
U.S. Appl. No. 12/507,999, filed Jul. 23, 2009, Langer et al.

(56) References Cited

OTHER PUBLICATIONS

U.S. Appl. No. 13/301,315, filed Nov. 21, 2011, Langer et al.
U.S. Appl. No. 14/029,552, filed Sep. 17, 2013, Langer et al.
U.S. Appl. No. 14/811,613, filed Jul. 28, 2015, Langer et al.
U.S. Appl. No. 11/780,754, filed Jul. 20, 2007, Zugates et al.
U.S. Appl. No. 13/312,224, filed Dec. 6, 2011, Zugates et al.
U.S. Appl. No. 14/051,313, filed Oct. 10, 2013, Zugates et al.
U.S. Appl. No. 11/758,078, filed Jun. 5, 2007, Anderson et al.
U.S. Appl. No. 12/613,968, filed Nov. 6, 2009, Mahon et al.
U.S. Appl. No. 12/716,732, filed Mar. 3, 2010, Mahon et al.
U.S. Appl. No. 13/128,020, filed Aug. 16, 2011, Mahon et al.
U.S. Appl. No. 14/599,004, filed Jan. 16, 2015, Mahon et al.
U.S. Appl. No. 15/417,530, filed Jan. 27, 2017, Mahon et al.
U.S. Appl. No. 13/126,260, filed Apr. 27, 2011, Nguyen et al.
U.S. Appl. No. 13/819,280, filed Feb. 26, 2013, Ma et al.
U.S. Appl. No. 14/941,384, filed Nov. 13, 2015, Ma et al.
U.S. Appl. No. 13/428,695, filed Mar. 23, 2012, Dahlman et al.
U.S. Appl. No. 14/995,842, filed Jan. 14, 2016, Dahlman et al.
U.S. Appl. No. 14/089,603, filed Aug. 13, 2013, Anderson et al.
U.S. Appl. No. 14/089,603, filed Nov. 25, 2015, Anderson et al.
U.S. Appl. No. 14/987,717, filed Jan. 4, 2016, Anderson et al.
U.S. Appl. No. 15/264,315, filed Sep. 13, 2016, Anderson et al.
U.S. Appl. No. 14/267,530, filed May 1, 2014, Dong et al.
U.S. Appl. No. 14/900,869, filed Dec. 22, 2015, Alibi et al.
U.S. Appl. No. 14/789,227, filed Jul. 1, 2015, Fenton et al.
PCT/US2001/031270, Jan. 2, 2003, Written Opinion.
PCT/US2001/031270, Aug. 19, 2003, International Preliminary Examination Report.
EP 07813156.2, Oct. 5, 2009, Extended European Search Report.
PCT/US2007/073976, Sep. 29, 2008, International Search Report and Written Opinion.
PCT/US2007/073976, Feb. 5, 2009, International Preliminary Report on Patentability.
EP 07798132.2, Jul. 18, 2011, Extended European Search Report.
PCT/US2007/070430, Dec. 13, 2007, International Search Report and Written Opinion.
PCT/US2007/070430, Dec. 24, 2008, International Preliminary Report on Patentability.
EP 09825132.5, Jul. 16, 2013, Extended European Search Report.
PCT/US2009/006018, May 25, 2010, International Search Report and Written Opinion.
PCT/US2009/006018, May 19, 2011, International Preliminary Report on Patentability.
EP11820727.3, Nov. 26, 2014, Partial European Search Report.
EP 11820727.3, Apr. 25, 2015, Extended European Search Report.
PCT/US2011/049360, Mar. 20, 2012, International Search Report and Written Opinion.
PCT/US2011/049360, Mar. 7, 2013, International Preliminary Report on Patentability.
PCT/US2012/030349, Jul. 24, 2012, Invitation to Pay Additional Fees.
PCT/US2012/030349, Oct. 5, 2012, International Search Report and Written Opinion.
PCT/US2012/030349, Oct. 10, 2013, International Preliminary Report on Patentability.
PCT/US2013/054726, Oct. 31, 2013, Invitation to Pay Additional Fees.
PCT/US2013/054726, Jan. 7, 2014, International Search Report and Written Opinion.
PCT/US2013/054726, Feb. 26, 2015, International Preliminary Report on Patentability.
PCT/US2014/036355, Aug. 5, 2014, International Search Report and Written Opinion.
PCT/US2014/044408, Oct. 24, 2014, International Search Report and Written Opinion.
Invitation to Pay Additional Fees for PCT/US2012/062222, dated Dec. 14, 2012.
International Search Report and Written Opinion for PCT/US2012/062222, dated Mar. 27, 2013.
International Preliminary Report on Patentability for PCT/US2012/062222, dated May 8, 2014.
Extended European Search Report for EP 06784878.8, dated Jun. 29, 2009.
Extended European Search Report for EP 11186795.8, dated Jun. 19, 2012.
International Search Report and Written Opinion for PCT/US2006/023171, dated May 29, 2008.
International Preliminary Report on Patentability for PCT/US2006/023171, dated Jul. 3, 2008.
Extended European Search Report, dated Jan. 28, 2008, for EP 07013193.3.
Invitation to Pay Additional Fees for PCT/US2004/016521, dated Sep. 29, 2004.
International Search Report and Written Opinion for PCT/US2004/016521, dated Dec. 8, 2004.
International Preliminary Report on Patentability for PCT/US2004/016521, dated Dec. 15, 2005.
International Search Report for PCT/US2001/031270, dated May 22, 2002.
Written Opinion for PCT/US2001/031270, dated Jan. 2, 2003.
International Preliminary Examination Report for PCT/US2001/031270, dated Aug. 19, 2003.
Extended European Search Report, dated Oct. 5, 2009, for EP 07813156.2.
International Search Report and Written Opinion for PCT/US2007/073976, dated Sep. 29, 2008.
International Preliminary Report on Patentability for PCT/US2007/073976, dated Feb. 5, 2009.
Extended European Search Report for EP 07798132.2, dated Jul. 18, 2011.
International Search Report and Written Opinion for PCT/US2007/070430, dated Dec. 13, 2007.
International Preliminary Report on Patentability for PCT/US2007/070430, dated Dec. 24, 2008.
Extended European Search Report for European Application No. 09825132.5, dated Jul. 16, 2013.
International Search Report and Written Opinion for PCT/US2009/006018, dated May 25, 2010.
International Preliminary Report on Patentability for PCT/US2009/006018, dated May 19, 2011.
Extended European Search Report for European Application No. 11820727.3, dated Apr. 22, 2015.
Partial European Search Report for European Application No. 11820727.3, dated Nov. 26, 2014.
International Search Report and Written Opinion for PCT/US2011/049360, dated Mar. 20, 2012.
International Preliminary Report on Patentability for PCT/US2011/049360, dated Mar. 7, 2013.
Invitation to Pay Additional Fees for PCT/US2012/030349, dated Jul. 24, 2012.
International Search Report and Written Opinion for PCT/US2012/030349, dated Oct. 5, 2012.
International Preliminary Report on Patentability for PCT/US2012/030349, dated Oct. 10, 2013.
Invitation to Pay Additional Fees for PCT/US2013/054726, dated Oct. 31, 2013.
International Search Report and Written Opinion for PCT/US2013/054726, dated Jan. 7, 2014.
International Preliminary Report on Patentability for PCT/US2013/054726, dated Feb. 26, 2015.
International Search Report and Written Opinion for PCT/US2014/036355, dated Aug. 5, 2014.
International Search Report and Written Opinion for PCT/US2014/044408, dated Oct. 24, 2014.
Adami et al., An amino acid-based amphoteric liposomal delivery system for systemic administration of siRNA. Mol Ther. Jun. 2011;19(6):1141-51. doi: 10.1038/mt.2011.56. Epub Apr. 19, 2011.
Akinc et al., A combinatorial library of lipid-like materials for delivery of RNAi therapeutics. Nat Biotech. 2008;26(5):561-69.
Akinc et al., Development of lipidoid-siRNA formulations for systemic delivery to the liver. Mol Ther. May 2009;17(5):872-9. doi: 10.1038/mt.2009.36. Epub Mar. 3, 2009.

(56) References Cited

OTHER PUBLICATIONS

Akinc et al., Parallel synthesis and biophysical characterization of a degradable polymer library for gene delivery. J Am Chem Soc. May 7, 2003;125(18):5316-23.
Akinc et al., Targeted delivery of RNAi therapeutics with endogenous and exogenous ligand-based mechanisms. Mol Ther. Jul. 2010;18(7):1357-64. doi: 10.1038/mt.2010.85. Epub May 11, 2010.
Allen et al., Liposomal drug delivery systems: from concept to clinical applications. Adv Drug Deliv Rev. Jan. 2013;65(1):36-48. doi: 10.1016/j.addr.2012.09.037. Epub Oct. 1, 2012.
Amirouche et al., Activation of p38 signaling increases utrophin A expression in skeletal muscle via the RNA-binding protein KSRP and inhibition of AU-rich element-mediated mRNA decay: implications for novel DMD therapeutics. Hum Mol Genet. Aug. 1, 2013;22(15):3093-111. doi: 10.1093/hmg/ddt165. Epub Apr. 10, 2013.
Anderson et al., Structure/property studies of polymeric gene delivery using a library of poly(beta-amino esters). Mol Ther. Mar. 2005;11(3):426-34.
Asokan et al., Cytosolic delivery of macromolecules. 3. Synthesis and characterization of acid-sensitive bis-detergents. Bioconjug Chem. Nov.-Dec. 2004;15(6):1166-73.
Behr et al., Efficient gene transfer into mammalian primary endocrine cells with lipopolyamine-coated DNA. Proc Natl Acad Sci U S A. Sep. 1989;86(18):6982-6.
Bourque et al., Hydroformylation Reactions Using Recyclable Rhodium-Complexed Dendrimers on Silica. J Am Chem Soc. 2000;122(5):956-957.
Braun et al., Structure/function relationships of polyamidoamine/DNA dendrimers as gene delivery vehicles. J Pharm Sci. Feb. 2005;94(2):423-36.
Brey et al., Controlling poly(beta-amino ester) network properties through macromer branching. Acta Biomater. Mar. 2008;4(2):207-17. Epub Oct. 22, 2007.
Brey et al., Influence of macromer molecular weight and chemistry on poly(beta-amino ester) network properties and initial cell interactions. J Biomed Mater Res A. Jun. 1, 2008;85(3):731-41.
Burnett et al., Current progress of siRNA/shRNA therapeutics in clinical trials. Biotechnol J. Sep. 2011;6(9):1130-46. doi: 10.1002/biot.201100054. Epub Jul. 11, 2011.
Byk et al., Synthesis, activity, and structure—activity relationship studies of novel cationic lipids for DNA transfer. J Med Chem. 1998;41(2):224-235.
Castanotto et al., The promises and pitfalls of RNA-interference-based therapeutics. Nature. Jan. 22, 2009;457(7228):426-33. doi: 10.1038/nature07758.
Cazzola et al., Use of recombinant human erythropoietin outside the setting of uremia. Blood. Jun. 15, 1997;89(12):4248-67.
Chen et al., Rapid discovery of potent siRNA-containing lipid nanoparticles enabled by controlled microfluidic formulation. J Am Chem Soc. Apr. 25, 2012;134(16):6948-51. doi: 10.1021/ja301621z. Epub Apr. 10, 2012.
Chen et al., Tumor-targeted delivery of siRNA by non-viral vector: safe and effective cancer therapy. Expert Opin Drug Deliv. Dec. 2008;5(12):1301-11. doi: 10.1517/17425240802568505.
Chiang et al., Synthesis, characterization and properties of novel self-extinguishing organic-inorganic nanocomposites containing nitrogen, silicon and phosphorus via sol-gel method. Composite Science and Technology. 2008;68(14):2849-57.
Damen et al., Delivery of DNA and siRNA by novel gemini-like amphiphilic peptides. J Control Release. Jul. 1, 2010;145(1):33-9. doi: 10.1016/j.jconrel.2010.03.028. Epub Apr. 8, 2010.
Davis et al., The first targeted delivery of siRNA in humans via a self-assembling, cyclodextrin polymer-based nanoparticle: from concept to clinic. Mol Pharm. May-Jun. 2009;6(3):659-68. doi: 10.1021/mp900015y.
Dong et al., Lipopeptide nanoparticles for potent and selective siRNA delivery in rodents and nonhuman primates. Proc Natl Acad Sci U S A. Mar. 18, 2014;111(11):3955-60. doi: 10.1073/pnas.1322937111. Epub Feb. 10, 2014.

Felgner et al., Lipofection: a highly efficient, lipid-mediated DNA-transfection procedure. Proc Natl Acad Sci U S A. Nov. 1987;84(21):7413-7.
Fenske et al., Liposomal nanomedicines. Expert Opin Drug Deliv. Jan. 2008;5(1):25-44.
Ferruti et al., A novel modification of poly(l-lysine) leading to a soluble cationic polymer with reduced toxicity and with potential as a transfection agent. Macromol Chem Phys 1998;199:2565-75.
Ferruti et al., Linear amino polymers: Synthesis, protonation and complex formation. Advances in Polymer Science. 1984;58:55-92.
Fourneau et al., Two new series of local anesthetics derived from piperazine. Bulletin de la Societe Chimique de France. 1930;47:1003-16. French.
Giulianai et al., Beyond natural antimicrobial peptides: multimeric peptides and other peptidomimetic approaches. Cell Mol Life Sci. Jul. 2011;68(13):2255-66. doi: 10.1007/s00018-011-0717-3. Epub May 20, 2011.
Gonzalez et al., New class of polymers for the delivery of macromolecular therapeutics. Bioconjug Chem. Nov.-Dec. 1999;10(6):1068-74.
Gupta et al., A review of in vitro-in vivo investigations on dendrimers: the novel nanoscopic drug carriers. Nanomedicine. Jun. 2006;2(2):66-73.
Heyes et al., Cationic lipid saturation influences intracellular delivery of encapsulated nucleic acids. J Control Release. Oct. 3, 2005;107(2):276-87.
Hill et al., In vitro cytotoxicity of poly(amidoamine)s: relevance to DNA delivery. Biochim Biophys Acta. Apr. 19, 1999;1427(2):161-74.
Hofland et al., Formation of stable cationic lipid/DNA complexes for gene transfer. Proc Natl Acad Sci USA. Jul. 9, 1996;93(14):7305-9.
Hsu et al., Diethanolamine (DEA) degradation under gas-treating conditions. Industrial and Engineering Chemistry Product Research and Development. 1985;24(4):630-35.
Ichimaru et al., Synthesis and characterization of new piperazine-type inhibitors for mitochondrial NADH-ubiquinone oxidoreductase (complex I). Biochemistry. Oct. 7, 2008;47(40):10816-26.
Ikeda et al., Role of micafungin in the antifungal armamentarium. Curr Med Chem. 2007;14(11):1263-75.
Incani et al., Lipid and hydrophobic modification of cationic carriers on route to superior gene vectors. Soft Matter. 2010; 6(10):2124-38.
Jolck et al, Solid-phase synthesis of PEGylated lipopeptides using click chemistry. Bioconjug Chem. May 19, 2010;21(5):807-10.
Jon et al., Degradable poly(amino alcohol esters) as potential DNA vectors with low cytotoxicity. Biomacromolecules. Nov.-Dec. 2003;4(6):1759-62.
Juliano et al., Biological barriers to therapy with antisense and siRNA oligonucleotides. Mol Pharm. May-Jun. 2009;6(3):686-95. doi: 10.1021/mp900093r.
Kanasty et al., Delivery materials for siRNA therapeutics. Nat Mater. Nov. 2013;12(11):967-77. doi: 10.1038/nmat3765.
Kanetani et al., Synthesis, and physicochemical and antimicrobial properties of 3-(3-alkyl-1-piperazinyl)-1-propanesulfonic acids and some related compounds. Nippon Kagaku Kaishi. 1983(12):1783-91.
Kariko et al., Increased erythropoiesis in mice injected with submicrogram quantities of pseudouridine-containing mRNA encoding erythropoietin. Mol Ther. May 2012;20(5):948-53. doi: 10.1038/mt.2012.7. Epub Feb. 14, 2012.
Kaur et al., A delineation of diketopiperazine self-assembly processes: understanding the molecular events involved in Nepsilon-(fumaroyl)diketopiperazine of L-Lys (FDKP) interactions. Mol Pharm. Mar.-Apr. 2008;5(2):294-315.
Kim et al., Synthesis of biodegradable cross-linked poly(beta-amino ester) for gene delivery and its modification, inducing enhanced transfection efficiency and stepwise degradation. Bioconjug Chem. Sep.-Oct. 2005;16(5):1140-8.
Klibanov et al., Amphipathic polyethyleneglycols effectively prolong the circulation time of liposomes. FEBS Lett. Jul. 30, 1990;268(1):235-7.

(56) References Cited

OTHER PUBLICATIONS

Kormann et al., Expression of therapeutic proteins after delivery of chemically modified mRNA in mice. Nat Biotechnol. Feb. 2011;29(2):154-7. doi: 10.1038/nbt.1733. Epub Jan. 9, 2011.
Leuschner et al., Therapeutic siRNA silencing in inflammatory monocytes in mice. Nat Biotechnol. Oct. 9, 2011;29(11):1005-10. doi: 10.1038/nbt.1989.
Liu et al., Efficacy of erythropoietin combined with enteral nutrition for the treatment of anemia in Crohn's disease: a prospective cohort study. Nutr Clin Pract. Feb. 2013;28(1):120-7. doi: 10.1177/0884533612462744. Epub Oct. 12, 2012.
Love et al., Lipid-like materials for low-dose, in vivo gene silencing. Proc Natl Acad Sci U S A. Feb. 2, 2010;107(5):1864-9. doi: 10.1073/pnas.0910603106. Epub Jan. 11, 2010.
Lukyanov et al., Micelles from lipid derivatives of water-soluble polymers as delivery systems for poorly soluble drugs. Adv Drug Deliv Rev. May 7, 2004;56(9):1273-89.
Lynn et al., Accelerated discovery of synthetic transfection vectors: parallel synthesis and screening of a degradable polymer library. J Am Chem Soc. Aug. 22, 2001;123(33):8155-6.
Lynn et al., Degradable Poly(β-amino esters): Synthesis, Characterization, and Self-Assembly with Plasmid DNA. J. Am. Chem. Soc. 2000;122 (44): 10761-8.
Lynn et al., pH-Responsive Polymer Microspheres: Rapid Release of Encapsulated Material within the Range of Intracellular pH. Angew Chem Int Ed Engl. May 4, 2001;40(9):1707-10.
Ma et al., Developlment of Cationic Polymer Coatings to Regulate Foreign Body Responses. Adv Mater. 2011;23:H189-94.
Margus et al., Cell-penetrating peptides as versatile vehicles for oligonucleotide delivery. Mol Ther. Mar. 2012;20(3):525-33. doi: 10.1038/mt.2011.284. Epub Jan. 10, 2012.
McClellan et al., Genetic Heterogeneity in Human Disease. Cell. Apr. 2010;141(2):210-7.
McClellan et al., Response: Why It Is Time to Sequence. Cell. Aug. 2010;142(3):353-55.
Mintzer et al., Nonviral vectors for gene delivery. Chem Rev. Feb. 2009;109(2):259-302.
Morrissey et al., Potent and persistent in vivo anti-HBV activity of chemically modified siRNAs. Nat Biotechnol. Aug. 2005;23(8):1002-7. Epub Jul. 24, 2005.
Moure et al. Chemical modulation of peptoids: synthesis and conformational studies on partially constrained derivatives. Chemistry. Jul. 4, 2011;17(28):7927-39. doi: 10.1002/chem.201100216. Epub May 24, 2011.
Narang et al., Cationic lipids with increased DNA binding affinity for nonviral gene transfer in dividing and nondividing cells. Bioconjug Chem. Jan.-Feb. 2005;16(1):156-68.
Parrish et al., Five- and six-membered ring opening of pyroglutamic diketopiperazine. J Org Chem. Mar. 22, 2002;67(6):1820-6.
Peer et al., Nanocarriers as an emerging platform for cancer therapy. Nat Nanotechnol. Dec. 2007;2(12):751-60. doi: 10.1038/nnano.2007.387.
Prata et al., Lipophilic peptides for gene delivery. Bioconjug Chem. Feb. 2008;19(2):418-20. doi: 10.1021/bc700451b. Epub Jan. 11, 2008.
Reichmutch et al., mRNA vaccine delivery using lipid nanoparticles. Ther Deliv. 2016;7(5):319-34. doi: 10.4155/tde-2016-0006.
Rogers et al., Synthetic Experiments in the Ferrichrome Series. Biochemistry. Dec. 1964;3:1850-5.
Sahin et al., mRNA-based therapeutics—developing a new class of drugs. Nat Rev Drug Discov. Oct. 2014;13(10):759-80. doi: 10.1038/nrd4278. Epub Sep. 19, 2014.
Scheel et al., Therapeutic anti-tumor immunity triggered by injections of immunostimulating single-stranded RNA. Eur J Immunol. Oct. 2006;36(10):2807-16.
Semple et al., Rational design of cationic lipids for siRNA delivery. Nat Biotechnol. Feb. 2010;28(2):172-6. doi: 10.1038/nbt.1602. Epub Jan. 17, 2010.
Sen et al., Surfactin: biosynthesis, genetics and potential applications. Adv Exp Med Biol. 2010;672:316-23.
Shchori, Poly(secondary Amine)s from Diacrylates and Diamines. J Polym Sci Polymer. Jun. 1983;21(6):413-15.
Siegwart et al., Combinatorial synthesis of chemically diverse core-shell nanoparlicles for intracellular delivery. Proc Natl Acad Sci U S A. Aug. 9, 2011;108(32):12996-3001. doi: 10.1073/pnas.1106379108. Epub Jul. 22, 2011.
STN-CAS database Registry No. 103745-33-1. Entered STN-CAS database on Aug. 18, 1986.
STN-CAS database Registry No. 1067642-37-8. Entered STN-CAS database on Oct. 29, 2008.
STN-CAS database Registry No. 1100276-71-8. Entered STN-CAS database on Feb. 3, 2009.
STN-CAS database Registry No. 128351-30-4. Entered STN-CAS database on Jul. 20, 1990.
STN-CAS database Registry No. 129257-51-8. Entered STN-CAS database on Sep. 7, 1990.
STN-CAS database Registry No. 129257-52-9. Entered STN-CAS database on Sep. 7, 1990.
STN-CAS database Registry No. 21282-28-0. Entered STN-CAS database on Nov. 16, 1984.
STN-CAS database Registry No. 28549-91-9. Entered STN-CAS database on Nov. 16, 1984.
STN-CAS database Registry No. 3768-41-0. Entered STN-CAS database on Nov. 16, 1984.
STN-CAS database Registry No. 53731-96-7. Entered STN-CAS database on Nov. 16, 1984.
STN-CAS database Registry No. 53731-98-9. Entered STN-CAS database on Nov. 16, 1984.
STN-CAS database Registry No. 54736-47-9. Entered STN-CAS database on Nov. 16, 1984.
STN-CAS database Registry No. 57018-25-4. Entered STN-CAS database on Nov. 16, 1984.
STN-CAS database Registry No. 57273-30-0. Entered STN-CAS database on Nov. 16, 1984.
STN-CAS database Registry No. 6302-30-3. Entered STN-CAS database on Nov. 16, 1984.
STN-CAS database Registry No. 635749-38-1. Entered STN-CAS database on Jan. 9, 2004.
STN-CAS database Registry No. 68310-64-5. Entered STN-CAS database on Nov. 16, 1984.
STN-CAS database Registry No. 785789-76-6. Entered STN-CAS database on Nov. 22, 2004.
STN-CAS database Registry No. 883453-96-1. Entered STN-CAS database on May 9, 2006.
STN-CAS database Registry No. 89038-30-2. Entered STN-CAS database on Nov. 16, 1984.
STN-CAS database Registry No. 956464-55-4. Entered STN-CAS database on Dec. 3, 2007.
STN-CAS database Registry No. 956465-28-4. Entered STN-CAS database on Dec. 3, 2007.
Swali et al., Solid-Phase Dendrimer Synthesis and the Generation of Super-High-Loading Resin Beads for Combinatorial Chemistry. J Org Chem Am Chem Soc. 1997;62:4902-03.
Tan et al., Engineering Nanocarriers for siRNA Delivery. Small. Apr. 4, 2011;7(7):841-56. doi: 10.1002/smll.201001389. Epub Feb. 25, 2011.
Thiel et al., Therapeutic applications of DNA and RNA aptamers. Oligonucleotides. Sep. 2009;19(3):209-22. doi: 10.1089/oli.2009.0199.
Tranchant et al., Physicochemical optimisation of plasmid delivery by cationic lipids. J Gene Med. Feb. 2004;6 Suppl 1:S24-35.
Tsvetkov et al., [Neoglycoconjugates based on dendrimeric poly(aminoamides)]. Bioorg Khim. Nov.-Dec. 2002;28(6):518-34. Russian. Published in English in Russian Journal of Bioorganic Chemistry, 2002:28(6):470-86.
Van Balen et al., Liposome/water lipophilicity: methods, information content, and pharmaceutical applications. Med Res Rev. May 2004;24(3):299-324.
Van De Wetering et al., Structure-activity relationships of water-soluble cationic methacrylate/methacrylamide polymers for nonviral gene delivery. Bioconjug Chem. Jul.-Aug. 1999;10(4):589-97.

(56) References Cited

OTHER PUBLICATIONS

Vandenbroucke et al., Prolonged gene silencing in hepatoma cells and primary hepatocytes after small interfering RNA delivery with biodegradable poly(beta-amino esters). J Gene Med. Jul. 2008;10(7):783-94.

Weinstein et al., RNAi nanomedicines: challenges and opportunities within the immune system. Nanotechnology. Jun. 11, 2010;21(23):232001. doi: 10.1088/0957-4484/21/23/232001. Epub May 13, 2010.

Whitehead et al., Degradable lipid nanoparticles with predictable in vivo siRNA delivery activity. Nat Commun. Jun. 27, 2014;5:4277. doi: 10.1038/ncomms5277.

Whitehead et al., Knocking down barriers: advances in siRNA delivery. Nat Rev Drug Discov. Feb. 2009;8(2):129-38.

Wu et al., Cationic lipid polymerization as a novel approach for constructing new DNA delivery agents. Bioconjug Chem. Mar.-Apr. 2001;12(2):251-7.

Zagridullin et al., Monobasic amines. II. Cycloalkylation and hydroxyalkylation of cyclic and acyclic di- and polyamines.. Zhurnal Organicheskoi Khimii. 1990;26(1):184-88. Russian.

Zamora et al., RNA interference therapy in lung transplant patients infected with respiratory syncytial virus. Am J Respir Crit Care Med. Feb. 15, 2011;183(4):531-8. doi: 10.1164/rccm.201003-0422OC. Epub Sep. 17, 2010.

Zaugg et al., 3-Carboxy-2,5-piperazinedione and Derivatives. J Amer Chem Soc. Jun. 5, 1956;78(11):2626-2631.

International Preliminary Report on Patentability for PCT/US2016/038141, dated Dec. 28, 2017.

Griffiths et al., The Structure of Metallomicelles. Chem. Eur. J., 2004;10:2022-8. doi:10.1002/chem.200305670.

Griffiths et al.., Structure—property relationships in metallosurfactants. Soft Matter, 2010;6:1981-9. doi: 10.1039/B920143B.

Kusumoto et al., Gene transfer effects on various cationic amphiphiles in CHO cells. Cytotechnology. Jun. 2006;51(2):57-66. doi: 10.1007/s10616-006-9014-7. Epub Sep. 7, 2006.

Li et al., [Analysis of HLA matching probability in Guangzhou Cord Blood Bank]. Zhongguo Shi Yan Xue Ye Xue Za Zhi. Aug. 2003;11(4):424-8. Abstract Only.

Ramakrishna et al., Synthesis of RGD peptidomimetic analogues of 2,5-diketopiperazine. Indian Journal of Chemistry Dec. 1999;38B:1331-7.

Shen et al., Synthesis of Novel Amphiphilic Poly (ester-amine) Dendrimers and Their Recognition of Hg2+ at the Air/Water Interface. Chin. J. Chem. Oct. 2003;21(8):1011-14.

Valente et al., External Coordination of Europium(III) Prior to Its Encapsulation within a Cyclen-Based Pendant Donor Macrocycle. Inorg. Chem., 1998;37(12):2846-7. DOI: 10.1021/ic980012+.

Whitbread et al., Diastereomeric Δ-1,4,7,10-Tetrakis((R)-2-hydroxy-2-phenylethyl)-1,4,7,10-tetraazacyclododecane and Its Alkali Metal Complex Ions. A Potentiometric Titration, Nuclear Magnetic Resonance, and Molecular Orbital Study. J. Am. Chem. Soc. 1998;120:2862-9.

U.S. Appl. No. 12/833,749, filed Jul. 8, 2010, Anderson et al.

U.S. Appl. No. 15/647,116, filed Jul. 11, 2017, Langer et al.

PCT/US2016/038141, Dec. 28, 2017, International Preliminary Report on Patentability.

* cited by examiner

ALKENYL SUBSTITUTED 2,5-PIPERAZINEDIONES, COMPOSITIONS, AND USES THEREOF

RELATED APPLICATIONS

The present application claims priority under 35 U.S.C. § 119(e) to U.S. provisional patent application, U.S. Ser. No. 62/182,264, filed Jun. 19, 2015, the entire contents of which is incorporated herein by reference.

GOVERNMENT SUPPORT

This invention was made with Government support under grant no. R01-DE016516 awarded by the National Institutes of Health. The Government has certain rights in the invention.

BACKGROUND OF THE INVENTION

The ability to silence genes via RNA interference (RNAi) was reported by Mello and Fire in 1998. See Fire et al., *Nature* (1998) 391:806-811. Since then, scientists have rushed to take advantage of the enormous therapeutic potential driven by targeted gene knockdown. This is evidenced by the fact that the first report of small interfering RNA (siRNA) mediated RNAi in human beings was reported only twelve years after the phenomenon was described in *Caenorhabditis elegans*. See Davis et al., *Nature* (2010) 464: 1067-1070. The advantages of siRNA therapeutics include high target selectivity and specificity, and the potential to target pathways currently believed to be "undruggable" for the treatment of genetic diseases without effective therapy. siRNA therapeutics has shown promising results for the treatment of various diseases, such as hepatic carcinoma, hypercholesterolemia, refractory anemia, or familial amyloid neuropathy.

However, the efficient delivery of siRNA is still a challenge in the development of siRNA therapeutics. Due to issues associated with delivery efficiency and toxicity, the clinical use of siRNA requires safer and more effective delivery systems. It is understood that the development of genetic drugs is slowed by the inability to deliver nucleic acids effectively in vivo. When unprotected, genetic materials injected into the bloodstream can be degraded by deoxyribonucleases (DNAases) and ribonucleases (RNAases), or, if not degraded, the genetic materials can stimulate an immune response. See, e.g., Whitehead et al., *Nature Reviews Drug Discovery* (2009) 8:129-138; Robbins et al., *Oligonucleotides* (2009) 19:89-102. Intact siRNA must then enter the cytosol, where the antisense strand is incorporated into the RNA-induced silencing complex (RISC) (Whitehead et al., supra). The RISC associates with and degrades complementary mRNA sequences, thereby preventing translation of the target mRNA into protein, i.e., "silencing" the gene.

To overcome difficulties in delivery, polynucleotides have been complexed with a wide variety of delivery systems, including polymers, lipids, inorganic nanoparticles, and viruses. See, e.g., Peer et al. *Nature Nanotechnology*, (2007) 2:751-760. However, despite promising data from ongoing clinical trials for the treatment of respiratory syncytial virus and liver cancers (see, e.g., Zamora et al., *Am. J. Respir. Crit. Care Med.* (2011) 183:531-538), the clinical use of siRNA continues to require development of safer and more effective delivery systems. Toward this end, numerous lipid-like molecules have been developed including poly β-amino esters and amino alcohol lipids. See, e.g., International PCT Patent Application Publications, WO 2002/031025, WO 2004/106411, WO 2008/011561, WO 2007/143659, WO 2006/138380, and WO 2010/053572. Amino acid, peptide, polypeptide-lipids have also been studied for a variety of applications, including use as therapeutics, biosurfactants, and nucleotide delivery systems. See, e.g., Giuliani et al., *Cellular and Molecular Life Sciences* (2011) 68:2255-2266; Ikeda et al., *Current Medicinal Chemistry* (2007) 14: 111263-1275; Sen, *Advances in Experimental Medicine and Biology* (2010) 672:316-323; Damen et al., *Journal of Controlled Release* (2010) 145:33-39, WO 2013/063468; WO 2014/179562, and U.S. Publication No. 2015/0140070. Furthermore, Amino acid-lipids have been found useful as delivery vehicles for messenger RNA (mRNA) therapy, which is an increasingly important option for treatment of various diseases, in particular, for those associated with deficiency of one or more proteins. See, e.g., U.S. Publication No. 2015/0140070.

However, there continues to remain a need to investigate and develop new and improved polynucleotide delivery systems, such as ones that are more efficient and/or less toxic than existing systems.

SUMMARY OF THE INVENTION

Described herein are novel alkenyl substituted 2,5-piperazinediones of Formula (I):

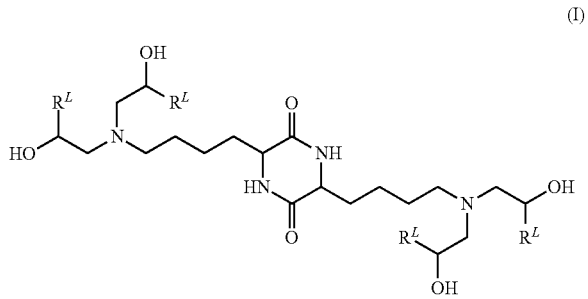

and salts thereof, wherein each instance of $R^L$ is independently optionally substituted $C_6$-$C_{40}$ alkenyl. Such compounds are considered useful for a variety of applications, such as, for example, improved nucleotide delivery.

Further provided are compositions (e.g., pharmaceutical compositions) comprising a compound of Formula (I), an agent (e.g., a pharmaceutical agent, a diagnostic agent, and/or polynucleotide, such as an siRNA, mRNA, or plasmid DNA), and optionally an excipient (e.g., a pharmaceutically acceptable excipient). Further still provided are methods and kits using the compositions for delivering an agent to a subject (e.g., to the liver, lung, and/or spleen of the subject) or cell and for treating and/or preventing a range of diseases, such as a genetic disease, proliferative disease, hematological disease, neurological disease, liver disease, spleen disease, lung disease, painful condition, psychiatric disorder, musculoskeletal disease, a metabolic disorder, inflammatory disease, or autoimmune disease.

Without wishing to be bound by any particular theory, the compositions as described herein are, in certain embodiments, thought to be useful for delivering the agent to a subject (e.g., to the liver, lung, and/or spleen of the subject) or cell. Furthermore, without wishing to be bound by any particular theory, a compound of Formula (I), which includes more than one amino moiety that may be protonated to form positively charged ammonium cations, may non-covalently bind to an agent that includes negatively charged moieties, such as a polynucleotide, to form a complex. Moreover, without wishing to be bound by any particular theory, a compound of Formula (I) includes four $R^L$ alkenyl moieties which may assist the compound of Formula (I) and/or the complex of the compound of Formula (I) and the agent to pass through cell membranes or be taken up by cells.

Thus, in one aspect, provided are methods of use of a compound of Formula (I) or salt thereof, or composition (e.g., a pharmaceutical composition) comprising a compound of Formula (I), or salt thereof and an agent, for the treatment or prevention of a disease in a subject in need thereof. In certain embodiments, the agent is a polynucleotide. In certain embodiments, the methods of treating a disease comprise administering to the subject a therapeutically effective amount of a pharmaceutical composition described herein that includes a pharmaceutical agent. In certain embodiments, the methods of preventing a disease comprise administering to the subject a prophylcatically effective amount of a pharmaceutical composition described herein that includes a pharmaceutical agent. In certain embodiments, the disease that is treated or prevented by a described method is a genetic disease, proliferative disease, hematological disease, neurological disease, liver disease, spleen disease, lung disease, painful condition, psychiatric disorder, genitourinary disease, musculoskeletal disease, a metabolic disorder, inflammatory disease, or autoimmune disease. In certain embodiments, the disease is a hematological disease, e.g., anemia. In certain embodiments, the disease is hepatic carcinoma, hypercholesterolemia, refractory anemia, familial amyloid neuropathy, or hemophilia. In certain embodiments, the composition comprises erythropoietin (EPO) as the agent. In certain embodiments, the disease to be treated or prevented is anemia, and the agent is erythropoietin (EPO).

In another aspect, provided is a method of delivering an agent to a subject (e.g., to the liver, lung, and/or spleen of the subject), cell, or tissue comprising administering a composition as described herein to the subject or cell. In certain embodiments, the method of delivering an agent comprises contacting a cell with a composition described herein that includes the agent. The cell may be in vitro or in vivo. In certain embodiments, the agent is selectively delivered to a target cell, compared to the delivery of the agent to a non-target cell. In certain embodiments, the agent is selectively delivered to a target tissue, compared to the delivery of the agent to a non-target tissue. In certain embodiments, the method increases the exposure of an agent to a subject or cell. In certain embodiments, the method increases the concentration of an agent in a subject or cell.

Another aspect of the present disclosure relates to kits comprising a container with a compound of Formula (I) or composition described herein. The kits may include a single dose or multiple doses of the composition. The kits may be useful in a method described herein. In certain embodiments, a kit of the disclosure further includes instructions for using a compound of Formula (I) or composition to a subject.

In another aspect, provided is a method of screening a library of compounds to identify one or more compounds of Formula (I) that are useful in the methods as described herein. The compound identified by the methods of screening may be useful for delivering an agent (e.g., a polynucleotide) to a subject (e.g., to the liver, lung, and/or spleen of the subject) or cell. The compound identified by the methods of screening may also be useful in treating and/or preventing a disease as described herein.

The details of one or more embodiments of the invention are set forth herein. Other features, objects, and advantages of the invention will be apparent from the Detailed Description, the Figures, the Examples, and the Claims.

DEFINITIONS

Chemical Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen ($^1H$) by deuterium ($^2H$) or tritium ($^3H$), replacement of $^{19}F$ with $^{18}F$, or the replacement of a carbon ($^{12}C$) by a $^{13}C$- or $^{14}C$-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, an n-alkyl, n-alkenyl, and n-alkynyl group refers to a "normal" straight-chain alkyl, straight-chain alkenyl, and straight-chain alkynyl chain, wherein the number of carbon atoms specified refers to the number of linear carbons in the alkyl, alkenyl, and alkynyl chain. Optional substitution along the straight-chain is limited to non-alkyl, non-alkenyl, and non-alkynyl groups, for example, halogen groups.

As used herein, "alkyl" refers to a radical of a straight-chain or branched saturated hydrocarbon group having from 1 to 40 carbon atoms ("$C_{1-40}$ alkyl"). In some embodiments, an alkyl group has 1 to 30 carbon atoms ("$C_{1-30}$ alkyl"). In some embodiments, an alkyl group has 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-30}$ alkyl. In certain embodiments, the alkyl group is a substituted $C_{1-30}$ alkyl.

As used herein, "heteroalkyl" refers to an alkyl group as defined herein which further includes at least one heteroatom (e.g., 1 to 10, e.g., 1, 2, 3, or 4 heteroatoms) selected from oxygen, sulfur, nitrogen, boron, silicon, or phosphorus within (i.e., inserted between adjacent carbon atoms of) and/or placed at one or more terminal position(s) of the parent chain. In certain embodiments, a heteroalkyl group refers to a saturated group having from 1 to 40 carbon atoms and 1 or more heteroatoms within the parent chain ("hetero$C_{1-40}$ alkyl"). In certain embodiments, a heteroalkyl group refers to a saturated group having from 1 to 30 carbon atoms and 1 or more heteroatoms within the parent chain ("hetero$C_{1-30}$ alkyl"). In certain embodiments, a heteroalkyl group refers to a saturated group having from 1 to 20 carbon atoms and 1 or more heteroatoms within the parent chain ("hetero$C_{1-20}$ alkyl"). In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and for 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-30}$ alkyl. In certain embodiments, the heteroalkyl group is a substituted hetero$C_{1-30}$ alkyl.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

As used herein, "alkenyl" refers to a radical of a straight-chain or branched hydrocarbon group having from 2 to 40 carbon atoms and one or more carbon-carbon double bonds (e.g., 1, 2, 3, or 4 double bonds) ("$C_{2-40}$ alkenyl"). In some embodiments, an alkenyl group has 2 to 30 carbon atoms ("$C_{2-30}$ alkenyl"). In some embodiments, an alkenyl group has 2 to 20 carbon atoms ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-30}$ alkenyl. In certain embodiments, the alkenyl group is a substituted $C_{2-30}$ alkenyl.

As used herein, "heteroalkenyl" refers to an alkenyl group as defined herein which further includes at least one heteroatom (e.g., 1 to 25, e.g., 1, 2, 3, or 4 heteroatoms) selected from oxygen, sulfur, nitrogen, boron, silicon, or phosphorus within (i.e., inserted between adjacent carbon atoms of) and/or placed at one or more terminal position(s) of the parent chain. In certain embodiments, a heteroalkenyl group refers to a group having from 2 to 40 carbon atoms, at least one double bond, and 1 or more heteroatoms within the parent chain ("hetero$C_{2-40}$ alkenyl"). In certain embodiments, a heteroalkenyl group refers to a group having from 2 to 30 carbon atoms, at least one double bond, and 1 or more heteroatoms within the parent chain ("hetero$C_{2-30}$ alkenyl"). In certain embodiments, a heteroalkenyl group refers to a group having from 2 to 20 carbon atoms, at least one double bond, and 1 or more heteroatoms within the parent chain ("hetero$C_{2-20}$ alkenyl"). In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and for 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-30}$ alkenyl. In certain embodiments, the heteroalkenyl group is a substituted hetero$C_{2-30}$ alkenyl.

As used herein, "alkynyl" refers to a radical of a straight-chain or branched hydrocarbon group having from 2 to 40 carbon atoms and one or more carbon-carbon triple bonds (e.g., 1, 2, 3, or 4 triple bonds) and optionally one or more double bonds (e.g., 1, 2, 3, or 4 double bonds) ("$C_{2-40}$ alkynyl"). In some embodiments, an alkynyl group has 2 to 30 carbon atoms ("$C_{2-30}$ alkynyl"). In some embodiments, an alkynyl group has 2 to 20 carbon atoms ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-30}$ alkynyl. In certain embodiments, the alkynyl group is a substituted $C_{2-30}$ alkynyl.

As used herein, "heteroalkynyl" refers to an alkynyl group as defined herein which further includes at least one heteroatom (e.g., 1 to 25, e.g., 1, 2, 3, or 4 heteroatoms) selected from oxygen, sulfur, nitrogen, boron, silicon, or phosphorus within (i.e., inserted between adjacent carbon atoms of) and/or placed at one or more terminal position(s) of the parent chain. In certain embodiments, a heteroalkynyl group refers to a group having from 2 to 40 carbon atoms, at least one triple bond, and 1 or more heteroatoms within the parent chain ("hetero$C_{2-40}$ alkynyl"). In certain embodiments, a heteroalkynyl group refers to a group having from 2 to 30 carbon atoms, at least one triple bond, and 1 or more heteroatoms within the parent chain ("hetero$C_{2-30}$ alkynyl"). In certain embodiments, a heteroalkynyl group refers to a group having from 2 to 20 carbon atoms, at least one triple bond, and 1 or more heteroatoms within the parent chain ("hetero$C_{2-20}$ alkynyl"). In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and for 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-30}$ alkynyl. In certain embodiments, the heteroalkynyl group is a substituted heteroC$_{2-30}$ alkynyl.

As used herein, "carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-10}$ carbocyclyl. In certain embodiments, the carbocyclyl group is a substituted C$_{3-10}$ carbocyclyl.

In some embodiments, "carbocyclyl" or "carbocyclic" is referred to as a "cycloalkyl", i.e., a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-10}$ cycloalkyl. In certain embodiments, the cycloalkyl group is a substituted C$_{3-10}$ cycloalkyl.

As used herein, "heterocyclyl" or "heterocyclic" refers to a radical of a 3- to 14-membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, or phosphorus ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, or phosphorus ("5-10 membered heterocyclyl"). In some embodiments, a heterocyclyl group is a 5-8 membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, or phosphorus ("5-8 membered heterocyclyl"). In some embodiments, a heterocyclyl group is a 5-6 membered non-aromatic ring system having ring carbon atoms and 1 or more (e.g., 1, 2, 3, or 4) ring heteroatoms, wherein each heteroatom is independently selected from oxygen, sulfur, nitrogen, boron, silicon, or phosphorus ("5-6 membered heterocyclyl"). In some embodiments, the 5-6 membered heterocyclyl has 1 or more (e.g., 1, 2, or 3) ring heteroatoms selected from oxygen, sulfur, nitrogen, boron, silicon, or phosphorus. In some embodiments, the 5-6 membered heterocyclyl has 1 or 2 ring heteroatoms selected from oxygen, sulfur, nitrogen, boron, silicon, or phosphorus. In some embodiments, the 5-6 membered heterocyclyl has 1 ring heteroatom selected from oxygen, sulfur, nitrogen, boron, silicon, or phosphorus.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of alkyl and aryl, as defined herein, and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

As used herein, "heteroaryl" refers to a radical of a 5-14 membered monocyclic or polycyclic (e.g., bicyclic or tricyclic) 4n+2 aromatic ring system (e.g., having 6, 10, or 14 π electrons shared in a cyclic array) having ring carbon atoms and 1 or more (e.g., 1, 2, 3, or 4) ring heteroatoms ring heteroatoms provided in the aromatic ring system, wherein each heteroatom is independently selected from oxygen, sulfur, nitrogen, boron, silicon, or phosphorus ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1 or more (e.g., 1, 2, 3, or 4) ring heteroatoms provided in the aromatic ring system, wherein each heteroatom is independently selected from oxygen, sulfur, nitrogen, boron, silicon, or phosphorus ("5-10 membered heteroaryl"). In some embodiments, a heteroaryl group is a 5-8 membered aromatic ring system having ring carbon atoms and 1 or more (e.g., 1, 2, 3, or 4) ring heteroatoms provided in the aromatic ring system, wherein each heteroatom is independently selected from oxygen, sulfur, nitrogen, boron, silicon, or phosphorus ("5-8 membered heteroaryl"). In some embodiments, a heteroaryl group is a 5-6 membered aromatic ring system having ring carbon atoms and 1 or more (e.g., 1, 2, 3, or 4) ring heteroatoms provided in the aromatic ring system, wherein each heteroatom is independently selected from oxygen, sulfur, nitrogen, boron, silicon, or phosphorus ("5-6 membered heteroaryl"). In some embodiments, the 5-6 membered heteroaryl has 1 or more (e.g., 1, 2, or 3) ring heteroatoms selected from oxygen, sulfur, nitrogen, boron, silicon, or phosphorus. In some embodiments, the 5-6 membered heteroaryl has 1 or 2 ring heteroatoms selected from oxygen, sulfur, nitrogen, boron, silicon, or phosphorus. In some embodiments, the 5-6 membered heteroaryl has 1 ring heteroatom selected from oxygen, sulfur, nitrogen, boron, silicon, or phosphorus. Unless otherwise specified, each instance of a heteroaryl group is independently unsubstituted (an "unsubstituted heteroaryl")

or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of alkyl and heteroaryl, as defined herein, and refers to an optionally substituted alkyl group substituted by an optionally substituted heteroaryl group.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Alkyl, alkenyl, alkynyl, heteroalkyl, heteroalkenyl, heteroalkynyl, carbocyclyl, heterocyclyl, aryl, and heteroaryl groups, as defined herein, which are divalent bridging groups are further referred to using the suffix-ene, e.g., alkylene, alkenylene, alkynylene, heteroalkylene, heteroalkenylene, heteroalkynylene, carbocyclylene, heterocyclylene, arylene, and heteroarylene.

The term "optionally substituted" refers to substituted or unsubstituted.

As understood from the above, alkyl, alkenyl, alkynyl, heteroalkyl, heteroalkenyl, heteroalkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SeH, —SeR$^{aa}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, C$_{1-10}$ alkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{2-10}$ alkenyl, C$_{2-10}$ alkynyl, C$_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$), —C(=S)N(R$^{ff}$)$_2$, —C(=O)SR$^{ee}$, —C(=S)SR$^{ee}$, —SC(=S)SR$^{ee}$, $C_{1-10}$ alkyl, $C_{2-10}$ alkenyl, $C_{2-10}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-10}$ alkyl, $C_{2-10}$ alkenyl, $C_{2-10}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-10}$ alkyl, $C_{2-10}$ alkenyl, $C_{2-10}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-10}$ alkyl, —ON(C$_{1-10}$ alkyl)$_2$, —N(C$_{1-10}$ alkyl)$_2$, —N(C$_{1-10}$ alkyl)$_3^+$X$^-$, —NH(C$_{1-10}$ alkyl)$_2^+$X$^-$, —NH$_2$(C$_{1-10}$ alkyl)$^+$X$^-$, —NH$_3^+$X$^-$, —N(OC$_{1-10}$ alkyl)(C$_{1-10}$ alkyl), —N(OH)(C$_{1-10}$ alkyl), —NH(OH), —SH, —SC$_{1-10}$ alkyl, —SS(C$_{1-10}$ alkyl), —C(=O)(C$_{1-10}$ alkyl), —CO$_2$H, —CO$_2$(C$_{1-10}$ alkyl), —OC(=O)(C$_{1-10}$ alkyl), —OCO$_2$(C$_{1-10}$ alkyl), —C(=O)NH$_2$, —C(=O)N(C$_{1-10}$ alkyl)$_2$, —OC(=O)NH(C$_{1-10}$ alkyl), —NHC(=O)(C$_{1-10}$ alkyl), —N(C$_{1-10}$ alkyl)C(=O)(C$_{1-10}$ alkyl), —NHCO$_2$(C$_{1-10}$ alkyl), —NHC(=O)N(C$_{1-10}$ alkyl)$_2$, —NHC(=O)NH(C$_{1-10}$ alkyl), —NHC(=O)NH$_2$, —C(=NH)O(C$_{1-10}$ alkyl), —OC(=NH)(C$_{1-10}$ alkyl), —OC(=NH)OC$_{1-10}$ alkyl, —C(=NH)N(C$_{1-10}$ alkyl)$_2$, —C(=NH)NH(C$_{1-10}$ alkyl), —C(=NH)NH$_2$, —OC(=NH)N(C$_{1-10}$ alkyl)$_2$, —OC(NH)NH(C$_{1-10}$ alkyl), —OC(NH)NH$_2$, —NHC(NH)N(C$_{1-10}$ alkyl)$_2$, —NHC(=NH)NH$_2$, —NHSO$_2$(C$_{1-10}$ alkyl), —SO$_2$N(C$_{1-10}$ alkyl)$_2$, —SO$_2$NH(C$_{1-10}$ alkyl), —SO$_2$NH$_2$, —SO$_2$C$_{1-10}$ alkyl, —SO$_2$OC$_{1-10}$ alkyl, —OSO$_2$C$_{1-10}$ alkyl, —SOC$_{1-10}$ alkyl, —Si(C$_{1-10}$ alkyl)$_3$, —OSi(C$_{1-10}$ alkyl)$_3$-C(=S)N(C$_{1-10}$ alkyl)$_2$, C(=S)NH(C$_{1-10}$ alkyl), C(=S)NH$_2$, —C(=O)S(C$_{1-10}$ alkyl), —C(=S)SC$_{1-10}$ alkyl, —SC(=S)SC$_{1-10}$alkyl, $C_{1-10}$ alkyl, $C_{2-10}$ alkenyl, $C_{2-10}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S;

wherein X$^-$ is a counterion.

In certain embodiments, the one or more substituents are selected from the group consisting of halogen, —CN, —NO$_2$, —N$_3$, —SO$_2$H, —SO$_3$H, —OH, —OR$^{aa}$, —N(R$^{bb}$)$_2$, —SH, —SR$^{aa}$, —C(=O)R$^{aa}$, —CO$_2$H, —CHO, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —S(=O)R$^{aa}$, —Si(R$^{aa}$)$_3$, —OSi(R$^{aa}$)$_3$—C(=O)SR$^{aa}$, —OC(=O)SR$^{aa}$, —SC(=O)OR$^{aa}$, —SC(=O)R$^{aa}$, $C_{1-10}$ alkyl, $C_{2-10}$ alkenyl, $C_{2-10}$ alkynyl, $C_{3-6}$ carbocyclyl, 3-6 membered heterocyclyl, $C_6$ aryl, and 5-6 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methan-sulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, and —OSi(R$^{aa}$)$_3$, wherein R$^{aa}$, R$^{bb}$, and R$^{cc}$ are as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

As used herein, the term, "amino" refers to the group —NH$_2$. The term "substituted amino," by extension, refers to a monosubstituted amino, a disubstituted amino, or a trisubstituted amino, as defined herein. In certain embodiments, the "substituted amino" is a monosubstituted amino or a disubstituted amino group.

As used herein, the term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, and —NHSO$_2$R$^{aa}$, wherein R$^{aa}$, R$^{bb}$ and R$^{cc}$ are as defined herein, and wherein R$^{bb}$ of the group —NH(R$^{bb}$) is not hydrogen.

As used herein, the term "disubstituted amino" refers to an amino group wherein the nitrogen atom directly attached to the parent molecule is substituted with two groups other than hydrogen, and includes groups selected from —N($R^{bb}$)$_2$, —$NR^{bb}$C(=O)$R^{aa}$, —$NR^{bb}CO_2R^{aa}$, —$NR^{bb}$C(=O)N($R^{bb}$)$_2$, —$NR^{bb}$C(=N$R^{bb}$)N($R^{bb}$)$_2$, and —$NR^{bb}SO_2R^{aa}$, wherein $R^{aa}$, $R^{bb}$, and $R^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+$ $X^-$, wherein $R^{bb}$ and $X^-$ are as defined herein.

As used herein, the term "acyl" refers a group wherein the carbon directly attached to the parent molecule is sp$^2$ hybridized, and is substituted with an oxygen, nitrogen or sulfur atom, e.g., a group selected from ketones (—C(=O)$R^{aa}$), carboxylic acids (—CO$_2$H), aldehydes (—CHO), esters (—CO$_2R^{aa}$, —C(=O)S$R^{aa}$, —C(=S)S$R^{aa}$), amides (—C(=O)N($R^{bb}$)$_2$, —C(=O)N$R^{bb}SO_2R^{aa}$, —C(=S)N($R^{bb}$)$_2$), and imines (—C(=N$R^{bb}$)$R^{aa}$, —C(=N$R^{bb}$)O$R^{aa}$, —C(=N$R^{bb}$)N($R^{bb}$)$_2$), wherein $R^{aa}$ and $R^{bb}$ are as defined herein.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, C$_{1-10}$ alkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S $R^{cc}$, —C(=S)S$R^{cc}$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on a nitrogen atom is a nitrogen protecting group (also referred to as an amino protecting group). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$)O$R^{aa}$, —C(=N$R^{cc}$) N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —S(=O)R$^{aa}$, —SO$_2$R$^{aa}$, and —Si(R$^{aa}$)$_3$ wherein R$^{aa}$ and R$^{bb}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is an sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, and —$Si(R^{aa})_3$ wherein $R^{aa}$ and $R^{bb}$ are as defined herein. Sulfur protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

These and other exemplary substituents are described in more detail in the Detailed Description, Examples, Figures, and Claims. The invention is not intended to be limited in any manner by the above exemplary listing of substituents.

Other Definitions

The following definitions are more general terms used throughout the present application.

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds as described herein include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19, incorporated herein by reference. Pharmaceutically acceptable salts of the compounds as described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, the term "small organic molecule" or "small molecule" refers to an organic molecule with a molecular weight of 1,000 g/mol or less. In certain embodiments, the molecular weight of a small molecule is at most about 1,000 g/mol, at most about 900 g/mol, at most about 800 g/mol, at most about 700 g/mol, at most about 600 g/mol, at most about 500 g/mol, at most about 400 g/mol, at most about 300 g/mol, at most about 200 g/mol, or at most about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and at most about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as an "small organometallic molecule."

As used herein, a "large organic molecule" or "large molecule" refers to an organic compound with a molecular weight of greater than about 1,000 g/mol. In certain embodiments, the molecular weight of a large molecule is greater than about 2,000 g/mol, greater than about 3,000 g/mol, greater than about 4,000 g/mol, or greater than about 5,000 g/mol. In certain embodiments, the molecular weight of a large molecule is at most about 100,000 g/mol, at most about 30,000 g/mol, at most about 10,000 g/mol, at most about 5,000 g/mol, or at most about 2,000 g/mol. Combinations of the above ranges (e.g., greater than about 2,000 g/mol and at most about 10,000 g/mol) are also possible. In certain embodiments, the large molecule is a therapeutically active agent such as a drug (e.g., a molecule approved by the U.S. Food and Drug Administration as provided in the Code of Federal Regulations (C.F.R.)). The large molecule may also be complexed with one or more metal atoms and/or metal ions. In this instance, the large molecule is also referred to as an "large organometallic compound."

A "protein," "peptide," or "polypeptide" comprises a polymer of amino acid residues linked together by peptide bonds. The term, as used herein, refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The term "apolipoprotein" refers to a protein that binds a lipid (e.g., triacylglycerol or cholesterol) to form a lipoprotein. Apolipoproteins also serve as enzyme cofactors, receptor ligands, and lipid transfer carriers that regulate the metabolism of lipoproteins and their uptake in tissues. Major types of apolipoproteins include integral and non-integral apolipoproteins. Exemplary apolipoproteins include apoA (e.g., apoA-I, apoA-II, apoA-IV, and apoA-V); apoB (e.g., apoB48 and apoB 100); apoC (e.g., apoC-I, apoC-II, apoC-III, and apoC-IV); apoD; apoE; apoH; and apoJ.

The term "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "chimeric construct" refers to any gene or a construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. The antisense oligonuculeotide may comprise a modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, a thio-guanine, and 2,6-diaminopurine. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing carbohydrate or lipids. Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), a provirus, a lysogen, repetitive DNA, satellite DNA, and viral DNA. Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), a polyinosinic acid, a ribozyme, a flexizyme, small nucleolar RNA (snoRNA), spliced leader RNA, viral RNA, and viral satellite RNA.

Polynucleotides described herein may be synthesized by standard methods known in the art, e.g., by use of an automated DNA synthesizer (such as those that are commercially available from Biosearch, Applied Biosystems, etc.). As examples, phosphorothioate oligonucleotides may be synthesized by the method of Stein et al., *Nucl. Acids Res.*, 16, 3209, (1988), methylphosphonate oligonucleotides can be prepared by use of controlled pore glass polymer supports (Sarin et al., *Proc. Natl. Acad. Sci. U.S.A.* 85, 7448-7451, (1988)). A number of methods have been developed for delivering antisense DNA or RNA to cells, e.g., antisense molecules can be injected directly into the tissue site, or modified antisense molecules, designed to target the desired cells (antisense linked to peptides or antibodies that specifically bind receptors or antigens expressed on the target cell surface) can be administered systemically. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Such promoters include, but are not limited to: the SV40 early promoter region (Bernoist et al., *Nature,* 290, 304-310, (1981); Yamamoto et al., *Cell,* 22, 787-797, (1980); Wagner et al., *Proc. Natl. Acad. Sci. U.S.A.* 78, 1441-1445, (1981); Brinster et al., *Nature* 296, 39-42, (1982)). Any type of plasmid, cosmid, yeast artificial chromosome or viral vector can be used to prepare the recombinant DNA construct that can be introduced directly into the tissue site. Alternatively, viral vectors can be used which selectively infect the desired tissue, in which case administration may be accomplished by another route (e.g., systemically).

The polynucleotides may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

A "recombinant nucleic acid molecule" is a nucleic acid molecule that has undergone a molecular biological manipulation, i.e., non-naturally occurring nucleic acid molecule or genetically engineered nucleic acid molecule. Furthermore, the term "recombinant DNA molecule" refers to a nucleic acid sequence which is not naturally occurring, or can be made by the artificial combination of two otherwise separated segments of nucleic acid sequence, i.e., by ligating together pieces of DNA that are not normally continuous. By "recombinantly produced" is meant artificial combination often accomplished by either chemical synthesis means, or by the artificial manipulation of isolated segments of nucleic acids, e.g., by genetic engineering techniques using restriction enzymes, ligases, and similar recombinant techniques as described by, for example, Sambrook et al., Molecular Cloning, second edition, Cold Spring Harbor Laboratory, Plainview, N.Y.; (1989), or Ausubel et al., Current Protocols in Molecular Biology, Current Protocols (1989), and DNA Cloning: A Practical Approach, Volumes I and II (ed. D. N. Glover) IREL Press, Oxford, (1985); each of which is incorporated herein by reference.

Such manipulation may be done to replace a codon with a redundant codon encoding the same or a conservative amino acid, while typically introducing or removing a sequence recognition site. Alternatively, it may be performed to join together nucleic acid segments of desired functions to generate a single genetic entity comprising a desired combination of functions not found in nature. Restriction enzyme recognition sites are often the target of such artificial manipulations, but other site specific targets, e.g., promoters, DNA replication sites, regulation sequences, control sequences, open reading frames, or other useful features may be incorporated by design. Examples of recombinant nucleic acid molecule include recombinant vectors, such as cloning or expression vectors which contain DNA sequences encoding Ror family proteins or immunoglobulin proteins which are in a 5' to 3' (sense) orientation or in a 3' to 5' (antisense) orientation.

The term "pDNA," "plasmid DNA," or "plasmid" refers to a small DNA molecule that is physically separate from, and can replicate independently of, chromosomal DNA within a cell. Plasmids can be found in all three major domains: Archaea, Bacteria, and Eukarya. In nature, plasmids carry genes that may benefit survival of the subject (e.g., antibiotic resistance) and can frequently be transmitted from one bacterium to another (even of another species) via horizontal gene transfer. Artificial plasmids are widely used as vectors in molecular cloning, serving to drive the replication of recombinant DNA sequences within host subjects. Plasmid sizes may vary from 1 to over 1,000 kbp. Plasmids are considered replicons, capable of replicating autonomously within a suitable host.

"RNA transcript" refers to the product resulting from RNA polymerase-catalyzed transcription of a DNA sequence. When the RNA transcript is a complementary copy of the DNA sequence, it is referred to as the primary transcript or it may be an RNA sequence derived from post-transcriptional processing of the primary transcript and is referred to as the mature RNA. "Messenger RNA (mRNA)" refers to the RNA that is without introns and can be translated into polypeptides by the cell. "cRNA" refers to complementary RNA, transcribed from a recombinant cDNA template. "cDNA" refers to DNA that is complementary to and derived from an mRNA template. The cDNA can be single-stranded or converted to double-stranded form using, for example, the Klenow fragment of DNA polymerase I.

A sequence "complementary" to a portion of an RNA, refers to a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

The terms "nucleic acid" or "nucleic acid sequence", "nucleic acid molecule", "nucleic acid fragment" or "polynucleotide" may be used interchangeably with "gene", "mRNA encoded by a gene" and "cDNA".

The term "mRNA" or "mRNA molecule" refers to messenger RNA, or the RNA that serves as a template for protein synthesis in a cell. The sequence of a strand of mRNA is based on the sequence of a complementary strand of DNA comprising a sequence coding for the protein to be synthesized.

The term "siRNA" or "siRNA molecule" refers to small inhibitory RNA duplexes that induce the RNA interference (RNAi) pathway, where the siRNA interferes with the expression of specific genes with a complementary nucleotide sequence. siRNA molecules can vary in length (e.g., between 18-30 or 20-25 basepairs) and contain varying degrees of complementarity to their target mRNA in the antisense strand. Some siRNA have unpaired overhanging bases on the 5' or 3' end of the sense strand and/or the antisense strand. The term siRNA includes duplexes of two separate strands, as well as single strands that can form hairpin structures comprising a duplex region.

The term "gene silencing" refers to an epigenetic process of gene regulation where a gene is "switched off" by a mechanism other than genetic modification. That is, a gene which would be expressed (i.e., "turned on") under normal circumstances is switched off by machinery in the cell. Gene silencing occurs when RNA is unable to make a protein during translation. Genes are regulated at either the transcriptional or post-transcriptional level. Transcriptional gene silencing is the result of histone modifications, creating an environment of heterochromatin around a gene that makes it inaccessible to transcriptional machinery (e.g., RNA polymerase and transcription factors). Post-transcriptional gene silencing is the result of mRNA of a particular gene being destroyed or blocked. The destruction of the mRNA prevents translation and thus the formation of a gene product (e.g., a protein). A common mechanism of post-transcriptional gene silencing is RNAi.

The term "particle" refers to a small object, fragment, or piece of a substance that may be a single element, inorganic material, organic material, or mixture thereof. Examples of particles include polymeric particles, single-emulsion particles, double-emulsion particles, coacervates, liposomes, microparticles, nanoparticles, macroscopic particles, pellets, crystals, aggregates, composites, pulverized, milled or otherwise disrupted matrices, and cross-linked protein or polysaccharide particles, each of which have an average characteristic dimension of about less than about 1 mm and at least 1 nm, where the characteristic dimension, or "critical dimension," of the particle is the smallest cross-sectional dimension of the particle. A particle may be composed of a single substance or multiple substances. In certain embodiments, the particle is not a viral particle. In other embodiments, the particle is not a liposome. In certain embodiments, the particle is not a micelle. In certain embodiments, the particle is substantially solid throughout. In certain embodiments, the particle is a nanoparticle. In certain embodiments, the particle is a microparticle.

The terms "composition" and "formulation" are used interchangeably.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is a non-human animal. In certain embodiments, the animal is a fish or reptile. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

As defined herein, the term "target tissue" refers to any biological tissue of a subject (including a group of cells, a body part, or an organ) or a part thereof, including blood and/or lymph vessels, which is the object to which a compound, particle, and/or composition of the invention is delivered. A target tissue may be an abnormal or unhealthy tissue, which may need to be treated. A target tissue may also be a normal or healthy tissue that is under a higher than normal risk of becoming abnormal or unhealthy, which may need to be prevented. In certain embodiments, the target tissue is the liver. In certain embodiments, the target tissue is the lung. A "non-target tissue" is any biological tissue of a subject (including a group of cells, a body part, or an organ) or a part thereof, including blood and/or lymph vessels, which is not a target tissue.

The term "administer," "administering," or "administration," as used herein, refers to implanting, absorbing, ingesting, injecting, inhaling, or otherwise introducing an inventive compound, or a composition thereof, in or on a subject.

As used herein, the terms "condition," "disease," and "disorder" are used interchangeably.

"As used herein, the terms "treatment," "treat," and "treating" refer to reversing, alleviating, delaying the onset of, or inhibiting the progress of a disease as described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound described herein is an amount sufficient to provide a therapeutic benefit in the treatment of a condition or to delay or minimize one or more symptoms associated with the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence, and which provides a prophylactic benefit in the prevention of the condition. The term "prophylactically effective amount" can encompass an amount that improves overall prophylaxis or enhances the prophylactic efficacy of another prophylactic agent.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-1 antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia, Charcot-Marie-Tooth disease, Crohn's disease, cleft lip, Cockayne syndrome, Coffin Lowry syndrome, colon cancer, congenital adrenal hyperplasia, Cornelia de Lange syndrome, Costello syndrome, Cowden syndrome, craniofrontonasal dysplasia, Crigler-Najjar syndrome, Creutzfeldt-Jakob disease, cystic fibrosis, deafness, depression, diabetes, diastrophic dysplasia, DiGeorge syndrome, Down's syndrome, dyslexia, Duchenne muscular dystrophy, Dubowitz syndrome, ectodermal dysplasia Ellis-van Creveld syndrome, Ehlers-Danlos, epidermolysis bullosa, epilepsy, essential tremor, familial hypercholesterolemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syndrome), Gorlin syndrome, Hailey-Hailey disease, hemihypertrophy, hemochromatosis, hemophilia (e.g., hemophilias A and B), hereditary motor and sensory neuropathy (HMSN), hereditary non polyposis colorectal cancer (HNPCC), Huntington's disease, immunodeficiency with hyper-IgM, juvenile onset diabetes, Klinefelter's syndrome, Kabuki syndrome, Leigh's disease, long QT syndrome, lung cancer, malignant melanoma, manic depression, Marfan syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan syndrome, obesity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome, Refsum disease, retinitis pigmentosa, retinoblastoma, Rett syndrome, Sanfilippo syndrome, schizophrenia, severe combined immunodeficiency, sickle cell anemia, spina bifida, spinal muscular atrophy, spinocerebellar atrophy, sudden adult death syndrome, Tangier disease, Tay-Sachs disease, thrombocytopenia absent radius syndrome, Townes-Brocks syndrome, tuberous sclerosis, Turner syndrome, Usher syndrome, von Hippel-Lindau syndrome, Waardenburg syndrome, Weaver syndrome, Werner syndrome, Williams syndrome, Wilson's disease, xeroderma piginentosum, and Zellweger syndrome.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

As used herein, the term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma; familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrinetumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

As used herein, the term "inflammatory disease" or "inflammation" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

As used herein, an "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigusvulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme arthritis, Guillain-Barré syndrome, Hashimoto's thyroiditis, and cardiomyopathy.

The term "liver disease" or "hepatic disease" refers to damage to or a disease of the liver. Non-limiting examples of liver disease include intrahepatic cholestasis (e.g., alagille syndrome, biliary liver cirrhosis), fatty liver (e.g., alcoholic fatty liver, Reye's syndrome), hepatic vein thrombosis, hepatolenticular degeneration (i.e., Wilson's disease), hepatomegaly, liver abscess (e.g., amebic liver abscess), liver cirrhosis (e.g., alcoholic, biliary, and experimental liver cirrhosis), alcoholic liver diseases (e.g., fatty liver, hepatitis, cirrhosis), parasitic liver disease (e.g., hepatic echinococcosis, fascioliasis, amebic liver abscess), jaundice (e.g., hemolytic, hepatocellular, cholestatic jaundice), cholestasis, portal hypertension, liver enlargement, ascites, hepatitis (e.g., alcoholic hepatitis, animal hepatitis, chronic hepatitis (e.g., autoimmune, hepatitis B, hepatitis C, hepatitis D, drug induced chronic hepatitis), toxic hepatitis, viral human hepatitis (e.g., hepatitis A, hepatitis B, hepatitis C, hepatitis D, hepatitis E), granulomatous hepatitis, secondary biliary cirrhosis, hepatic encephalopathy, varices, primary biliary cirrhosis, primary sclerosing cholangitis, hepatocellular adenoma, hemangiomas, bile stones, liver failure (e.g., hepatic encephalopathy, acute liver failure), angiomyolipoma, calcified liver metastases, cystic liver metastases, fibrolamellar hepatocarcinoma, hepatic adenoma, hepatoma, hepatic cysts (e.g., Simple cysts, Polycystic liver disease, hepatobiliary cystadenoma, choledochal cyst), mesenchymal tumors (mesenchymal hamartoma, infantile hemangioendothelioma, hemangioma, peliosis hepatis, lipomas, inflammatory pseudotumor), epithelial tumors (e.g., bile duct hamartoma, bile duct adenoma), focal nodular hyperplasia, nodular regenerative hyperplasia, hepatoblastoma, hepatocellular carcinoma, cholangiocarcinoma, cystadenocarcinoma, tumors of blood vessels, angiosarcoma, Karposi's sarcoma, hemangioendothelioma, embryonal sarcoma, fibrosarcoma, leiomyosarcoma, rhabdomyosarcoma, carcinosarcoma, teratoma, carcinoid, squamous carcinoma, primary lymphoma, peliosis hepatis, erythrohepatic porphyria, hepatic porphyria (e.g., acute intermittent porphyria, porphyria cutanea tarda), and Zellweger syndrome.

The term "spleen disease" refers to a disease of the spleen. Example of spleen diseases include, but are not limited to, splenomegaly, spleen cancer, asplenia, spleen trauma, idiopathic purpura, Felty's syndrome, Hodgkin's disease, and immune-mediated destruction of the spleen.

The term "lung disease" or "pulmonary disease" refers to a disease of the lung. Examples of lung diseases include, but are not limited to, bronchiectasis, bronchitis, bronchopulmonary dysplasia, interstitial lung disease, occupational lung disease, emphysema, cystic fibrosis, acute respiratory distress syndrome (ARDS), severe acute respiratory syndrome (SARS), asthma (e.g., intermittent asthma, mild persistent asthma, moderate persistent asthma, severe persistent asthma), chronic bronchitis, chronic obstructive pulmonary disease (COPD), emphysema, interstitial lung disease, sarcoidosis, asbestosis, aspergilloma, aspergillosis, pneumonia (e.g., lobar pneumonia, multilobar pneumonia, bronchial pneumonia, interstitial pneumonia), pulmonary fibrosis, pulmonary tuberculosis, rheumatoid lung disease, pulmonary embolism, and lung cancer (e.g., non-small-cell lung carcinoma (e.g., adenocarcinoma, squamous-cell lung carcinoma, large-cell lung carcinoma), small-cell lung carcinoma).

As used herein, a "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as Pernicious Anemia, Hemorrhagic Anemia, Hemolytic Anemia, Aplastic Anemia, Sickle Cell Anemia, Sideroblastic Anemia, Anemia associated with chronic infections such as Malaria, Trypanosomiasis, HTV, Hepatitis virus or other viruses, Myelophthisic Anemias caused by marrow deficiencies, renal failure resulting from Anemia, Anemia, Polycethemia, Infectious Mononucleosis (EVI), Acute Non-Lymphocytic Leukemia (ANLL), Acute Myeloid Leukemia (AML), Acute Promyelocytic Leukemia (APL), Acute Myelomonocytic Leukemia (AMMoL), Polycethemia Vera, Lymphoma, Acute Lymphocytic Leukemia (ALL), Chronic Lymphocytic Leukemia, Wilm's Tumor, Ewing's Sarcoma, Retinoblastoma, Hemophilia, disorders associated with an increased risk of Thrombosis, Herpes, Thalessemia, antibody-mediated disorders such as transfusion reactions and Erythroblastosis, mechanical trauma to red blood cells such as micro-angiopathic hemolytic anemias, Thrombotic Thrombocytopenic Purpura and disseminated intravascular coagulation, infections by parasites such as Plasmodium, chemical injuries from, e.g., lead poisoning, and Hypersplenism.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases also refer to a type of neurological disease marked by the loss of nerve cells, including, but not limited to, Alzheimer's disease, Parkinson's disease, amyotrophic lateral sclerosis, tauopathies (including fronto-temporal dementia), and Huntington's disease. Examples of neurological diseases include, but are not limited to, headache, stupor and coma, dementia, seizure, sleep disorders, trauma, infections, neoplasms, neuroophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include Acquired Epileptiform Aphasia; Acute Disseminated Encephalomyelitis; Adrenoleukodystrophy; agenesis of the corpus callosum; Agnosia; Aicardi syndrome; Alexander disease; Alpers' disease; Alternating hemiplegia; Alzheimer's disease; Amyotrophic lateral sclerosis; anencephaly; Angelman syndrome; Angiomatosis; Anoxia; aphasia; apraxia; Arachnoid Cysts; Arachnoiditis; Arnold-Chiari malformation; Arteriovenous malformation; Asperger syndrome; Ataxia Telangiectasia; Attention Deficit Hyperactivity Disorder; autism; autonomic dysfunction; Back Pain; Batten disease; Behcet's disease; Bell's palsy; Benign Essential Blepharospasm; Benign Focal; Amyotrophy; Benign Intracranial Hypertension; Binswanger's disease; Blepharospasm; Bloch Sulzberger syndrome; Brachial plexus injury; Brain abscess; Brain injury; Brain tumors (including Glioblastoma multiforme); Spinal tumor; Brown-Sequard syndrome; Canavan disease; Carpal tunnel syndrome (CTS); Causalgia; Central pain syndrome; Central pontine myelinolysis; Cephalic disorder; Cerebral aneurysm; Cerebral arteriosclerosis; Cerebral atrophy; Cerebral gigantism; Cerebral palsy; Charcot-Marie-Tooth disease; Chemotherapy-induced neuropathy and neuropathic pain; Chiari malformation; Chorea; Chronic inflammatory demyelinating polyneuropathy (CIDP); Chronic pain; Chronic regional pain syndrome; Coffin Lowry syndrome; Coma, including Persistent Vegetative State; Congenital facial diplegia; Corticobasal degeneration; Cranial arteritis; Craniosynostosis; Creutzfeldt-Jakob disease; Cumulative trauma disorders; Cushing's syndrome; Cytomegalic inclusion body disease (CIBD); Cytomegalovirus Infection; Dancing eyes-dancing feet syndrome; Dandy-Walker syndrome; Dawson disease; De Morsier's syndrome; Dejerine-Klumpke palsy; Dementia; Dermatomyositis; Diabetic neuropathy; Diffuse sclerosis; Dysautonomia; Dysgraphia; Dyslexia; Dystonias; Early infantile epileptic encephalopathy; Empty sella syndrome; Encephalitis; Encephaloceles; Encephalotrigeminal angiomatosis; Epilepsy; Erb's palsy; Essential tremor; Fabry's disease; Fahr's syndrome; Fainting; Familial spastic paralysis; Febrile seizures; Fisher syndrome; Friedreich's ataxia; Fronto-Temporal Dementia and other "Tauopathies"; Gaucher's disease; Gerstmann's syndrome; Giant cell arteritis; Giant cell inclusion disease; Globoid cell Leukodystrophy; Guillain-Barre syndrome; HTLV-1 associated myelopathy; Hallervorden-Spatz disease; Head injury; Headache; Hemifacial Spasm; Hereditary Spastic Paraplegia; Heredopathia atactica polyneuritiformis; Herpes zoster oticus; Herpes zoster; Hirayama syndrome; HIV-Associated Dementia and Neuropathy (see also Neurological manifestations of AIDS); Holoprosencephaly; Huntington's disease and other polyglutamine repeat diseases; Hydranencephaly; Hydrocephalus; Hypercortisolism; Hypoxia; Immune-Mediated encephalomyelitis; Inclusion body myositis; Incontinentia pigmenti; Infantile; phytanic acid storage disease; Infantile Refsum disease; Infantile spasms; Inflammatory myopathy; Intracranial cyst; Intracranial hypertension; Joubert syndrome; Kearns-Sayre syndrome; Kennedy disease; Kinsbourne syndrome; Klippel Feil syndrome; Krabbe disease; Kugelberg-Welander disease; Kuru; Lafora disease; Lambert-Eaton myasthenic syndrome; Landau-Kleffner syndrome; Lateral medullary (Wallenberg) syndrome; Learning disabilities; Leigh's disease; Lennox-Gastaut syndrome; Lesch-Nyhan syndrome; Leukodystrophy; Lewy body dementia; Lissencephaly; Locked-In syndrome; Lou Gehrig's disease (aka Motor Neuron Disease or Amyotrophic Lateral Sclerosis); Lumbar disc disease; Lyme disease-Neurological Sequelae; Machado-Joseph disease; Macrencephaly; Megalencephaly; Melkersson-Rosenthal syndrome; Menieres disease; Meningitis; Menkes disease; Metachromatic leukodystrophy; Microcephaly; Migraine; Miller Fisher syndrome; Mini-Strokes; Mitochondrial Myopathies; Mobius syndrome; Monomelic amyotrophy; Motor Neurone Disease; Moyamoya disease; Mucopolysaccharidoses; Multi-Infarct Dementia; Multifocal motor neuropathy; Multiple sclerosis and other demyelinating disorders;

Multiple system atrophy with postural hypotension; Muscular dystrophy; Myasthenia gravis; Myeloclastic diffuse sclerosis; Myoclonic encephalopathy of infants; Myoclonus; Myopathy; Myotonia congenital; Narcolepsy; Neurofibromatosis; Neuroleptic malignant syndrome; Neurological manifestations of AIDS; Neurological sequelae of lupus; Neuromyotonia; Neuronal ceroid lipofuscinosis; Neuronal migration disorders; Niemann-Pick disease; O'Sullivan-McLeod syndrome; Occipital Neuralgia; Occult Spinal Dysraphism Sequence; Ohtahara syndrome; Olivopontocerebellar Atrophy; Opsoclonus Myoclonus; Optic neuritis; Orthostatic Hypotension; Overuse syndrome; Paresthesia; Parkinson's disease; Paramyotonia Congenita; Paraneoplastic diseases; Paroxysmal attacks; Parry Romberg syndrome; Pelizaeus-Merzbacher disease; Periodic Paralyses; Peripheral Neuropathy; Painful Neuropathy and Neuropathic Pain; Persistent Vegetative State; Pervasive developmental disorders; Photic sneeze reflex; Phytanic Acid Storage disease; Pick's disease; Pinched Nerve; Pituitary Tumors; Polymyositis; Porencephaly; Post-Polio syndrome; Postherpetic Neuralgia (PHN); Postinfectious Encephalomyelitis; Postural Hypotension; Prader-Willi syndrome; Primary Lateral Sclerosis; Prion diseases; Progressive; Hemifacial Atrophy; Progressive multifocal leukoencephalopathy; Progressive Sclerosing Poliodystrophy; Progressive Supranuclear Palsy; Pseudotumor cerebri; Ramsay-Hunt syndrome (Type I and Type II); Rasmussen's Encephalitis; Reflex Sympathetic Dystrophy syndrome; Refsum disease; Repetitive Motion Disorders; Repetitive Stress Injuries; Restless Legs syndrome; Retrovirus-Associated Myelopathy; Rett syndrome; Reye's syndrome; Saint Vitus Dance; Sandhoff disease; Schilder's disease; Schizencephaly; Septo-Optic Dysplasia; Shaken Baby syndrome; Shingles; Shy-Drager syndrome; Sjogren's syndrome; Sleep Apnea; Soto's syndrome; Spasticity; Spina bifida; Spinal cord injury; Spinal cord tumors; Spinal Muscular Atrophy; Stiff-Person syndrome; Stroke; Sturge-Weber syndrome; Subacute Sclerosing Panencephalitis; Subarachnoid Hemorrhage; Subcortical Arteriosclerotic Encephalopathy; Sydenham Chorea; Syncope; Syringomyelia; Tardive dyskinesia; Tay-Sachs disease; Temporal arteritis; Tethered Spinal Cord syndrome; Thomsen disease; Thoracic Outlet syndrome; Tic Douloureux; Todd's Paralysis; Tourette syndrome; Transient ischemic attack; Transmissible Spongiform Encephalopathies; Transverse myelitis; Traumatic Brain injury; Tremor; Trigeminal Neuralgia; Tropical Spastic Paraparesis; Tuberous Sclerosis; Vascular Dementia (Multi-Infarct Dementia); Vasculitis including Temporal Arteritis; Von Hippel-Lindau Disease (VHL); Wallenberg's syndrome; Werdnig-Hoffman disease; West syndrome; Whiplash; Williams syndrome; Wilson's disease; and Zellweger syndrome.

A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawl symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

The term "psychiatric disorder" refers to a disease of the mind and includes diseases and disorders listed in the *Diagnostic and Statistical Manual of Mental Disorders—Fourth Edition* (DSM-IV), published by the American Psychiatric Association, Washington D. C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., type 1 diabetes, type 2 diabetes, gestational diabetes), hyperglycemia, hyperinsulinemia, insulin resistance, and obesity.

The term "musculoskeletal disease" or "MSD" refers to an injury and/or pain in a subject's joints, ligaments, muscles, nerves, tendons, and structures that support limbs, neck, and back. In certain embodiments, an MSD is a degenerative disease. In certain embodiments, an MSD includes an inflammatory condition. Body parts of a subject that may be associated with MSDs include upper and lower back, neck, shoulders, and extremities (arms, legs, feet, and hands). In certain embodiments, an MSD is a bone disease, such as achondroplasia, acromegaly, bone callus, bone demineralization, bone fracture, bone marrow disease, bone marrow neoplasm, dyskeratosis congenita, leukemia (e.g., hairy cell leukemia, lymphocytic leukemia, myeloid leukemia, Philadelphia chromosome-positive leukemia, plasma cell leukemia, stem cell leukemia), systemic mastocytosis, myelodysplastic syndromes, paroxysmal nocturnal hemoglobinuria, myeloid sarcoma, myeloproliferative disorders, multiple myeloma, polycythemia vera, pearson marrow-pancreas syndrome, bone neoplasm, bone marrow neoplasm, Ewing sarcoma, osteochondroma, osteoclastoma, osteosarcoma, brachydactyly, Camurati-Engelmann syndrome, Craniosynostosis, Crouzon craniofacial dysostosis, dwarfism, achondroplasia, bloom syndrome, Cockayne syndrome, Ellis-van Creveld syndrome, Seckel syndrome, spondyloepiphyseal dysplasia, spondyloepiphyseal dysplasia congenita, Werner syndrome, hyperostosis, osteophyte, Klippel-Trenaunay-Weber syndrome, Marfan syndrome, McCune-Albright syndrome, osteitis, osteoarthritis, osteochondritis, osteochondrodysplasia, Kashin-Beck disease, Leri-Weill dyschondrosteosis, osteochondrosis, osteodystrophy, osteogenesis imperfecta, osteolysis, Gorham-Stout syndrome, osteomalacia, osteomyelitis, osteonecrosis, osteopenia, osteopetrosis, osteoporosis, osteosclerosis, otospondylomegaepiphyseal dysplasia, pachydermoperiostosis, Paget disease of bone, Polydactyly, Meckel syndrome, rickets, Rothmund-Thomson syndrome, Sotos syndrome, spondyloepiphyseal dysplasia, spondyloepiphyseal dysplasia congenita, syndactyly, Apert syndrome, syndactyly type II, or Werner syndrome. In certain embodiments, an MSD is a cartilage disease, such as cartilage neoplasm, osteochondritis, osteochondrodysplasia, Kashin-Beck disease, or Leri-Weill dyschondrosteosis. In certain embodiments, an MSD is hernia, such as intervertebral disk hernia. In certain embodiments, an MSD is a joint disease, such as arthralgia, arthritis (e.g., gout (e.g., Kelley-Seegmiller syndrome, Lesch-Nyhan syndrome), Lyme disease, osteoarthritis, psoriatic arthritis, reactive arthritis, rheumatic fever, rheumatoid arthritis, Felty syndrome, synovitis, Blau syndrome, nail-patella syndrome, spondyloarthropathy, reactive arthritis, Stickler syndrome, synovial membrane disease, synovitis, or Blau syndrome. In certain embodiments, an MSD is Langer-Giedion syndrome. In certain embodiments, an MSD is a muscle disease, such as Barth syndrome, mitochondrial encephalomyopathy, MELAS syndrome, MERRF syndrome, MNGIE syndrome, mitochondrial myopathy, Kearns-Sayre syndrome, myalgia, fibromyalgia, polymyalgia rheumatica, myoma, myositis, dermatomyositis, neuromuscular disease, Kearns-Sayre syndrome, muscular dystrophy, myasthenia, congenital myasthenic syndrome, Lambert-Eaton myasthenic syndrome, myasthenia gravis, myotonia, myotonia congenita, spinal muscular atrophy, tetany, ophthalmoplegia, or rhabdomyolysis. In certain embodiments, an MSD is Proteus syndrome. In certain embodiments, an MSD is a rheumatic diseases, such as arthritis (e.g., gout (e.g., Kelley-Seegmiller syndrome, Lesch-Nyhan lyme disease)), osteoarthritis, psoriatic arthritis, reactive arthritis, rheumatic fever, rheumatoid arthritis, Felty syndrome, synovitis, Blau syndrome, gout (e.g., Kelley-Seegmiller syndrome, Lesch-Nyhan syndrome), polymyalgia rheumatica, rheumatic fever, rheumatic heart disease, or Sjogren syndrome. In certain embodiments, an MSD is Schwartz-Jampel syndrome. In certain embodiments, an MSD is a skeleton disease, such as Leri-Weill dyschondrosteosis, skeleton malformations, Melnick-Needles syndrome, pachydermoperiostosis, Rieger syndrome, spinal column disease, intervertebral disk hernia, scoliosis, spina bifida, spondylitis, ankylosing spondylitis, spondyloarthropathy, reactive arthritis, spondyloepiphyseal dysplasia, spondyloepiphyseal dysplasia congenita, or spondylosis.

BRIEF DESCRIPTION OF THE DRAWINGS

FIG. 3A: Batch-to-batch variability of OF-02 LNPs for EPO mRNA delivery in vivo. Data presented as mean+standard deviation (n=3). FIG. 3B: Dose response curves for OF-02 and cKK-E12 LNPs in vivo. Data presented as mean±standard deviation (n=3). FIG. 3C: Representative Cryogenic Transmission Electron Microscopy (CTEM) of OF-02 LNPs

DETAILED DESCRIPTION OF CERTAIN EMBODIMENTS OF THE INVENTION

Figure 1:
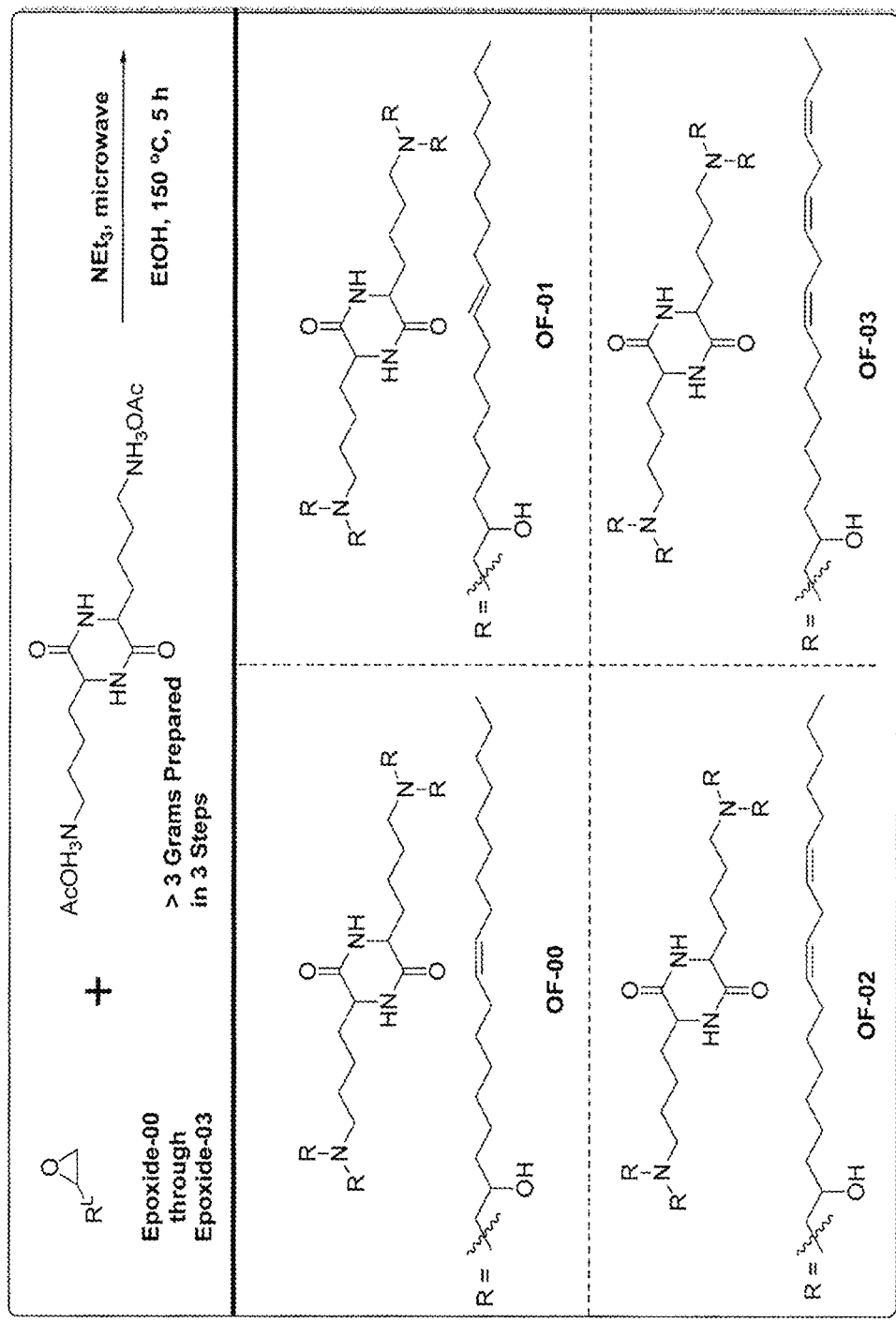
FIG. 1 depicts the synthesis of OF-00, OF-01, OF-02, and OF-03.

Described herein are novel alkenyl substituted 2,5-piperazinediones and uses thereof. In one aspect, the provided are compounds of Formula (I), and salts thereof. In another aspect, provided are compositions comprising a compound of Formula (I), or a salt thereof, and an agent, and optionally an excipient. The compositions have been found to be able to effectively deliver an agent to a subject or cell. A compound of Formula (I), which includes more than one amino moiety that may be protonated to form a positively charged ammonium cation, may bind to an agent that includes negatively charged moieties to form a non-covalent complex. The compound of Formula (I) also includes four (4) optionally substituted alkenyl $R^L$ moieties, as defined herein, which may assist the compound of Formula (I) and/or the complex of the compound of Formula (I) and the agent to pass through cell membranes and/or mask the charge on the agent to be delivered. In certain embodiments, the composition is useful in delivering an agent selectively to a particular tissue or organ (e.g., the liver and/or spleen) of the subject. The compositions (e.g., pharmaceutical compositions) may also be useful in treating and/or preventing a range of diseases, disorders, and conditions (e.g., a genetic disease, proliferative disease, hematological disease, neurological disease, liver disease, spleen disease, lung disease, painful condition, psychiatric disorder, musculoskeletal disease, a metabolic disorder, inflammatory disease, or autoimmune disease) in a subject in need thereof.

Compounds

In one aspect, provided are compounds of Formula (I):

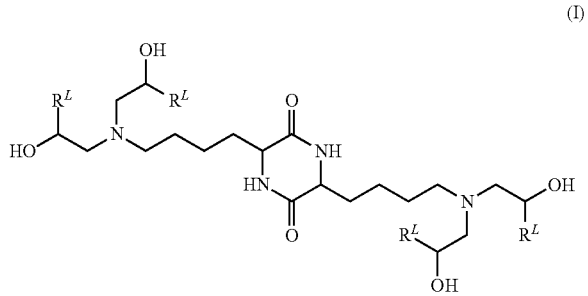

(I)

and salts thereof, wherein each instance of $R^L$ is independently optionally substituted $C_6$-$C_{40}$ alkenyl.

In certain embodiments, the compound of Formula (I) is of the formula:

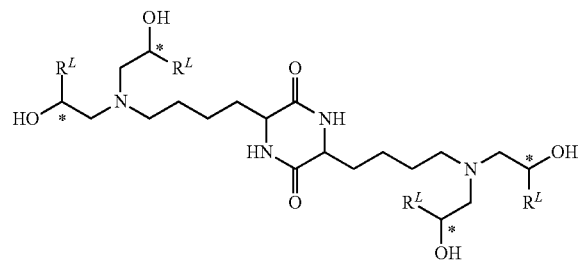

wherein the stereochemistry of each one of the four carbon atoms labeled with "*" is independently S or R.

In certain embodiments, at least two instances of R is the same group, e.g., for example, in certain embodiments, two instance, three instances, or all four instances, of $R^L$ are the same group. In certain embodiments, however, at least one instance of $R^L$ is different, e.g., for example, in certain embodiments, at least one, two, three, or all four instances of $R^L$ are different groups.

As generally defined herein, each instance of $R^L$ is independently optionally substituted $C_6$-$C_{40}$ alkenyl. In certain embodiments, at least one (e.g., one, two, three, or each) instance of $R^L$ is independently an optionally substituted $C_{6-30}$alkenyl, optionally substituted $C_{6-25}$alkenyl, optionally substituted $C_{6-20}$alkenyl, optionally substituted $C_{10-25}$alkenyl, optionally substituted $C_{10-20}$alkenyl, optionally substituted $C_{10-18}$alkenyl, optionally substituted $C_{10-16}$alkenyl, optionally substituted $C_{12-30}$alkenyl, optionally substituted $C_{14-30}$alkenyl, optionally substituted $C_{16-30}$alkenyl, optionally substituted $C_{12-18}$alkenyl, optionally substituted $C_{14-18}$alkenyl, optionally substituted $C_{16-18}$alkenyl, optionally substituted $C_{12-16}$alkenyl, or optionally substituted $C_{14-16}$alkenyl. In certain embodiments, at least one (e.g., one, two, three, or each) instance of $R^L$ is independently an optionally substituted $C_{12}$ alkenyl, an optionally substituted $C_{13}$ alkenyl, an optionally substituted $C_{14}$ alkenyl, an optionally substituted $C_{15}$alkenyl, an optionally substituted $C_{16}$ alkenyl, an optionally substituted $C_{17}$ alkenyl, an optionally substituted $C_{18}$ alkenyl, an optionally substituted $C_{19}$ alkenyl, or an optionally substituted $C_{20}$ alkenyl. In certain embodiments, one or more $R^L$ groups, as defined herein, is an unsubstituted alkenyl moiety. In certain embodiments, each of the $R^L$ groups, as defined herein, is an unsubstituted alkenyl moiety.

In certain embodiments, one or more $R^L$ groups, as defined herein, is an n-alkenyl moiety. For example, in certain embodiments, at least one (e.g., one, two, three, or each) instance of $R^L$ is independently optionally substituted $C_6$-$C_{40}$ n-alkenyl, e.g., in certain embodiments, at least one (e.g., one, two, three, or each) instance of $R^L$ is independently an optionally substituted $C_{6-30}$ n-alkenyl, optionally substituted $C_{6-25}$ n-alkenyl, optionally substituted $C_{6-20}$ n-alkenyl, optionally substituted $C_{10-25}$ n-alkenyl, optionally substituted $C_{10-20}$ n-alkenyl, optionally substituted $C_{10-18}$ n-alkenyl, optionally substituted $C_{10-16}$ n-alkenyl, optionally substituted $C_{12-30}$ n-alkenyl, optionally substituted $C_{14-30}$ n-alkenyl, optionally substituted $C_{16-30}$ n-alkenyl, optionally substituted $C_{12-18}$ n-alkenyl, optionally substituted $C_{14-18}$ n-alkenyl, optionally substituted $C_{16-18}$ n-alkenyl, optionally substituted $C_{12-16}$ n-alkenyl, or optionally substituted $C_{14-16}$ n-alkenyl. In certain embodiments, at least one (e.g., one, two, three, or each) instance of $R^L$ is independently an optionally substituted $C_{12}$ n-alkenyl, an optionally substituted $C_{13}$ n-alkenyl, an optionally substituted $C_{14}$ n-alkenyl, an optionally substituted $C_{15}$ n-alkenyl, an optionally substituted $C_{16}$ n-alkenyl, an optionally substituted $C_{17}$ n-alkenyl, an optionally substituted $C_{18}$ n-alkenyl, an optionally substituted $C_{19}$ n-alkenyl, or an optionally substituted $C_{20}$ n-alkenyl. In certain embodiments, one or more $R^L$ groups, as defined herein, is an unsubstituted n-alkenyl moiety. In certain embodiments, each of the $R^L$ groups, as defined herein, is an unsubstituted n-alkenyl moiety.

As understood herein, the alkenyl $R^L$ group comprises cis (Z) and/or trans (E) double bonds. It is understood that the designation of cis may also refer to the Z configuration, and the designation of trans may also refer to the E configuration of the double bond if the double bond is tri- or tetra-substituted. In certain embodiments, the only degrees of unsaturation in the group $R^L$ are attributed to olefinic (double) bonds. In certain embodiments, at least one (e.g., one, two, three, or each) instance of $R^L$ comprises only cis double bonds (and thus no trans double bonds). In certain embodiments, at least one (e.g., one, two, three, or each) instance of $R^L$ comprises only trans double bonds (and thus no cis double bonds). In certain embodiments, at least one (e.g., one, two, three, or each) instance of $R^L$ comprises 1, 2, or 3 double bonds. In certain embodiments, at least one (e.g., one, two, three, or each) instance of $R^L$ comprises 1, 2, or 3 double bonds, and no triple bonds. In certain embodiments, at least one (e.g., one, two, three, or each) instance of $R^L$ comprises 2 cis and/or trans double bonds. In certain embodiments, at least one (e.g., one, two, three, or each) instance of $R^L$ comprises only cis double bonds. In certain embodiments, trans alkenyl bonds provided in the $R^L$ group are specifically excluded. In certain embodiments, each instance of $R^L$ comprises only 2 cis double bonds.

In certain embodiments, wherein the at least one (e.g., one, two, three, or each) alkenyl $R^L$ group comprises only 1 double bond, the alkenyl $R^L$ group is optionally substituted —($C_{4-10}$ alkylene)-($C_2$alkenylene)-($C_{1-20}$alkyl), provided $R^L$ comprises no more than 40 linear carbon atoms (in other words, the number of carbon atoms within the linear carbon chain). In certain embodiments, the alkenyl $R^L$ group is an —($C_{4-10}$ n-alkylene)-($C_2$alkenylene)-($C_{1-20}$ n-alkyl), provided $R^L$ comprises no more than 40 linear carbon atoms. In certain embodiments, the alkenyl $R^L$ group is an optionally substituted —($C_{4-10}$alkylene)-(cis-$C_2$alkenylene)-

($C_{1-20}$alkyl) moiety, provided $R^L$ comprises no more than 40 linear carbon atoms. In certain embodiments, the alkenyl $R^L$ group is an optionally substituted —($C_{4-10}$n-alkylene)-(cis-$C_2$alkenylene)-($C_{1-20}$ n-alkyl) moiety, provided $R^L$ comprises no more than 40 linear carbon atoms. In certain embodiments, $R^L$ comprises no more than 30 linear carbon atoms. In certain embodiments, $R^L$ comprises between 6 to 40, 10 to 40, 10 to 30, or 10 to 20 linear carbon atoms, inclusive.

For example, in certain embodiments, wherein at least one (e.g., one, two, three, or each) alkenyl $R^L$ group comprises only 1 double bond, the at least one (e.g., one, two, three, or each) alkenyl $R^L$ group is a group of formula:

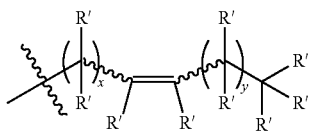

wherein:
x is an integer between 4 and 20, inclusive;
y is an integer between 1 and 20, inclusive; and
each instance of R' is independently hydrogen, optionally substituted $C_{1-6}$alkyl, halogen, substituted hydroxyl, substituted thiol, and substituted amino;
provided the group comprises no more than 40 linear carbon atoms.

In certain embodiments, wherein at least one (e.g., one, two, three, or each) alkenyl $R^L$ group comprises only 1 double bond, the at least one (e.g., one, two, three, or each) alkenyl $R^L$ group is a group of formula:

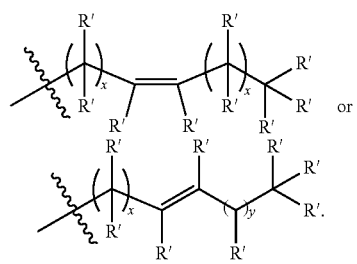

In certain embodiments, each R' is independently selected from the group consisting of hydrogen, unsubstituted $C_{1-6}$alkyl (e.g., —$CH_3$) haloalkyl (e.g., —$CF_3$), and halogen (e.g., —F). In certain embodiments, each R' is independently selected from the group consisting of hydrogen and halogen (e.g., —F). In certain embodiments, each R' is hydrogen.

In certain embodiments, wherein at least one (e.g., one, two, three, or each) alkenyl $R^L$ group comprises only 1 double bond, the at least one (e.g., one, two, three, or each) alkenyl $R^L$ group is a group of formula:

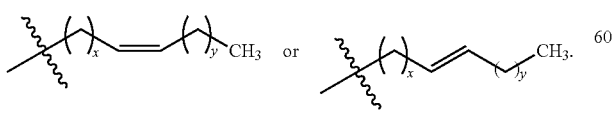

In certain embodiments, x is 4, 5, 6, 7, or 8. In certain embodiments, y is 1, 2, 3, 4, 5, 6, 7, 8, 9, or 10. In certain embodiments, x is 6. In certain embodiments, y is 7.

For example, in certain embodiments, wherein at least one (e.g., one, two, three, or each) alkenyl $R^L$ group comprises only 1 double bond, the at least one (e.g., one, two, three, or each) alkenyl $R^L$ group is a group of formula:

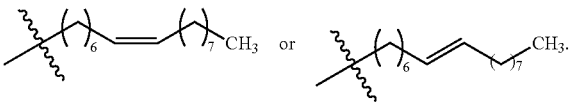

In certain embodiments, wherein the at least one (e.g., one, two, three, or each) alkenyl $R^L$ group comprises only 2 double bonds, the alkenyl $R^L$ group is optionally substituted —($C_{4-10}$alkylene)-($C_2$alkenylene)-($C_{1-3}$alkylene)-($C_2$alkenylene)-($C_{1-20}$alkyl) provided $R^L$ comprises no more than 40 linear carbon atoms (in other words, the number of carbon atoms within the linear carbon chain). In certain embodiments, the alkenyl $R^L$ group is an —($C_{4-10}$ n-alkylene)-($C_2$alkenylene)-($C_{1-3}$n-alkylene)-($C_2$alkenylene)-($C_{1-20}$ n-alkyl), provided $R^L$ comprises no more than 40 linear carbon atoms. In certain embodiments, the alkenyl $R^L$ group is an optionally substituted —($C_{4-10}$alkylene)-(cis-$C_2$alkenylene)-($C_{1-3}$alkylene)-(cis-$C_2$alkenylene)-($C_{1-20}$ alkyl) moiety, provided $R^L$ comprises no more than 40 linear carbon atoms. In certain embodiments, the alkenyl $R^L$ group is an optionally substituted —($C_{4-10}$n-alkylene)-(cis-$C_2$alkenylene)-($C_{1-3}$n-alkylene)-(cis-$C_2$alkenylene)-($C_{1-20}$n-alkyl) moiety, provided $R^L$ comprises no more than 40 linear carbon atoms. In certain embodiments, $R^L$ comprises no more than 30 linear carbon atoms. In certain embodiments, $R^L$ comprises between 6 to 40, 10 to 40, 10 to 30, or 10 to 20 linear carbon atoms, inclusive.

For example, in certain embodiments, wherein at least one (e.g., one, two, three, or each) alkenyl $R^L$ group comprises only 2 double bonds, the at least one (e.g., one, two, three, or each) alkenyl $R^L$ group is a group of formula:

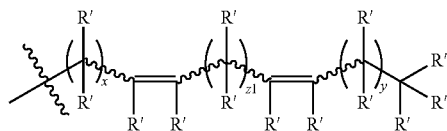

wherein:
x is an integer between 4 and 20, inclusive;
y is an integer between 1 and 20, inclusive;
z1 is 1, 2, or 3;
and
each instance of R' is independently hydrogen, optionally substituted $C_{1-6}$alkyl, halogen, substituted hydroxyl, substituted thiol, and substituted amino;
provided the group comprises no more than 40 linear carbon atoms.

In certain embodiments, wherein at least one (e.g., one, two, three, or each) alkenyl $R^L$ group comprises only 2 double bonds, the at least one (e.g., one, two, three, or each) alkenyl $R^L$ group is a group of formula:

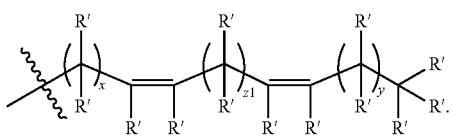

In certain embodiments, each R' is independently selected from the group consisting of hydrogen, unsubstituted $C_{1-6}$alkyl (e.g., —$CH_3$) haloalkyl (e.g., —$CF_3$), and halogen (e.g., —F). In certain embodiments, each R' is independently selected from the group consisting of hydrogen and halogen (e.g., —F). In certain embodiments, each R' is hydrogen.

In certain embodiments, wherein at least one (e.g., one, two, three, or each) alkenyl $R^L$ group comprises only 2 double bonds, the at least one (e.g., one, two, three, or each) alkenyl $R^L$ group is a group of formula:

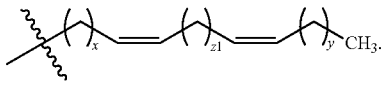

In certain embodiments, x is 4, 5, 6, 7, or 8. In certain embodiments, y is 1, 2, 3, 4, 5, 6, 7, 8, 9, or 10. In certain embodiments, z1 is 1 or 2. In certain embodiments, x is 6. In certain embodiments, y is 4. In certain embodiments, z1 is 1.

For example, in certain embodiments, wherein at least one (e.g., one, two, three, or each) alkenyl $R^L$ group comprises only 2 double bond, the at least one (e.g., one, two, three, or each) alkenyl $R^L$ group is a group of formula:

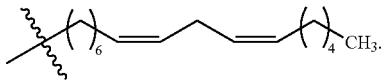

In certain embodiments, wherein the at least one (e.g., one, two, three, or each) alkenyl $R^L$ group comprises only 3 double bonds, the alkenyl $R^L$ group is an optionally substituted —($C_{4-10}$alkylene)-($C_2$alkenylene)-($C_{1-3}$alkylene)-($C_2$alkenylene)-($C_{1-3}$alkylene)-($C_2$alkenylene)-($C_{1-20}$alkyl) moiety, provided $R^L$ comprises no more than 40 linear carbon atoms (in other words, the number of carbon atoms within the linear carbon chain). In certain embodiments, the alkenyl $R^L$ group is an —($C_{4-10}$ n-alkylene)-($C_2$alkenylene)-($C_{1-3}$ n-alkylene)-($C_2$alkenylene)-($C_{1-3}$ n-alkylene)-($C_2$alkenylene)-($C_{1-20}$ n-alkyl), provided $R^L$ comprises no more than 40 linear carbon atoms. In certain embodiments, the alkenyl $R^L$ group is an optionally substituted —($C_{4-10}$alkylene)-(cis-$C_2$alkenylene)-($C_{1-3}$alkylene)-(cis-$C_2$alkenylene)-($C_{1-3}$alkylene)-(cis-$C_2$alkenylene)-($C_{1-20}$alkyl) moiety, provided $R^L$ comprises no more than 40 linear carbon atoms. In certain embodiments, the alkenyl $R^L$ group is an optionally substituted —($C_{4-10}$ n-alkylene)-(cis-$C_2$alkenylene)-($C_{1-3}$ n-alkylene)-(cis-$C_2$alkenylene)-($C_{1-3}$ n-alkylene)-(cis-$C_2$alkenylene)-($C_{1-20}$ n-alkyl) moiety, provided $R^L$ comprises no more than 40 linear carbon atoms. In certain embodiments, $R^L$ comprises no more than 30 linear carbon atoms. In certain embodiments, $R^L$ comprises between 6 to 40, 10 to 40, 10 to 30, or 10 to 20 linear carbon atoms, inclusive.

For example, in certain embodiments, wherein at least one (e.g., one, two, three, or each) alkenyl $R^L$ group comprises only 3 double bonds, the at least one (e.g., one, two, three, or each) alkenyl $R^L$ group is a group of formula:

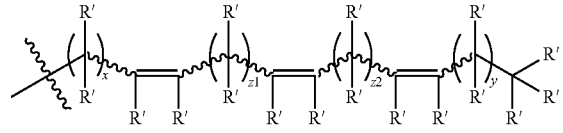

wherein:
x is an integer between 4 and 20, inclusive;
y is an integer between 1 and 20, inclusive;
each instance of z1 and z2 is independently 1, 2, or 3; and
each instance of R' is independently hydrogen, optionally substituted $C_{1-6}$alkyl, halogen, substituted hydroxyl, substituted thiol, and substituted amino;
provided the group comprises no more than 40 linear carbon atoms.

In certain embodiments, wherein the at least one (e.g., one, two, three, or each) alkenyl $R^L$ group comprises only 3 double bonds, the at least one (e.g., one, two, three, or each) alkenyl $R^L$ group is a group of formula:

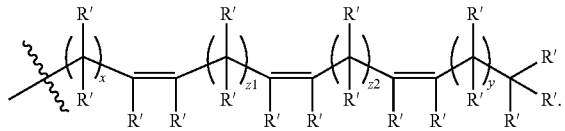

In certain embodiments, each R' is independently selected from the group consisting of hydrogen, unsubstituted $C_{1-6}$alkyl (e.g., —$CH_3$) haloalkyl (e.g., —$CF_3$), and halogen (e.g., —F). In certain embodiments, each R' is independently selected from the group consisting of hydrogen and halogen (e.g., —F). In certain embodiments, each R' is hydrogen.

In certain embodiments, wherein the at least one (e.g., one, two, three, or each) alkenyl $R^L$ group comprises only 3 double bonds, the at least one (e.g., one, two, three, or each) alkenyl $R^L$ group is a group of formula:

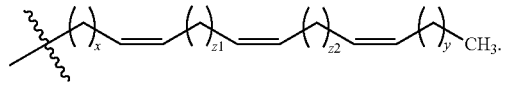

In certain embodiments, x is 4, 5, 6, 7, or 8. In certain embodiments, y is 1, 2, 3, 4, 5, 6, 7, 8, 9, or 10. In certain embodiments, z1 is 1 or 2. In certain embodiments, z2 is 1 or 2. In certain embodiments, x is 6. In certain embodiments, y is 1. In certain embodiments, z1 is 1. In certain embodiments, z2 is 1.

For example, in certain embodiments, wherein the least one (e.g., each) alkenyl $R^L$ group comprises only 2 double bonds, the at least one (e.g., one, two, three, or each) alkenyl $R^L$ group is a group of formula:

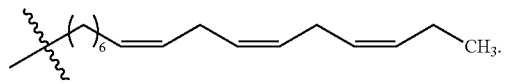

Exemplary compounds of Formula (I) include:
(OF-00), wherein each $R^L$ is a group of formula:

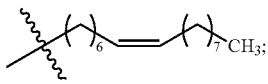

(00)

(OF-01), wherein each $R^L$ is a group of formula:

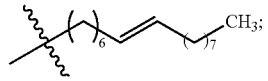

(01)

(OF-02), wherein each $R^L$ is a group of formula:

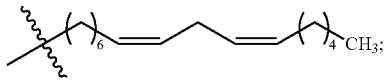

(02)

and
(OF-03), wherein each $R^L$ is a group of formula:

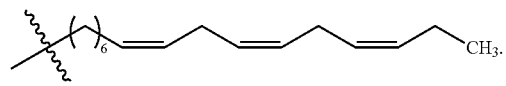

(03)

Compositions

Provided herein are compositions comprising a compound of Formula (I) or salt thereof, and an agent. In certain embodiments, the compositions are pharmaceutical compositions. In certain embodiments, the compositions are for non-medical applications. In certain embodiments, the compositions are cosmetic compositions. In certain embodiments, the compositions are dietary compositions. In certain embodiments, the compositions are nutraceutical compositions. In certain embodiments, a composition comprises a compound of Formula (I), or a salt thereof, and optionally an excipient. In certain embodiments, a composition comprises a compound of Formula (I), or a pharmaceutically acceptable salt thereof, and optionally a pharmaceutically acceptable excipient.

The compositions, as described herein, comprise one or more agents (e.g., a pharmaceutical agent, diagnostic agent, and/or polynuceotide). The agent may form a complex with a compound of Formula (I) or salt thereof in the composition. Agents and complexes are described in more detail herein. In certain embodiments, the composition is useful in the delivery of the agent to a subject in need thereof. In certain embodiments, the composition is useful in the delivery of an effective amount of the agent to the subject. In certain embodiments, the agent is covalently attached to the compound of Formula (I) or salt thereof in the composition. In certain embodiments, the agent is not covalently attached to the compound of Formula (I) or salt thereof in the composition.

The compositions comprising an agent may improve or increase the delivery of the agent to a subject or cell. In certain embodiments, the compositions increase the delivery of the agent to a target tissue of the subject. In certain embodiments, the compositions selectively deliver the agent to the target tissue (e.g., the compositions deliver more agent to the target tissue than to a non-target tissue). In certain embodiments, the compositions increase the delivery of the agent to the liver of the subject. In certain embodiments, the compositions increase the delivery of the agent to the spleen of the subject. In certain embodiments, the compositions selectively delivers the agent to the liver, lung, and/or spleen of the subject.

The delivery of the agent may be characterized in various ways, such as the exposure, concentration, and bioavailability of the agent. The exposure of an agent in a subject may be defined as the area under the curve (AUC) of the concentration of the agent in the subject or cell after administration or dosing. In certain embodiments, the exposure described herein is the exposure of the agent in a target tissue (e.g., the liver and/or spleen) of the subject. In general, an increase in exposure may be calculated by taking the difference in the AUC measured in a subject or cell between those of an inventive composition and a control composition, and dividing the difference by the exposure of the control composition. Exposure of an agent may be measured in an appropriate animal model. The concentration of an agent and, when appropriate, its metabolite(s), in a subject or cell is measured as a function of time after administration.

In certain embodiments, the concentration described herein is the concentration of the agent in a target tissue (e.g., the liver and/or spleen) of the subject. Concentration of an agent, and, when appropriate, of its metabolite(s), in a subject or cell, may be measured as a function of time in vivo using an appropriate animal model. One method of determining the concentration of an agent involves dissecting of a tissue or organ of the subject. The concentration of the agent in the subject or cell may be determined by HPLC or LC/MS analysis.

In some embodiments, the delivery of the agent increases due to the presence of a compound of Formula (I) or salt thereof in the composition. In some embodiments, the delivery of the agent increases due to the presence of a complex formed between the compound of Formula (I) or salt thereof and the agent in the composition. In some embodiments, the compositions increase the delivery of the agent by at least about 10%, at least about 20%, at least about 30%, at least about 40%, at least about 50%, at least about 100%, at least about 2-fold, at least about 3-fold, at least about 10-fold, at least about 30-fold, at least about 100-fold, at least about 300-fold, or at least about 1000-fold. In certain embodiments, the compositions increase the delivery of the agent by less than about 1000-fold, less than about 300-fold, less than about 100-fold, less than about 30-fold, less than about 10-fold, less than about 3-fold, less than about 2-fold, less than about 100%, less than about 50%, less than about 30%, less than about 20%, or less than about 10%. Combinations of the above-referenced ranges are also possible (e.g., an increase of at least about 100% and less than about 10 fold). Other ranges are also within the scope of the invention. In certain embodiments, a compound of Formula (I) or salt thereof is present in the composition in a sufficient amount to increase the delivery of the agent by an amount described herein compared to the delivery of the agent when administered in its absence.

The compositions may deliver an agent selectively to a tissue or organ of a subject. In certain embodiments, the tissue or organ to which the agent is selectively delivered to is a target tissue. In certain embodiments, the compositions deliver at least about 10%, at least about 20%, at least about 30%, at least about 40%, at least about 50%, at least about 70%, at least about 100%, at least about 3-fold, at least about 10-fold, at least about 30-fold, at least about 100-fold, at least about 300-fold, or at least about 1000-fold more amount of the agent to a target tissue than to a non-target tissue. The amount of agent may be measured by the exposure, concentration, and/or bioavailability of the agent in a tissue or organ as described herein. In certain embodiments, the compositions deliver at most about 1000-fold, at most about 300-fold, at most about 100-fold, at most about 30-fold, at most about 10-fold, at most about 3-fold, at most about 100%, at most about 70%, at most about 50%, at most about 40%, at most about 30%, at most about 20%, or at most about 10% more amount of the agent to a target tissue than to a non-target tissue. Combinations of the above ranges (e.g., at least about 100% and at most about 10 fold) are also with the scope of the invention. In certain embodiments, the target tissue is the liver. In certain embodiments, the target tissue is the spleen. In certain embodiments, the target tissue is the lung.

The compositions (e.g., pharmaceutical compositions) including one or more agents (e.g., pharmaceutical agents) may be useful in treating and/or preventing a disease, disorder or condition. In certain embodiments, the disease, disorder, or condition is a genetic disease, proliferative disease, hematological disease, neurological disease, liver disease, spleen disease, lung disease, painful condition, psychiatric disorder, musculoskeletal disease, a metabolic disorder, inflammatory disease, or autoimmune disease. In certain embodiments, the compositions are useful in gene therapy. In certain embodiments, the compositions are useful for treating and/or preventing a genetic disease. In certain embodiments, the compositions are useful for treating and/or preventing a proliferative disease. In certain embodiments, the compositions are useful for treating and/or preventing cancer. In certain embodiments, the compositions are useful for treating and/or preventing a benign neoplasm. In certain embodiments, the compositions are useful for treating and/or preventing pathological angiogenesis. In certain embodiments, the compositions are useful for treating and/or preventing an inflammatory disease. In certain embodiments, the compositions are useful for treating and/or preventing an autoimmune disease. In certain embodiments, the compositions are useful for treating and/or preventing a hematological disease. In certain embodiments, the compositions are useful for treating and/or preventing a neurological disease. In certain embodiments, the compositions are useful for treating and/or preventing a liver disease. In certain embodiments, the compositions are useful for treating and/or preventing a lung disease. In certain embodiments, the compositions are useful for treating and/or preventing a spleen disease. In certain embodiments, the compositions are useful for treating and/or preventing hepatic carcinoma, hypercholesterolemia, refractory anemia, familial amyloid neuropathy, or hemophilia.

The agents may be provided in an effective amount in a composition. In certain embodiments, the effective amount is a therapeutically effective amount. In certain embodiments, the effective amount is a prophylactically effective amount. In certain embodiments, the effective amount is an amount effective for treating and/or preventing a disease. In certain embodiments, the effective amount is an amount effective for treating a disease, e.g., a genetic disease, proliferative disease, hematological disease, neurological disease, liver disease, spleen disease, lung disease, painful condition, psychiatric disorder, musculoskeletal disease, a metabolic disorder, inflammatory disease, or autoimmune disease. In certain embodiments, the effective amount is an amount effective for treating and/or preventing a genetic disease. In certain embodiments, the effective amount is an amount effective for treating and/or preventing a proliferative disease. In certain embodiments, the effective amount is an amount effective for treating and/or preventing cancer. In certain embodiments, the effective amount is an amount effective for treating and/or preventing a benign neoplasm. In certain embodiments, the effective amount is an amount effective for treating and/or preventing pathological angiogenesis. In certain embodiments, the effective amount is an amount effective for treating and/or preventing an inflammatory disease. In certain embodiments, the effective amount is an amount effective for treating and/or preventing an autoimmune disease. In certain embodiments, the effective amount is an amount effective for treating and/or preventing a hematological disease. In certain embodiments, the effective amount is an amount effective for treating and/or preventing a neurological disease. In certain embodiments, the effective amount is an amount effective for treating and/or preventing a liver disease. In certain embodiments, the effective amount is an amount effective for treating and/or preventing a lung disease. In certain embodiments, the effective amount is an amount effective for treating and/or preventing a spleen disease. In certain embodiments, the effective amount is an amount effective for treating and/or preventing hepatic carcinoma, hypercholesterolemia, refractory anemia, familial amyloid neuropathy, or hemophilia.

An effective amount of an agent may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

In certain embodiments, the compositions are in the form of a particle. In certain embodiments, the particle is a nanoparticle or microparticle. In certain embodiments, the compositions are in the form of liposomes or micelles. It is understood that, in certain embodiments, the particles, micelles, or liposomes described herein result from self-assembly of the components of the composition. In certain embodiments, the particle, micelle, or liposome encapsulates an agent. The agent to be delivered by the particle, micelle, or liposome may be in the form of a gas, liquid, or solid. The compositions may further include or be combined with polymers (synthetic or natural), surfactants, cholesterol, carbohydrates, proteins, lipids, lipidoids, etc. to form the particles. These particles may be further combined with an excipient to form the compositions. The particles, micelles, and liposomes are described in more detail herein.

The compositions described herein (e.g., pharmaceutical compositions) can be prepared by any method known in the art (e.g., pharmacologically). In general, such preparatory methods include the steps of bringing a compound into association with an agent described herein (i.e., the "active ingredient"), optionally with a carrier or excipient, and/or one or more other accessory ingredients, and then, if necessary and/or desirable, shaping, and/or packaging the product into a desired single- or multi-dose unit.

Compositions can be prepared, packaged, and/or sold in bulk, as a single unit dose, and/or as a plurality of single unit doses. As used herein, a "unit dose" is a discrete amount of the composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the excipient (e.g., the pharmaceutically or cosmetically acceptable excipient), and/or any additional ingredients in a composition will vary, depending upon the identity, size, and/or condition of the subject treated and further depending upon the route by which the composition is to be administered. The composition may comprise between 0.1% and 100% (w/w) active ingredient.

Excipients used in the manufacture of provided compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Additionally, the composition may further comprise an apolipoprotein. Previous studies have reported that Apolipoprotein E (ApoE) was able to enhance cell uptake and gene silencing for a certain type of materials. See, e.g., Akinc, A. et al., Targeted delivery of RNAi therapeutics with endogenous and exogenous ligand-based mechanisms. Mol Ther. 18(7): p. 1357-64. In certain embodiments, the apolipoprotein is ApoA, ApoB, ApoC, ApoE, or ApoH, or an isoform thereof.

Liquid dosage forms for oral and parenteral administration include emulsions, microemulsions, solutions, suspensions, syrups and elixirs. In certain embodiments, the emulsions, microemulsions, solutions, suspensions, syrups and elixirs are or cosmetically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, solubilizing agents such as Cremophor®, alcohols, oils, modified oils, glycols, polysorbates, cyclodextrins, polymers, and mixtures thereof, are used.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of the active ingredient, it is often desirable to slow its absorption from subcutaneous or intramuscular injection. This can be accomplished by the use of a liquid suspension of crystalline or amorphous material with poor water solubility. The rate of absorption of the active ingredient then depends upon its rate of dissolution, which, in turn, may depend upon crystal size and crystalline form. Alternatively, delayed absorption of a parenterally administered active ingredient may be accomplished by dissolving or suspending the composition in an oil vehicle.

Compositions for rectal or vaginal administration are typically suppositories which can be prepared with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the composition is mixed with at least one inert, excipient or carrier (e.g., pharmaceutically or cosmetically acceptable excipient or carrier) such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents that may release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The composition can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the formulation art. In such solid dosage forms the composition can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner.

Dosage forms for topical and/or transdermal administration of a composition may include ointments, pastes, creams, lotions, gels, powders, solutions, sprays, inhalants, and/or patches. Generally, the composition is admixed under sterile conditions with a carrier or excipient and/or any needed preservatives and/or buffers as can be required. Additionally, the use of transdermal patches is contemplated, which often have the added advantage of providing controlled delivery of an active ingredient to the body. Such dosage forms can be prepared, for example, by dispersing the composition in the proper medium. Alternatively or additionally, the rate can be controlled by either providing a rate controlling membrane and/or by dispersing the composition in a polymer matrix and/or gel.

Suitable devices for use in delivering intradermal compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Alternatively or additionally, conventional syringes can be used in the classical mantoux method of intradermal administration. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599, 302; 5,334,144; 5,993,412; 5,649,912; 5,569,189; 5,704, 911; 5,383,851; 5,893,397; 5,466,220; 5,339,163; 5,312, 335; 5,503,627; 5,064,413; 5,520,639; 4,596,556; 4,790, 824; 4,941,880; 4,940,460; and PCT publications WO 97/37705 and WO 97/13537. Ballistic powder/particle delivery devices which use compressed gas to accelerate the agent in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A composition can be prepared, packaged, and/or sold in a formulation suitable for pulmonary administration via the buccal cavity. Such a formulation may comprise dry particles which comprise the composition and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Compositions formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a composition. Another formulation suitable for intranasal administration is a coarse powder comprising the composition and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein.

A composition can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A composition can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this invention.

Although the descriptions of compositions provided herein are principally directed to compositions which are suitable for administration to humans, it will be understood by the skilled artisan that such compositions are generally suitable for administration to animals of all sorts. Modification of compositions suitable for administration to humans in order to render the compositions suitable for administration to various animals is well understood, and the ordinarily skilled veterinary pharmacologist can design and/or perform such modification with ordinary experimentation.

Compositions provided herein are typically formulated in dosage unit form for ease of administration and uniformity of dosage. It will be understood, however, that the total daily usage of the compositions will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of an agent required to achieve an effective amount will vary from subject to subject, depending, for example, on species, age, and general condition of a subject, severity of the side effects or disorder, identity of the particular agent, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of an agent for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of an agent per unit dosage form.

In certain embodiments, the agents described herein may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that dose ranges as described herein provide guidance for the administration of provided compositions to an adult. The amount to be administered to, for example, a child or an adolescent can be determined by a medical practitioner or person skilled in the art and can be lower or the same as that administered to an adult.

Compositions described herein may further include a hydrophilic polymer (e.g., polyethylene glycol (PEG)). The compositions described herein may further include a lipid (e.g., a steroid, a substituted or unsubstituted cholesterol, or a polyethylene glycol (PEG)-containing material). In certain embodiments, the lipid included in the compositions is a triglyceride, a diglyceride, a PEGylated lipid, a phospholipid (e.g., 1,2-distearoyl-sn-glycero-3-phosphocholine (DSPC)), a steroid, a substituted or unsubstituted cholesterol, an apolipoprotein, or a combination thereof. In certain embodiments, the compositions include two components selected from the group consisting of the following components: a hydrophilic polymer, a triglyceride, a diglyceride, a PEGylated lipid, a phospholipid, a steroid, a substituted or unsubstituted cholesterol, and an apolipoprotein. In certain embodiments, the compositions include three components selected from the group consisting of the following components: a hydrophilic polymer, a triglyceride, a diglyceride, a PEGylated lipid, a phospholipid, a steroid, a substituted or unsubstituted cholesterol, and an apolipoprotein. In certain embodiments, the compositions include at least four components selected from the group consisting of the following components: a hydrophilic polymer, a triglyceride, a diglyceride, a PEGylated lipid, a phospholipid, a steroid, a substituted or unsubstituted cholesterol, and an apolipoprotein. In certain embodiments, the compositions include a hydrophilic polymer, a phospholipid, a steroid, and a substituted or unsubstituted cholesterol. In certain embodiments, the compositions include PEG, DSPC, and substituted or unsubstituted cholesterol.

The compositions may include cholesterol, a lipid (e.g., a PEGylated lipid, a phospholipid, a cholesterol lipid), and a apolipoprotein, in addition to a compound of Formula (I) and an agent described herein.

Exemplary phospholipids include, but are not limited to, 1,2-distearoyl-sn-glycero-3-phosphocholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, and 18-1-trans PE, 1-stearoyl-2-oleoyl-phosphatidyethanolamine (SOPE).

Exemplary cholesterol lipids include, but are not limited to, PEGylated cholesterol, and DC-Chol (N,N-dimethyl-N-ethylcarboxamidocholesterol).

Exemplary PEGylated lipids include, but are not limited to, PEGylated cholesterol, 1,2-dimyristoyl-sn-glycero-3-phosphoethanolamine-N-[methoxy(polyethyleneglycol)-2000] (C14-PEG 2000, Avanti), N-Octanoyl-Sphingosine-1-[Succinyl(Methoxy Polyethylene Glycol)-2000], and dimyristoylglycerol (DMG)-PEG-2K. In some embodiments, the one or more PEGylated lipids comprise a poly (ethylene) glycol chain of up to 5 kDa in length covalently attached to a lipid with alkyl chain(s) of $C_6$-$C_{20}$ length.

In certain embodiments, the compositions include two or more components selected from the group consisting of the following components: a PEGylated lipid, a phospholipid, cholesterol, a cholesterol lipid, and a apolipoprotein. In certain embodiments, the compositions include a phospholipid, cholesterol, and a PEGylated lipid. In certain embodiments, the compositions include 1,2-distearoyl-sn-glycero-3-phosphocholine (DSPC), cholesterol, and C14-PEG-2000.

Compositions described herein may be useful in other applications, e.g., non-medical applications. Nutraceutical compositions described herein may be useful in the delivery of an effective amount of a nutraceutical, e.g., a dietary supplement, to a subject in need thereof. Cosmetic compositions described herein may be formulated as a cream, ointment, balm, paste, film, or liquid, etc., and may be useful in the application of make-up, hair products, and materials useful for personal hygiene, etc. Compositions described herein may be useful for other non-medical applications, e.g., such as an emulsion, emulsifier, or coating, useful, for example, as a food component, for extinguishing fires, for disinfecting surfaces, for oil cleanup, and/or as a bulk material.

Agents

Agents that are delivered by the systems (e.g., pharmaceutical compositions) described herein may be (e.g., therapeutic or prophylactic), diagnostic, cosmetic, or nutraceutical agents. Any chemical compound to be administered to a subject may be delivered using the complexes, picoparticles, nanoparticles, microparticles, micelles, or liposomes, described herein. The agent may be an organic molecule, inorganic molecule, nucleic acid, protein, peptide, polynucleotide, targeting agent, an isotopically labeled chemical compound, vaccine, an immunological agent, or an agent useful in bioprocessing (e.g., intracellular manufacturing of proteins, such as a cell's bioprocessing of a commercially useful chemical or fuel). For example, intracellular delivery of an agent may be useful in bioprocessing by maintaining the cell's health and/or growth, e.g., in the manufacturing of proteins. Any chemical compound to be administered to a subject or contacted with a cell may be delivered to the subject or cell using the compositions.

Exemplary agents that may be included in a composition described herein include, but are not limited to, small molecules, organometallic compounds, polynucleotides, proteins, peptides, carbohydrates, monosaccharides, oligosaccharides, polysaccharides, nucleoproteins, mucoproteins, lipoproteins, small molecules linked to proteins, glycoproteins, steroids, nucleotides, oligonucleotides, polynucleotides, nucleosides, antisense oligonucleotides, lipids, hormones, vitamins, cells, metals, targeting agents, isotopically labeled chemical compounds, drugs (e.g., compounds approved for human or veterinary use by the U.S. Food and Drug Administration as provided in the Code of Federal Regulations), vaccines, immunological agents, agents useful in bioprocessing, and mixtures thereof. The targeting agents are described in more detail herein. In certain embodiments, the agents are nutraceutical agents. In certain embodiments, the agents are pharmaceutical agents (e.g., a therapeutic or prophylactic agent). In certain embodiments, the agent is an antibiotic agent (e.g., an anti-bacterial, anti-viral, or anti-fungal agent), anesthetic, steroidal agent, anti-proliferative agent, anti-inflammatory agent, anti-angiogenesis agent, anti-neoplastic agent, anti-cancer agent, anti-diabetic agent, antigen, vaccine, antibody, decongestant, antihypertensive, sedative, birth control agent, progestational agent, anti-cholinergic, analgesic, immunosuppressant, anti-depressant, anti-psychotic, β-adrenergic blocking agent, diuretic, cardiovascular active agent, vasoactive agent, non-steroidal, nutritional agent, anti-allergic agent, or pain-relieving agent. Vaccines may comprise isolated proteins or peptides, inactivated organisms and viruses, dead organisms and viruses, genetically altered organisms or viruses, and cell extracts. Therapeutic and prophylactic agents may be combined with interleukins, interferon, cytokines, and adjuvants such as cholera toxin, alum, and Freund's adjuvant, etc.

In certain embodiments, an agent to be delivered or used in a composition described herein is a polynucleotide. In certain embodiments, the agent is plasmid DNA (pDNA). In certain embodiments, the agent is single-stranded DNA (ssDNA), double-stranded DNA (dsDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, or viral DNA. In certain embodiments, the agent is RNA. In certain embodiments, the agent is small interfering RNA (siRNA). In certain embodiments, the agent is messenger RNA (mRNA). In certain embodiments, the agent is single-stranded RNA (ssRNA), double-stranded RNA (dsRNA), small interfering RNA (siRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, or viral satellite RNA. In certain embodiments, the agent is an RNA that carries out RNA interference (RNAi). The phenomenon of RNAi is discussed in greater detail, for example, in the following references: Elbashir et al., 2001, *Genes Dev.*, 15:188; Fire et al., 1998, *Nature*, 391:806; Tabara et al., 1999, Cell, 99:123; Hammond et al., *Nature*, 2000, 404:293; Zamore et al., 2000, *Cell*, 101:25; Chakraborty, 2007, *Curr. Drug Targets*, 8:469; and Morris and Rossi, 2006, *Gene Ther.*, 13:553. In certain embodiments, upon delivery of an RNA into a subject, tissue, or cell, the RNA is able to interfere with the expression of a specific gene in the subject, tissue, or cell. In certain embodiments, the agent is a pDNA, siRNA, mRNA, or a combination thereof.

In certain embodiments, the polynucleotide may be provided as an antisense agent or RNAi. See, e.g., Fire et al., *Nature* 391:806-811, 1998. Antisense therapy is meant to include, e.g., administration or in situ provision of single- or double-stranded polynucleotides, or derivatives thereof, which specifically hybridize, e.g., bind, under cellular conditions, with cellular mRNA and/or genomic DNA, or mutants thereof, so as to inhibit the expression of the encoded protein, e.g., by inhibiting transcription and/or translation. See, e.g., Crooke, "Molecular mechanisms of action of antisense drugs," *Biochim. Biophys. Acta* 1489(1): 31-44, 1999; Crooke, "Evaluating the mechanism of action of anti-proliferative antisense drugs," *Antisense Nucleic Acid Drug Dev.* 10(2):123-126, discussion 127, 2000; *Methods in Enzymology* volumes 313-314, 1999. The binding may be by conventional base pair complementarity, or, for example, in the case of binding to DNA duplexes, through specific interactions in the major groove of the double helix (i.e., triple helix formation). See, e.g., Chan et al., *J. Mol. Med.* 75(4):267-282, 1997.

In some embodiments, pDNA, siRNA, dsRNA, shRNA, miRNA, mRNA, tRNA, asRNA, and/or RNAi can be designed and/or predicted using one or more of a large number of available algorithms. To give but a few examples, the following resources can be utilized to design and/or predict polynucleotides: algorithms found at Alnylum Online; Dharmacon Online; OligoEngine Online; Molecula Online; Ambion Online; BioPredsi Online; RNAi Web Online; Chang Bioscience Online; Invitrogen Online; LentiWeb Online GenScript Online; Protocol Online; Reynolds et al., 2004, *Nat. Biotechnol.*, 22:326; Naito et al., 2006, *Nucleic Acids Res.*, 34:W448; Li et al., 2007, *RNA*, 13:1765; Yiu et al., 2005, *Bioinformatics*, 21:144; and Jia et al., 2006, *BMC Bioinformatics*, 7: 271.

The polynucleotide included in a composition may be of any size or sequence, and they may be single- or double-stranded. In certain embodiments, the polynucleotide includes at least about 30, at least about 100, at least about 300, at least about 1,000, at least about 3,000, or at least about 10,000 base pairs. In certain embodiments, the polynucleotide includes less than about 10,000, less than about 3,000, less than about 1,000, less than about 300, less than about 100, or less than about 30 base pairs. Combinations of the above ranges (e.g., at least about 100 and less than about 1,000) are also within the scope of the invention. The polynucleotide may be provided by any means known in the art. In certain embodiments, the polynucleotide is engineered using recombinant techniques. See, e.g., Ausubel et al., *Current Protocols in Molecular Biology* (John Wiley & Sons, Inc., New York, 1999); *Molecular Cloning: A Laboratory Manual*, 2nd Ed., ed. by Sambrook, Fritsch, and Maniatis (Cold Spring Harbor Laboratory Press: 1989). The polynucleotide may also be obtained from natural sources and purified from contaminating components found normally in nature. The polynucleotide may also be chemically synthesized in a laboratory. In certain embodiments, the polynucleotide is synthesized using standard solid phase chemistry. The polynucleotide may be isolated and/or purified. In certain embodiments, the polynucleotide is substantially free of impurities. In certain embodiments, the polynucleotide is at least about 50%, at least about 60%, at least about 70%, at least about 80%, at least about 90%, at least about 95%, or at least about 99% free of impurities.

The polynucleotide may be modified by physical, chemical, and/or biological means. The modifications include methylation, phosphorylation, and end-capping, etc. In certain embodiments, the modifications lead to increased stability of the polynucleotide.

Wherever a polynucleotide is employed in the composition, a derivative of the polynucleotide may also be used. These derivatives include products resulted from modifications of the polynucleotide in the base moieties, sugar moieties, and/or phosphate moieties of the polynucleotide. Modified base moieties include, but are not limited to, 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, and 2-thiocytidine. Modified sugar moieties include, but are not limited to, 2'-fluororibose, ribose, 2'-deoxyribose, 3'-azido-2',3'-dideoxyribose, 2',3'-dideoxyribose, arabinose (the 2'-epimer of ribose), acyclic sugars, and hexoses. The nucleosides may be strung together by linkages other than the phosphodiester linkage found in naturally occurring DNA and RNA. Modified linkages include, but are not limited to, phosphorothioate and 5'-N-phosphoramidite linkages. Combinations of the various modifications may be used in a single polynucleotide. These modified polynucleotides may be provided by any means known in the art; however, as will be appreciated by those of skill in the art, the modified polynucleotides may be prepared using synthetic chemistry in vitro.

The polynucleotide described herein may be in any form, such as a circular plasmid, a linearized plasmid, a cosmid, a viral genome, a modified viral genome, and an artificial chromosome.

The polynucleotide described herein may be of any sequence. In certain embodiments, the polynucleotide encodes a protein or peptide. The encoded protein may be an enzyme, structural protein, receptor, soluble receptor, ion channel, active (e.g., pharmaceutically active) protein, cytokine, interleukin, antibody, antibody fragment, antigen, coagulation factor, albumin, growth factor, hormone, and insulin, etc. The polynucleotide may also comprise regulatory regions to control the expression of a gene. These regulatory regions may include, but are not limited to, promoters, enhancer elements, repressor elements, TATA boxes, ribosomal binding sites, and stop sites for transcription, etc. In certain embodiments, the polynucleotide is not intended to encode a protein. For example, the polynucleotide may be used to fix an error in the genome of the cell being transfected.

In certain embodiments, the polynucleotide described herein comprises a sequence encoding an antigenic peptide or protein. A composition containing the polynucleotide can be delivered to a subject to induce an immunologic response sufficient to decrease the chance of a subsequent infection and/or lessen the symptoms associated with such an infection. The polynucleotide of these vaccines may be combined with interleukins, interferon, cytokines, and/or adjuvants described herein.

The antigenic protein or peptides encoded by the polynucleotide may be derived from bacterial organisms, such as *Streptococccus pneumoniae, Haemophilus influenzae, Staphylococcus aureus, Streptococcus pyrogenes, Corynebacterium diphtheriae, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi*, and *Camphylobacter jejuni*; from viruses, such as smallpox virus, influenza A virus, influenza B virus, respiratory syncytial virus, parainfluenza virus, measles virus, HIV virus, varicella-zoster virus, herpes simplex 1 virus, herpes simplex 2 virus, cytomegalovirus, Epstein-Barr virus, rotavirus, rhinovirus, adenovirus, papillomavirus, poliovirus, mumps virus, rabies virus, rubella virus, coxsackieviruses, equine encephalitis virus, Japanese encephalitis virus, yellow fever virus, Rift Valley fever virus, hepatitis A virus, hepatitis B virus, hepatitis C virus, hepatitis D virus, and hepatitis E virus; and from fungal, protozoan, or parasitic organisms, such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis*, and *Schistosoma mansoni*.

In certain embodiments, the agent is erythropoietin (EPO), e.g., recombinant human erythropoietin (rhEPO). Erythropoietin is an essential hormone for red blood cell production, and may be used in treating hematological diseases, e.g., anemia., such as anemia resulting from chronic kidney disease, chemotherapy induced anemia in patients with cancer, inflammatory bowel disease (Crohn's disease and ulcerative colitis) and myelodysplasia from the treatment of cancer (chemotherapy and radiation). Recombinant human erythropoietins available for use include EPOGEN/PROCRIT (Epoetin alfa, rINN) and ARANESP (Darbepoetin alfa, rINN).

An agent described herein may be non-covalently (e.g., complexed or encapsulated) attached to a compound as described herein, or included in a composition described herein. In certain embodiments, upon delivery of the agent into a cell, the agent is able to interfere with the expression of a specific gene in the cell.

In certain embodiments, the agent in a composition that is delivered to a subject in need thereof may be a mixture of two or more agents that may be useful as, e.g., combination therapies. The compositions including the two or more agents can be administered to achieve a synergistic effect. In certain embodiments, the compositions including the two or more agents can be administered to improve the activity and/or bioavailability, reduce and/or modify the metabolism, inhibit the excretion, and/or modify the distribution within the body of a subject, of each one of the two or more agents.

It will also be appreciated that the therapy employed may achieve a desired effect for the same disorder, and/or it may achieve different effects.

The compositions (e.g., pharmaceutical compositions) can be administered concurrently with, prior to, or subsequent to the one or more agents (e.g., pharmaceutical agents). The two or more agents may be useful for treating and/or preventing a same disease or different diseases described herein. Each one of the agents may be administered at a dose and/or on a time schedule determined for that agent. The agents may also be administered together with each other and/or with the composition described herein in a single dose or administered separately in different doses. The particular combination to employ in a regimen will take into account compatibility of the agents and/or the desired therapeutic and/or prophylactic effect to be achieved. In general, it is expected that the agents utilized in combination be utilized at levels that do not exceed the levels at which they are utilized individually. In some embodiments, the levels utilized in combination will be lower than those utilized individually.

Targeting Agents

Since it is often desirable to target a particular cell, collection of cells, or tissue, compounds of Formula (I), and the complexes, liposomes, micelles, and particles (e.g., microparticles and nanoparticles) thereof, may be modified to include targeting moieties. For example, a compound of Formula (I) may include a targeting moiety. A variety of agents or regions that target particular cells are known in the art. See, e.g., Cotten et al., *Methods Enzym.* 217:618, 1993. The targeting agent may be included throughout a particle of a compound of Formula (I) or may be only on the surface of the particle. The targeting agent may be a protein, peptide, carbohydrate, glycoprotein, lipid, small molecule, or polynucleotide, etc. The targeting agent may be used to target specific cells or tissues or may be used to promote endocytosis or phagocytosis of the particle. Examples of targeting agents include, but are not limited to, antibodies, fragments of antibodies, proteins, peptides, carbohydrates, receptor ligands, sialic acid, and aptamers, etc. If the targeting agent is included throughout a particle, the targeting agent may be included in the mixture that is used to form the particle. If the targeting agent is only on the surface of a particle, the targeting agent may be associated with (e.g., by covalent or non-covalent (e.g., electrostatic, hydrophobic, hydrogen bonding, van der Waals, π-π stacking) interactions) the formed particle using standard chemical techniques.

Complexes of an Agent and a Compound of Formula (I)

It is contemplated that the compounds of Formula (I) are useful in the delivery of one or more agents (such as a polynucleotide (e.g., DNA (e.g., pDNA) or RNA (e.g., siRNA, mRNA), synthetic analogs of DNA and/or RNA, and DNA/RNA hybrids, etc.)) to a subject in need thereof. Without wishing to be bound by any particular theory, the compounds of Formula (I) have several desirable properties that make a composition comprising the compound and an agent suitable for delivering the agent to a subject in need thereof. The desirable properties include: 1) the ability of the compound to complex with and "protect" the agent that may otherwise be labile; 2) the ability of the compound to buffer the pH in an endosome of a cell of the subject; 3) the ability of the compound to act as a "proton sponge" and cause endosomolysis; and 4) the ability of the compound to substantially neutralize the negative charges of the agent.

A compound of Formula (I) and an agent may form a complex in a composition as described herein. For example, a compound of Formula (I) comprises secondary and tertiary amino moieties, which may be useful in enhancing the ability of an inventive composition including an agent (such as a polynucleotide) to deliver the agent to a subject (e.g., into a cell of the subject) in need thereof. The amino moieties, sterically hindered or not, may non-covalently interact with a polynucleotide. A polynucleotide may be contacted with a compound of Formula (I) under conditions suitable to form a complex. In certain embodiments, the polynucleotide binds to a compound of Formula (I) to form a complex through one or more non-covalent interactions described herein. In certain embodiments, the polynucleotide binds to a compound of Formula (I) to form a complex through electrostatic interactions. Without wishing to be bound by any particular theory, one or more amino moieties of a compound of Formula (I) may be positively charged, and the polynucleotide (e.g., the monophosphate, diphosphate, and/or triphosphate moieties of the polynucleotide) may be negatively charged, when a compound of Formula (I), or a composition thereof, is delivered to a subject in need thereof (e.g., when the compound, or a composition thereof, is delivered to the subject at the physiological pH). The polynucleotide may bind to a compound of Formula (I) to form a complex through electrostatic interactions between the negative charges of the inventive compound and the positive charges of the polynucleotide. By substantially neutralizing the charges (e.g., negative charges) of the polynucleotide, the resulting complex may be able to more easily pass through the hydrophobic membranes (e.g., cytoplasmic, lysosomal, endosomal, nuclear) of a cell, compared to a polynucleotide whose charges are not neutralized. In certain embodiments, the complex is substantially neutral. In certain embodiments, the complex is slightly positively charged. In certain embodiments, the complex has a positive ζ-potential. In certain embodiments the ζ-potential is between 0 and +30. In certain embodiments, upon delivery of the agent into a cell of a subject in need thereof, the agent is able to interfere with the expression of a specific gene in the cell.

The compound of Formula (I) includes alkenyl moieties on the amino moieties. The alkenyl $R^L$ moieties may be hydrophobic and may be useful in enhancing the ability of a composition comprising an agent (such as a polynucleotide) to deliver the agent to a subject (e.g., into a cell of the subject) in need thereof. As used herein, the term "hydrophobic" refers to the ability of the alkenyl $R^L$ to dissolve or assist in dissolving in fats, oils, lipids, and/or non-polar solvents (e.g., hexane or toluene). For example, hydrophobic alkenyl moieties may assist a complex of a compound of Formula (I) and a polynucleotide to more easily pass through cell membranes, which are also hydrophobic, compared to a polynucleotide, which is typically hydrophilic.

Polynucleotides may be degraded chemically and/or enzymatically (e.g., by nucleases and nucleotidases). The interaction of compound of Formula (I) with the polynucleotide is thought to at least partially prevent the degradation of the polynucleotide.

A compound of Formula (I) may be at least partially provided as a salt (e.g., being protonated) so as to form a complex with a negatively charged agent (e.g., a polynucleotide). In certain embodiments, the complex form particles that are useful in the delivery of the agent to a subject. In certain embodiments, more than one compound of Formula (I) may be associated with an agent. For example, the complex may include 1-10, 1-100, 1-1,000, 10-1,000, 100-1,000, or 100-10,000 compounds associated with an agent.

The ratio of the amount of a compound of Formula (I) to the amount of an agent (e.g., a polynucleotide) in an composition including the compound and agent (e.g., as a complex) may be adjusted so that the agent may be more efficiently delivered to a subject in need thereof and/or the toxicity of the composition is decreased. In certain embodiments, the ratio of the compound of Formula (I), or salt thereof, to the agent is at least about 1:1, at least about 2:1, at least about 5:1, at least about 10:1, at least about 20:1, at least about 50:1, at least about 100:1, at least about 200:1, or at least about 500:1 mol/mol. In certain embodiments, the ratio of the compound of Formula (I), or salt thereof, to the agent is less than about 500:1, less than about 200:1, less than about 100:1, less than about 50:1, less than about 20:1, less than about 10:1, less than about 5:1, less than about 2:1, or less than about 1:1 mol/mol. Combinations of the above ranges (e.g., at least about 10:1 and less than about 100:1) are also within the scope of the invention.

The ratio of the amount of the amino moieties of a compound of Formula (I) to the amount of the phosphate moieties of a polynucleotide (i.e., nitrogen:phosphate ratio) in a composition including the compound and polynucleotide (e.g., as a complex) may also be adjusted so that the polynucleotide may be more efficiently delivered to a subject in need thereof and/or the toxicity of the composition is decreased. See, e.g., Incani et al., *Soft Matter* (2010) 6:2124-2138. In certain embodiments, the nitrogen:phosphate ratio is at least about 1:1, at least about 2:1, at least about 5:1, at least about 10:1, at least about 20:1, at least about 50:1, at least about 100:1, at least about 200:1, or at least about 500:1 mol/mol. In certain embodiments, the nitrogen:phosphate ratio is less than about 500:1, less than about 200:1, less than about 100:1, less than about 50:1, less than about 20:1, less than about 10:1, less than about 5:1, less than about 2:1, or less than about 1:1 mol/mol. Combinations of the above ranges (e.g., at least about 10:1 and less than about 100:1) are also within the scope of the invention.

Particles

A composition including a compound of Formula (I) and an agent may be in the form of a particle. In certain embodiments, the compound of Formula (I) and agent form a complex, and the complex is in the form of a particle. In certain embodiments, the compound of Formula (I) encapsulates the agent and is in the form of a particle. In certain embodiments, the compound of Formula (I) is mixed with the agent, and the mixture is in the form of a particle.

In certain embodiments, a complex of a compound of Formula (I) and an agent in a composition of is in the form of a particle. In certain embodiments, the particle is a microparticle (i.e., particle having a characteristic dimension of less than about 1 millimeter and at least about 1 micrometer, where the characteristic dimension of the particle is the smallest cross-sectional dimension of the particle. In certain embodiments, the particle is a nanoparticle (i.e., a particle having a characteristic dimension of less than about 1 micrometer and at least about 1 nanometer, where the characteristic dimension of the particle is the smallest cross-sectional dimension of the particle). In certain embodiments, the average diameter of the particle is at least about 10 nm, at least about 30 nm, at least about 100 nm, at least about 300 nm, at least about 1 μm, at least about 3 μm, at least about 10 μm, at least about 30 μm, at least about 100 μm, at least about 300 μm, or at least about 1 mm. In certain embodiments, the average diameter of the particle is less than about 1 mm, less than about 300 μm, less than about 100 μm, less than about 30 μm less than about 10 μm, less than about 3 μm, less than about 1 μm, less than about 300 nm, less than about 100 nm, less than about 30 nm, or less than about 10 nm. Combinations of the above ranges (e.g., at least about 100 nm and less than about 1 µm) are also within the scope of the present invention.

The particles described herein may include additional materials such as polymers (e.g., synthetic polymers (e.g., PEG, PLGA) and natural polymers (e.g., phospholipids)). In certain embodiments, the additional materials are approved by a regulatory agency, such as the U.S. FDA, for human and veterinary use.

The particles may be prepared using any method known in the art, such as precipitation, milling, spray drying, single and double emulsion solvent evaporation, solvent extraction, phase separation, and simple and complex coacervation. In certain embodiments, methods of preparing the particles are the double emulsion process and spray drying. The conditions used in preparing the particles may be altered to yield particles of a desired size or property (e.g., hydrophobicity, hydrophilicity, external morphology, "stickiness", shape, polydispersity, etc.). The method of preparing the particle and the conditions (e.g., solvent, temperature, concentration, and air flow rate, etc.) used may also depend on the agent being complexed, encapsulated, or mixed, and/or the composition of the matrix.

Methods developed for making particles for delivery of agents that are included in the particles are described in the literature. See, e.g., Doubrow, M., Ed., "Microcapsules and Nanoparticles in Medicine and Pharmacy," CRC Press, Boca Raton, 1992; Mathiowitz and Langer, *J. Controlled Release* 5:13-22, 1987; Mathiowitz et al., *Reactive Polymers* 6:275-283, 1987; Mathiowitz et al., *J. Appl. Polymer Sci.* 35:755-774, 1988.

If the particles prepared by any of the above methods have a size range outside of the desired range, the particles can be sized, for example, using a sieve. The particles may also be coated. In certain embodiments, the particles are coated with a targeting agent. In certain embodiments, the particles are coated with a surface-altering agent. In some embodiments, the particles are coated to achieve desirable surface properties (e.g., a particular charge).

In certain embodiments, the polydispersity index (PDI, determined by dynamic light scattering) of the particles described herein (e.g., particles included in a composition described herein) is between 0.01 and 0.9, between 0.1 and 0.9, between 0.1 and 0.7, between 0.1 and 0.5, between 0.01 and 0.4, between 0.03 and 0.4, between 0.1 and 0.4, between 0.01 and 0.3, between 0.03 and 0.3, or between 0.1 and 0.3.

Micelles and Liposomes

A composition including a compound of Formula (I) and an agent may be in the form of a micelle or liposome. In certain embodiments, the compound of Formula (I) is in the form of a micelle or liposome. In certain embodiments, the agent is in the form of a micelle or liposome. In certain embodiments, the compound of Formula (I) and agent form a complex, and the complex is in the form of a micelle or liposome. In certain embodiments, the compound of Formula (I) encapsulates the agent and is in the form of a micelle or liposome. In certain embodiments, the compound of Formula (I) is mixed with the agent, and the mixture is in the form of a micelle or liposome. Micelles and liposomes are particularly useful in delivering an agent, such as a hydrophobic agent. When the micelle or liposome is complexed with (e.g., encapsulates or covers) a polynucleotide, the resulting complex may be referred to as a "lipoplex." Many techniques for preparing micelles and liposomes are known in the art, and any such method may be used herein to make micelles and liposomes.

In certain embodiments, liposomes are formed through spontaneous assembly. In some embodiments, liposomes are formed when thin lipid films or lipid cakes are hydrated and stacks of lipid crystalline bilayers become fluid and swell. The hydrated lipid sheets detach during agitation and self-close to form large, multilamellar vesicles (LMV). This prevents interaction of water with the hydrocarbon core of the bilayers at the edges. Once these liposomes have formed, reducing the size of the liposomes can be modified through input of sonic energy (sonication) or mechanical energy (extrusion). See, e.g., Walde, P. "Preparation of Vesicles (Liposomes)" In *Encylopedia of Nanoscience and Nanotechnology*; Nalwa, H. S. Ed. American Scientific Publishers: Los Angeles, 2004; Vol. 9, pp. 43-79; Szoka et al., "Comparative Properties and Methods of Preparation of Lipid Vesicles (Liposomes)" *Ann. Rev. Biophys. Bioeng.* 9:467-508, 1980; each of which is incorporated herein by reference. The preparation of lipsomes may involve preparing a compound of Formula (I) for hydration, hydrating the compound with agitation, and sizing the vesicles to achieve a homogenous distribution of liposomes. A compound of Formula (I) may be first dissolved in an organic solvent in a container to result in a homogeneous mixture. The organic solvent is then removed to form a polymer-derived film. This polymer-derived film is thoroughly dried to remove residual organic solvent by placing the container on a vacuum pump for a period of time. Hydration of the polymer-derived film is accomplished by adding an aqueous medium and agitating the mixture. Disruption of LMV suspensions using sonic energy typically produces small unilamellar vesicles (SUV) with diameters in the range of 15-50 nm. Lipid extrusion is a technique in which a lipid/polymer suspension is forced through a polycarbonate filter with a defined pore size to yield particles having a diameter near the pore size of the filter used. Extrusion through filters with 100 nm pores typically yields large, unilamellar polymer-derived vesicles (LUV) with a mean diameter of 120-140 nm. In certain embodiments, the amount of a compound of Formula (I) in the liposome ranges from about 30 mol % to about 80 mol %, from about 40 mol % to about 70 mol %, or from about 60 mol % to about 70 mol %. In certain embodiments, the compound of Formula (I) employed further complexes an agent, such as a polynucleotide. In such embodiments, the application of the liposome is the delivery of the polynucleotide.

The following scientific papers described other methods for preparing liposomes and micelles: Narang et al., "Cationic Lipids with Increased DNA Binding Affinity for Non-viral Gene Transfer in Dividing and Nondividing Cells," *Bioconjugate Chem.* 16:156-68, 2005; Hofland et al., "Formation of stable cationic lipid/DNA complexes for gene transfer," *Proc. Natl. Acad. Sci. USA* 93:7305-7309, July 1996; Byk et al., "Synthesis, Activity, and Structure—Activity Relationship Studies of Novel Cationic Lipids for DNA Transfer," *J. Med. Chem.* 41(2):224-235, 1998; Wu et al., "Cationic Lipid Polymerization as a Novel Approach for Constructing New DNA Delivery Agents," *Bioconjugate Chem.* 12:251-57, 2001; Lukyanov et al., "Micelles from lipid derivatives of water-soluble polymers as delivery systems for poorly soluble drugs," *Advanced Drug Delivery Reviews* 56:1273-1289, 2004; Tranchant et al., "Physicochemical optimisation of plasmid delivery by cationic lipids," *J. Gene Med.* 6:S24-S35, 2004; van Balen et al., "Liposome/Water Lipophilicity: Methods, Information Content, and Pharmaceutical Applications," *Medicinal Research Rev.* 24(3):299-324, 2004.

Kits

Also contemplated herein are kits (e.g., packs). The kits provided may comprise a composition as described herein and a container (e.g., a vial, ampule, bottle, syringe, and/or dispenser package, or other suitable container). In some embodiments, provided kits may optionally further include a second container comprising an excipient for dilution or suspension of the composition. In some embodiments, the composition provided in the first container and the composition provided in the second container are combined to form one unit dosage form. In certain embodiments, the kits further include instructions for administering the composition. The kits may also include information as required by a regulatory agency such as the U.S. Food and Drug Administration (FDA). In certain embodiments, the information included in the kits is prescribing information. In certain embodiments, the kits, including the instructions, provide for treating and/or preventing a disease described herein. The kit may include one or more agents described herein as a separate composition.

Methods of Treatment and Uses

It is estimated that over 10,000 human diseases are caused by genetic disorders, which are abnormalities in genes or chromosomes. See, e.g., McClellan, J. and M. C. King, *Genetic heterogeneity in human disease*. Cell. 141(2): p. 210-7; Leachman, S. A. et al., *J. Dermatol. Sci.*, 2008. 51(3): p. 151-7. Many of these diseases are fatal, such as cancer, severe hypercholesterolemia, and familial amyloidotic polyneuropathy. See, e.g., Frank-Kamenetsky, M. et al., *Proc. Natl. Acad. Sci. U.S.A.* 2008. 105(33): p. 11915-20; Coelho, T., *Curr. Opin. Neurol.*, 1996. 9(5): p. 355-9. Since the discovery of gene expression silencing via RNA interference (RNAi) by Fire and Mello (Fire, A. et al., *Nature,* 1998. 391(6669): p. 806-11), there has been extensive effort toward developing therapeutic applications for RNAi in humans. See, e.g., Davis, M. E., *Mol. Pharm.* 2009. 6(3): p. 659-68; Whitehead, K. A., R. Langer, and D. G. Anderson, *Nat. Rev. Drug Discovery,* 2009. 8(2): p. 129-138; Tan, S. J. et al., *Small.* 7(7): p. 841-56; Castanotto, D. and J. J. Rossi, *Nature,* 2009. 457(7228): p. 426-33; Chen, Y. and L. Huang, *Expert Opin. Drug Deliv.* 2008. 5(12): p. 1301-11; Weinstein, S. and D. Peer, *Nanotechnology.* 21(23): p. 232001; Fenske, D. B. and P. R. Cullis, *Expert Opin. Drug Deliv.* 2008. 5(1): p. 25-44; and Thiel, K. W. and P. H. Giangrande, *Oligonucleotides,* 2009. 19(3): p. 209-22. Currently, there are more than 20 clinical trials ongoing or completed involving siRNA therapeutics, which have shown promising results for the treatment of various diseases. See, e.g., Burnett, J. C., J. J. Rossi, and K. Tiemann, *Biotechnol. J.* 6(9): p. 1130-46. However, the efficient and safe delivery of siRNA is still a key challenge in the development of siRNA therapeutics. See, e.g., Juliano, R. et al., *Mol. Pharm.* 2009. 6(3): p. 686-95.

In one aspect, provided are methods of delivering an agent to a subject in need thereof, or to a tissue or cell. In certain embodiments, provided are methods of delivering the agent to a target tissue to the subject. In certain embodiments, described herein are methods of selectively delivering the agent to a target tissue, compared to a non-target tissue. In certain embodiments, described herein are methods of selectively delivering the agent to a target cell, compared to a non-target cell.

In certain embodiments, provided are methods of delivering the agent to the liver of the subject. In certain embodiments, provided are methods of delivering the agent to the spleen of the subject. In certain embodiments, provided are methods of selectively delivering the agent to the the liver, lung, and/or spleen of the subject. In certain embodiments, provided are methods of delivering a polynucleotide to the subject or cell. In certain embodiments, provided are methods of delivering a DNA to the subject or cell. In certain embodiments, provided are methods of delivering a pDNA to the subject or cell. In certain embodiments, provided are methods of delivering an RNA to the subject or cell. In certain embodiments, provided are methods of delivering an siRNA to the subject or cell. In certain embodiments, provided are methods of delivering an mRNA to the subject or cell. In certain embodiments, the agent is delivered into a cell of the subject.

Another aspect relates to methods of increasing the delivery of an agent to a subject, tissue, or cell. In certain embodiments, the delivery of the agent to the subject, tissue, or cell is increased by a method described herein. In certain embodiments, the delivery of the agent to the subject, tissue, or cell by a method described herein is increased compared to the delivery of the agent to the subject, tissue, or cell by a control method that does not involve a a compound of Formula (I) as described herein.

In another aspect, provided are methods of treating and/or preventing a disease, e.g., a genetic disease, proliferative disease, hematological disease, neurological disease, liver disease, spleen disease, lung disease, painful condition, psychiatric disorder, musculoskeletal disease, a metabolic disorder, inflammatory disease, or autoimmune disease. In certain embodiments, the disease that is treated and/or prevented by the inventive methods is a genetic disease. In certain embodiments, the disease that is treated and/or prevented is cancer. In certain embodiments, the disease that is treated and/or prevented is a benign neoplasm. In certain embodiments, the disease that is treated and/or prevented by the inventive methods is pathological angiogenesis. In certain embodiments, the disease that is treated and/or prevented by the inventive methods is an inflammatory disease. In certain embodiments, the disease that is treated and/or prevented by the inventive methods is an autoimmune disease. In certain embodiments, the disease that is treated and/or prevented by the inventive methods is a hematological disease, e.g., anemia. In certain embodiments, the disease that is treated and/or prevented by the inventive methods is a neurological disease. In certain embodiments, the disease that is treated and/or prevented by the inventive methods is a liver disease. In certain embodiments, the disease that is treated and/or prevented by the inventive methods is a spleen disease. In certain embodiments, the disease that is treated and/or prevented by the inventive methods is a painful condition. In certain embodiments, the disease that is treated and/or prevented by the inventive methods is hepatic carcinoma. In certain embodiments, the disease that is treated and/or prevented by the inventive methods is hypercholesterolemia. In certain embodiments, the disease that is treated and/or prevented by the inventive methods is refractory anemia. In certain embodiments, the disease that is treated and/or prevented by the inventive methods is familial amyloid neuropathy. In certain embodiments, the disease that is treated and/or prevented by the inventive methods is hemophilia (e.g., hemophilia A or B).

In certain embodiments, the disease is a painful condition and, in certain embodiments, the composition further includes an analgesic agent. In certain embodiments, the painful condition is inflammatory pain. In certain embodiments, the painful condition (e.g., inflammatory pain) is associated with an inflammatory disorder and/or an autoimmune disorder.

Another aspect relates to methods of genetically engineering a subject. In certain embodiments, the subject is genetically engineered to increase the growth of the subject. In certain embodiments, the subject is genetically engineered to increase the subject's resistance to pathogenic organisms and/or microorganisms (e.g., viruses, bacteria, fungi, protozoa, and parasites). In certain embodiments, the subject is genetically engineered to increase the subject's ability to grow under unfavorable conditions (such as unfavorable weather conditions, e.g., dryness, infertility, and/or extremely cold or extremely high temperature).

In certain embodiments, the methods as described herein comprise administering to the subject a compound or composition as described herein. In certain embodiments, the methods as described herein comprise contacting the cell with a compound or composition as described herein. In certain embodiments, a method described herein includes contacting the tissue with a compound or composition as described herein.

In certain embodiments, the subject described herein is a human. In certain embodiments, the subject is an animal. The animal may be of either sex and may be at any stage of development. In certain embodiments, the subject is a fish. In certain embodiments, the subject is a mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal. In certain embodiments, the subject is a human with a disease described herein. In certain embodiments, the subject is a human suspected of having a disease described. In certain embodiments, the subject is a human at risk of developing a disease described herein. In certain embodiments, the subject is a plant.

In certain embodiments, the cell described herein is in vivo. In certain embodiments, the cell is in vitro. In certain embodiments, the cell is ex vitro.

In certain embodiments, the methods as described herein are in vivo methods. In certain embodiments, the methods as described herein are in vitro methods. In certain embodiments, the methods as described herein are ex vitro methods.

Another aspect relates to methods of screening a library of compounds to identify one or more compounds that are useful in the methods as described herein. In certain embodiments, the methods of screening a library of compounds are useful in identifying one or more compounds with desired or undesired properties. In certain embodiments, the desired property is solubility in water, solubility at different pH, ability to bind polynucleotides, ability to bind heparin, ability to bind small molecules, ability to bind protein, ability to form microparticles, ability to increase transfection efficiency, ability to support cell growth, ability to support cell attachment, ability to support tissue growth, and/or intracellular delivery of an agent described herein and/or an agent complexed or attached thereto to aid in bioprocessing. In certain embodiments, the undesired prosperity is the lack of a desired prosperity. In certain embodiments, the one or more compounds identified are useful for treating and/or preventing a disease described herein. In certain embodiments, the library of compounds is a library of compounds of Formula (I). In certain embodiments, the methods of screening a library include providing at least two different compounds compounds of Formula (I); and performing at least one assay using the different compounds of Formula (I), to identify one or more compounds that are useful in the methods as described herein.

Typically, the methods of screening a library of compounds involve at least one assay. In certain embodiments, the assay is performed to detect one or more characteristics associated with the treatment and/or prevention of a disease described herein. The characteristics may be desired (e.g., a disease being treated and/or prevented) or undesired (e.g., a disease not being treated or prevented) characteristics. The assay may be an immunoassay, such as a sandwich-type assay, competitive binding assay, one-step direct test, two-step test, or blot assay. The step of performing at least one assay may be performed robotically or manually.

Methods of Preparation

Further provided are methods of preparing compounds of Formula (I) and precursors thereof.

In one aspect, provided is a method of preparing a compound of Formula (I), the method comprising reacting the compound:

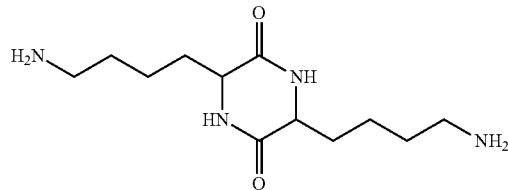 [SMILES: NCCCCC1NC(=O)C(CCCCN)NC1=O]

or salt thereof, with an epoxide of formula:

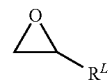

to provide a compound of Formula (I):

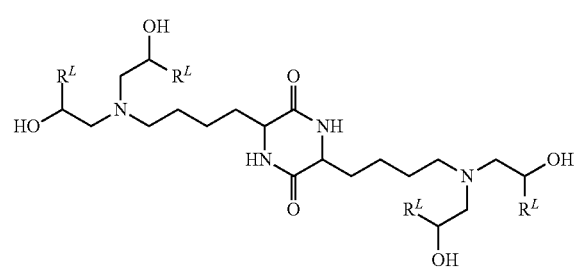

or salt thereof.

In certain embodiments, the step of reacting comprises use of a base, e.g., an organic base such as NEt$_3$. In certain embodiments, the step of reacting comprises use of irradiation to effect the coupling of the epoxide with the compound.

In another aspect, provided is a method of preparing an epoxide of formula:

the method comprising:

(i) reducing a carboxylic acid of formula:

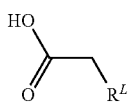

to an aldehyde of formula:

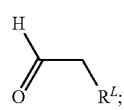

(ii) treating the aldehyde under alpha chlorinating conditions to provide a chlorinated aldehyde of formula:

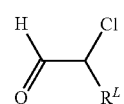

(iii) reducing the chlorinated aldehyde to provide an alcohol of formula:

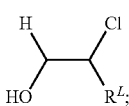

and (iv) treating the alcohol under suitable conditions to provide an epoxide of formula:

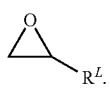

In certain embodiments, the step of reducing of the carboxylic acid comprises use of a hydride reducing agent, such as lithium aluminum hydride (LiAlH$_4$). In certain embodiments, the step of converting the aldehyde to the alpha-chlorinated aldehyde comprises use of a chlorinating agent, such as N-chlorosuccinimide (NCS). In certain embodiments, the step of reducing the chlorinated aldehyde to provide an alcohol comprises use of a hydride reducing agent, such as sodium borohydride (NaBH$_4$). In certain embodiments, the step of converting the alcohol to the epoxide comprises use of an inorganic base, such as NaOH.

EXAMPLES

In order that the invention described herein may be more fully understood, the following examples are set forth. It should be understood that these examples are for illustrative purposes only and are not to be construed as limiting this invention in any manner.

Alkenyl Amino Alcohol Ionizable Lipid Materials for Highly Potent In Vivo mRNA Delivery Nucleic acid therapies possess the potential to treat thousands of genetic disorders, many of which are difficult or impossible to manage with present day therapeutic approaches. For example, the successful delivery of short interfering RNAs (siRNA) to cells in both rodents and non-human primates has been leveraged to silence gene expression for the treatment of hereditary diseases and cancer. See, e.g., R. Kanasty et al., Nat Mater 2013, 12, 967-977; K. A. Whitehead et al., Nature reviews. Drug discovery 2009, 8, 129-138. As a complementary approach, the delivery of messenger RNA (mRNA) uniquely promotes the synthesis of specific proteins. Its successful delivery, therefore, could profoundly impact fields such as protein replacement therapy, vaccine development, and immune tolerization wherein the selective expression of proteins in vivo could treat disease. See, e.g., U. Sahin et al., Nature reviews. Drug discovery 2014, 13, 759-780; L. Zangi et al., Nature biotechnology 2013, 31, 898-907.

Before clinical implementation can be realized, serious limitations with the delivery of mRNA to target cells in the body must first be overcome. The high anionic charge density, size, and hydrophilicity of mRNA prevent meaningful levels of passive diffusion of mRNA across cell membranes. See, e.g., M. S. Kormann et al., Nature biotechnology 2011, 29, 154-157. To circumvent this limitation, an array of lipid nanoparticles (LNPs) has been developed for the entrapment and subsequent delivery of nucleic acids in vivo. See, e.g., R. Kanasty et al., Nat Mater 2013, 12, 967-977; K. A. Whitehead et al., Nature reviews. Drug discovery 2009, 8, 129-138. In practice, LNPs are comprised of cholesterol, a phospholipid, a polyethylene glycol derivative, and an ionizable lipid. See, e.g., T. M. Allen et al., Advanced drug delivery reviews 2013, 65, 36-48. Evidence within the siRNA delivery field has implicated the chemical identity and structure of the ionizable lipid in the LNP formulation as the most pivotal component for efficacy. Accordingly, several rationally designed and combinatorial chemistry methodologies have been employed to discover novel classes of ionizable lipid materials capable of maximizing gene silencing at the lowest possible siRNA dose. See, e.g., S. C. Semple et al. Nature biotechnology 2010, 28, 172-176; K. T. Love et al., Proceedings of the National Academy of Sciences of the United States of America 2010, 107, 1864-1869; Y. Dong et al., Proceedings of the National Academy of Sciences of the United States of America 2014, 111, 3955-3960. This strategy both conserves precious therapeutic nucleic acid cargo and also serves to mitigate any possible issues with the toxicity of the LNPs themselves.

Principles from from medicinal chemistry were leveraged to identify and synthesize a new class of alkenyl ionizable lipids that, when formulated into LNPs, promote the highest levels of in vivo protein expression reported to date. Along these lines, we also established critical structure/function parameters within this new class of materials that can serve as a synthetic baseline from which future generations of mRNA delivery materials can be based. Finally, we rigorously studied the delivery properties (i.e. batch-to-batch variability, dose response behavior, biodistribution, etc.) of the lead mRNA LNP we discovered through our study toward its clinical application as a delivery vehicle for mRNA therapeutics.

To begin our study, we first needed to select an optimal nucleic acid cargo to deliver in vivo. Unmodified mRNA coding for human Erythropoietin (EPO) was selected for two reasons: 1) the associated protein is secreted directly into the bloodstream allowing for robust protein quantification, and 2) EPO has potential therapeutic applications in such areas as anemia. See, e.g., M. S. Kormann et al., Nature biotechnology 2011, 29, 154-157; K. Kariko et al., Molecular therapy: the journal of the American Society of Gene Therapy 2012, 20, 948-953; S. Liu et al., Nutrition in clinical practice: official publication of the American Society for Parenteral and Enteral Nutrition 2013, 28, 120-127. Next, we established critical design parameters for our new class of ionizable lipids. Evidence from the siRNA delivery field highlights the success of amino alcohol based ionizable lipids. See, e.g., K. T. Love et al., Proceedings of the National Academy of Sciences of the United States of America 2010, 107, 1864-1869; Y. Dong et al., Proceedings of the National Academy of Sciences of the United States of America 2014, 111, 3955-3960. To the best of our knowledge, however, no amino alcohol based materials have been explored that incorporate cis carbon carbon double bonds (alkenes) throughout their hydrophobic tails. Here, we present the four compounds OF-00 through OF-03 as the first members of a new class of ionizable lipids for nucleic acid delivery (FIG. 1). OF-00 through OF-03 were synthesized through a ring opening reaction between diketopiperazine 1 and epoxy-alkenes EA-00 through EA-03 respectively. Epoxy-alkenes EA-00 through EA-03 are promising not only because they were used to furnish novel ionizable lipids for this report, but also because they could serve as versatile chemical building blocks for future AAA materials for nucleic acid delivery.

Compounds OF-00 through OF-03 were then formulated with human erythropoietin (EPO) mRNA, cholesterol, 1,2-dioleoyl-sn-glycero-3-phosphoethanolamine, and C14-PEG-2000 in accordance with previously optimized formulation parameters for mRNA delivery. See, e.g., A. Amirouche et al., Human molecular genetics 2013, 22, 3093-3111. Ionizable lipid cKK-E12 was formulated alongside these compounds to be used as a positive control in our study. cKK-E12 was chosen because it is structurally similar to compounds OF-00 through OF-03, but with shorter tails that do not contain alkenes. Additionally, cKK-E12 is capable of silencing Factor VII expression in mice at siRNA doses as low as 0.002 mg/kg, and as such it represents a benchmark ionizable lipid in the field of nucleic acid delivery. The nanoparticle diameters, polydispersity indices, and encapsulation efficiencies for each of these five formulations is provided in Table 1. Serum EPO concentrations are reported as mean±SD (n=3) 6 hr after a 0.75 mg/kg dose intravenous injection into mice. Encapsulation efficiencies, LNP diameter, and PDI were collected as described above for each representative LNP formulation.

TABLE 1

EPO Concentration and Characterization Data for LNP Formulations

| Ionizable Lipid LNP | Average EPO (ng/mL) | EPO Standard Deviation (ng/mL) | Encapsulation Efficiency (%) | LNP Diamter (nm) | PDI |
| --- | --- | --- | --- | --- | --- |
| cKK-E12 | 7100 ± 700 | 670 | 54 | 83 | 0.217 |
| OF-00 | 2100 ± 500 | 460 | 74 | 92 | 0.147 |
| OF-01 | 500 ± 200 | 180 | 81 | 78 | 0.194 |
| OF-02 | 14220 ± 1500 | 1490 | 55 | 122 | 0.130 |
| OF-03 | 140 ± 3 | 3 | 76 | 75 | 0.239 |

Figure 2:
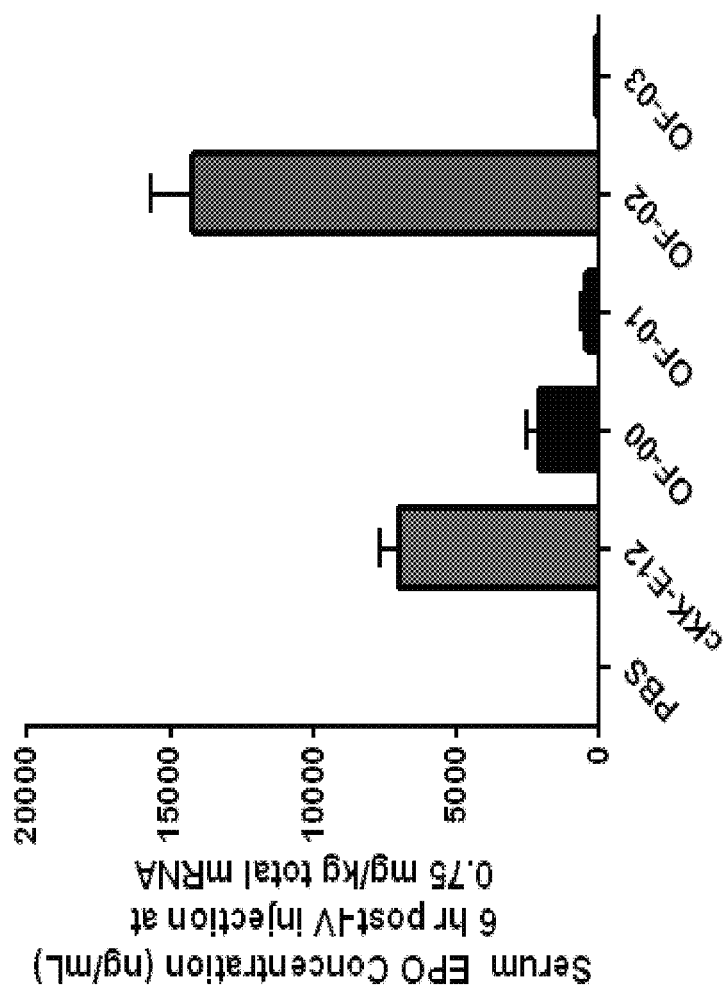
FIG. 2 depicts the in vivo EPO expression utilizing OF-00, OF-01, OF-02, and OF-03 for mRNA delivery. Data presented as mean+standard deviation (n=3).

Each resultant mRNA loaded LNP was then injected intravenously at a 0.75 mg/kg dose in C57BL/6 mice alongside phosphate buffered saline (PBS) as a negative control. At six hours, the serum EPO levels were quantified (FIG. 2). The PBS control imparted no significant EPO production in vivo, whereas positive control cKK-E12 LNPs promoted a serum EPO concentration of 7050 ng/mL. Excitingly, OF-02 LNPs significantly outperformed benchmark lipid cKK-E12 LNPs, promoting an approximate 2-fold increase in EPO concentration to 14420 ng/mL. Additionally, OF-02 outperformed two other benchmark ionizable lipids from the siRNA delivery field, namely 503-013 (See, e.g., J. McClellan, M. C. King, Cell 2010, 141, 210-217; Whitehead et al., Nature Communications (2014) 5:4277) and C12-200 (K. T. Love et al., Proceedings of the National Academy of Sciences of the United States of America 2010, 107, 1864-1869). These two compounds represent the leads in their respective ionizable lipid classes of acrylate esters and amino alcohols, and promoted respective EPO concentrations of 2836 ng/mL and 7065 ng/mL at an identical dose. To the best of our knowledge, OF-02 LNPs therefore represent the most potent mRNA delivery vehicle reported to date in the scientific literature.

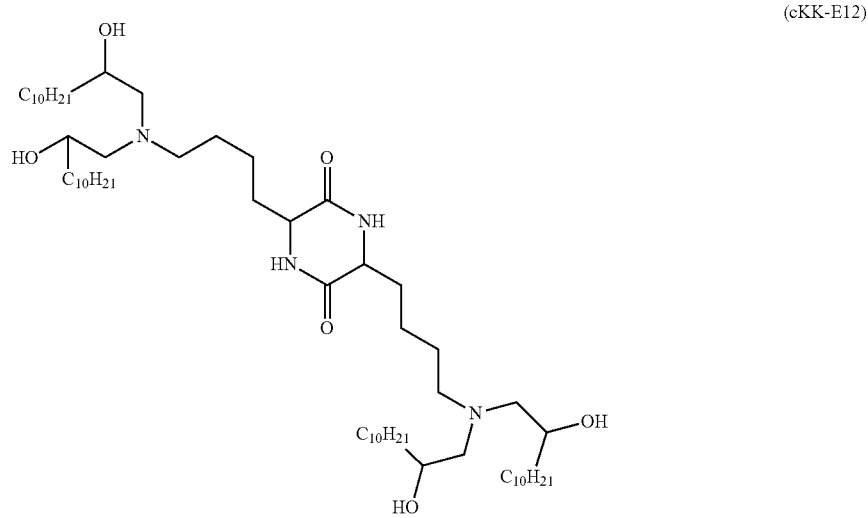

(cKK-E12)

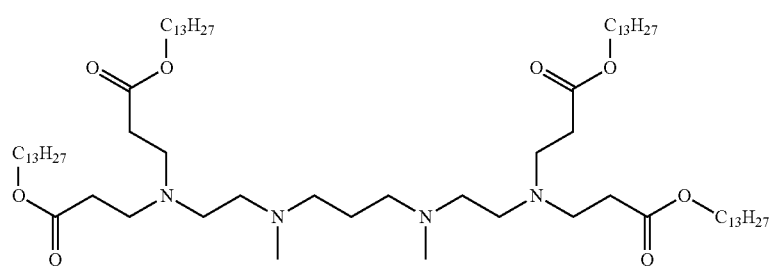

(503-O13)

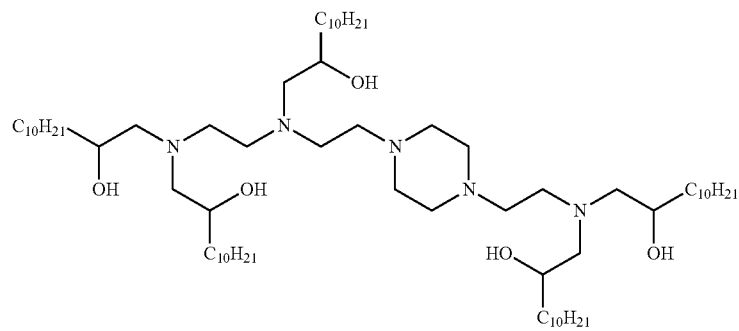

(C12-200)

The OF-00, OF-01, and OF-03 LNPs also allow the deduction of structure/function relationships within this new class of AAA ionizable lipids. We note two general structure/function trends of interest. First, we note that only alkenes with a cis geometry promote in vivo efficacy—OF-00 and OF-01 exclusively differ in the cis/trans geometry of their alkenes, and only OF-00 produces meaningful EPO concentrations. Second, the optimal number and placement of two cis alkenes per tail matches those observed in optimized siRNA LNPs. See, e.g., S. C. Semple et al., Nature biotechnology 2010, 28, 172-176.

Figure 3A:
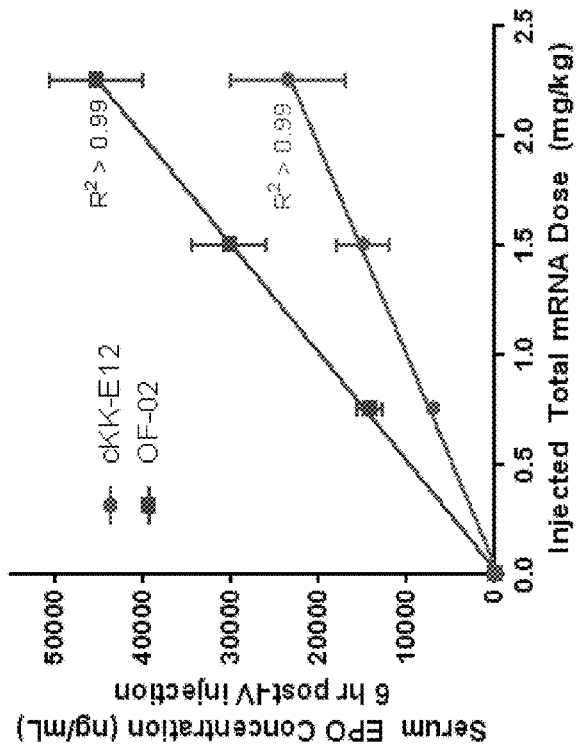
FIGS. 3A-3C present data related to EPO mRNA in vivo delivery utilizing lipid nanoparticles (LNPs).
Figure 3B:
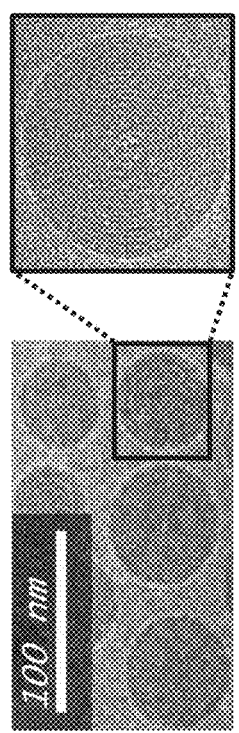

With this information in hand, our attention then shifted from exploring the general properties of the new AAA class of ionizable lipids to further characterizing LNPs made from our lead material OF-02. The clinical translation of nucleic acid delivery vehicles is in part predicated on high reproducibility of the chemical constituents and formulation of LNPs. To test this, three independent batches of OF-02 were synthesized and then formulated into LNPs. The average serum concentration among all batches was found to be 13705 ng/mL and demonstrated minimal batch-to-batch variability (FIG. 3A). Next, a dose response curve was collected at 0.75 mg/kg, 1.5 mg/kg, and 2.25 mg/kg total EPO mRNA dose for both OF-02 and cKK-E12 LNPs (FIG. 3B). OF-02 LNPs outperformed their cKK-E12 counterparts roughly 2 fold across all doses studied, reaching a maximum EPO concentration of 45354 ng/mL at the 2.25 mg/kg dose. It is also interesting to note that both sets of LNPs promote EPO production in a linear fashion with respect to dose. This trend implies that we have not yet reached a saturation point for the intracellular translation machinery, suggesting protein production is currently only limited by the dose of mRNA.

Figure 3C:
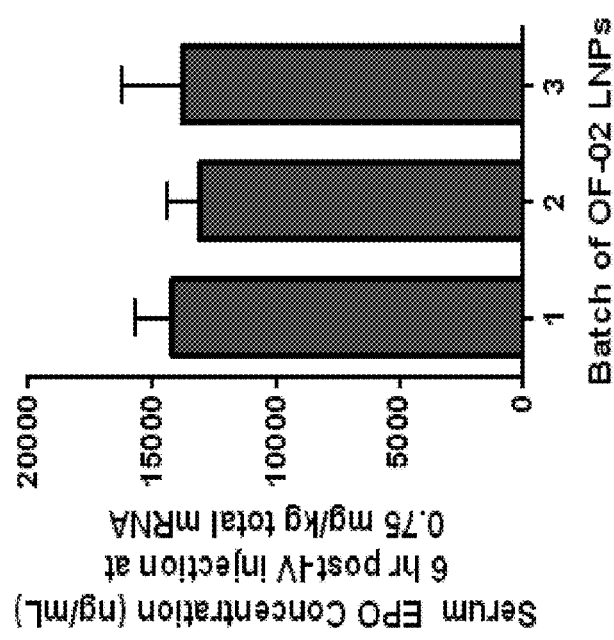

We explored the morphology of OF-02 formulations using cryogenic transmission electron microscopy (FIG. 3C). Key structural features include a narrow polydispersity index (0.130) with an average particle diameter around 100 nm. Additionally, a closer view of an individual LNP details a multilamellar structure; we suspect the EPO mRNA is positioned throughout the LNP in alternating lipid/mRNA layers, as has been shown for similar siRNA LNP formulations. To the best of our knowledge, these are the first nanoscale images of mRNA-loaded LNPs reported in the literature.

Figure 4B:
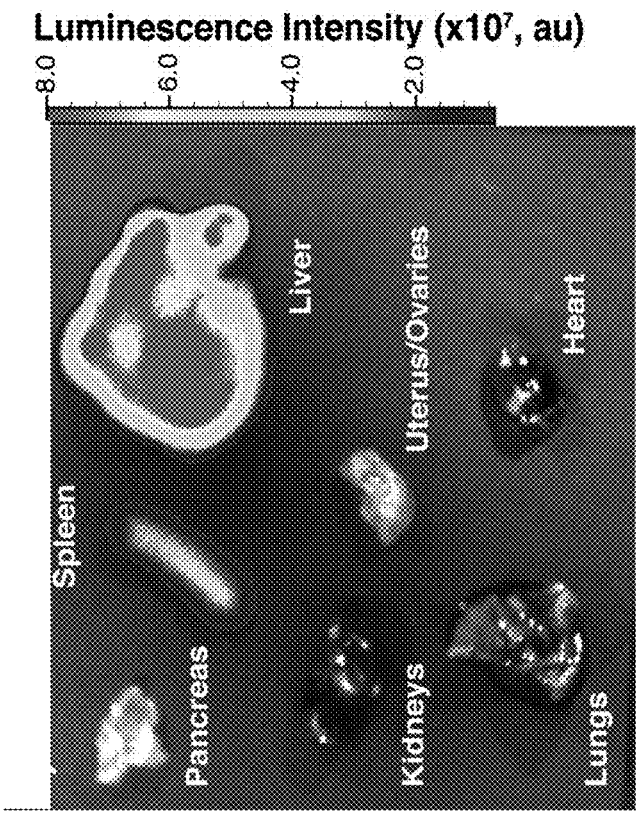
FIGS. 4A-4B depicts representative luminescence biodistribution of cKK-E12 LNPs (FIG. 4A) and OF-02 LNPs (FIG. 4B) with luciferase mRNA in vivo.
Figure 4A:
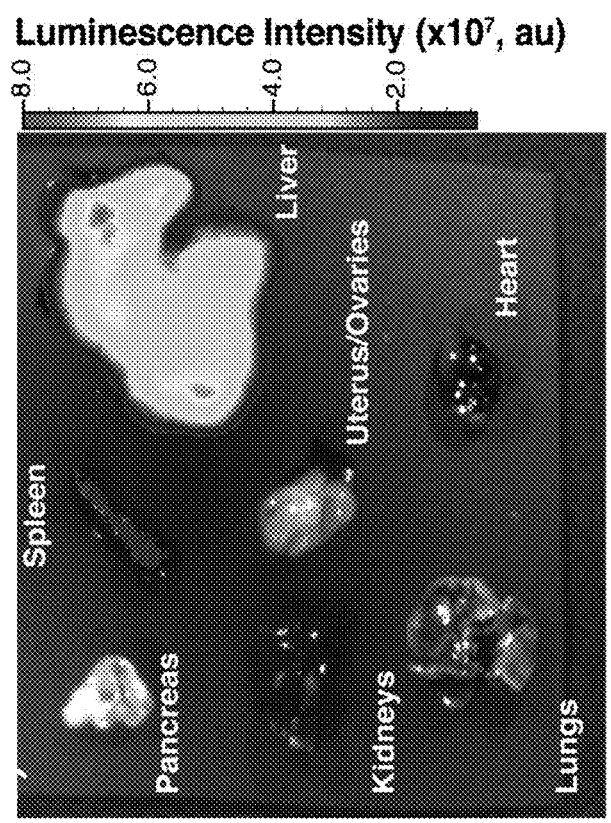
Figure 5:
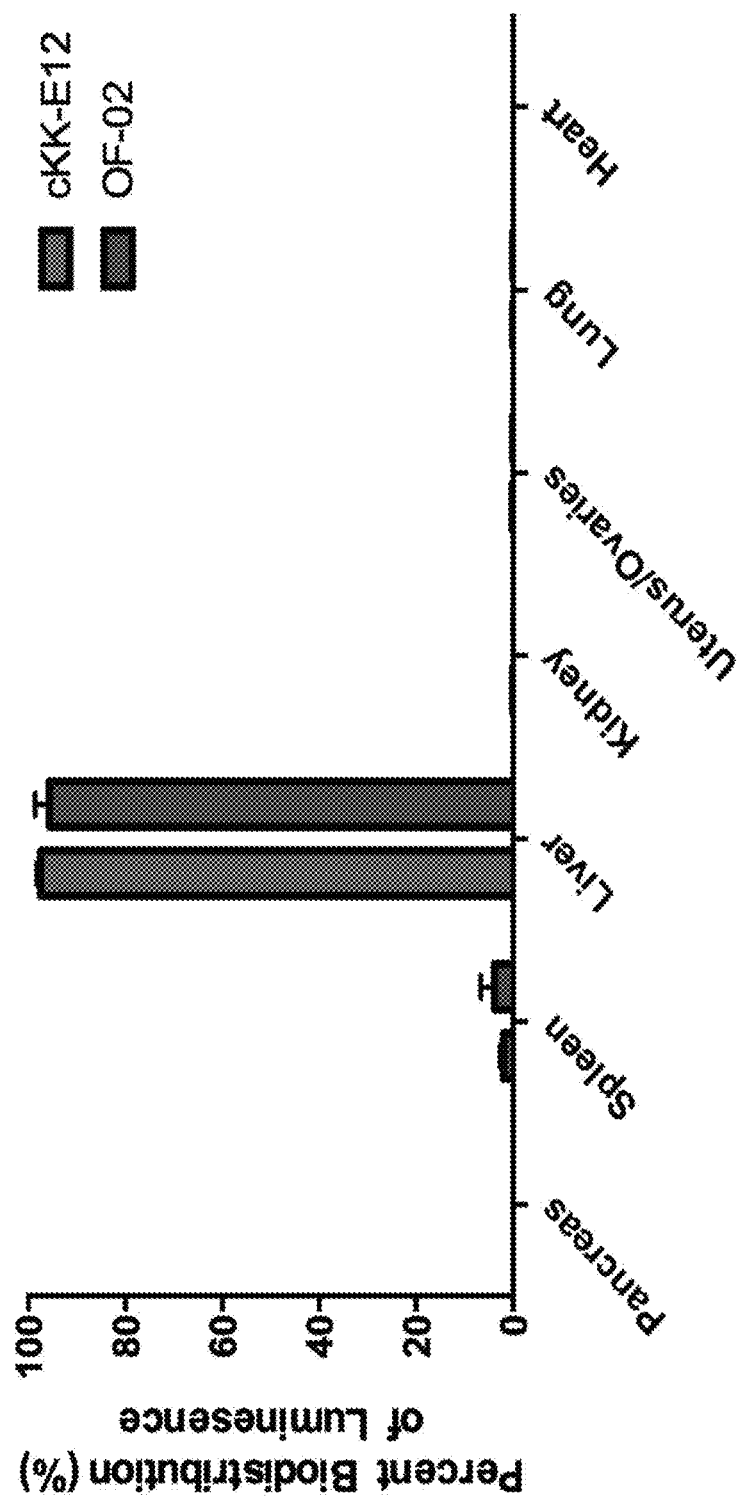
FIG. 5 depicts the quantified cKK-E12 and OF-02 results of the Luciferase LNPs for Luminescence of FIGS. 4A-4B. Organ luminescence was analyzed using an IVIS imaging system (Perkin Elmer, Waltham, Mass.). The luminescence was quantified using LivingImage software (Perkin Elmer) to measure the radiance of each organ in photons/se. Data presented as mean+standard deviation (n=4).

We were interested to determine if the efficacy differences observed between ckk-E12 and OF-02 LNPs were due to variations in biodistribution. mRNA coding for luciferase was independently formulated with both ckk-E12 and OF-02 in the same fashion as for EPO delivery, and mouse organs were harvested 24 hours post injection. The tissues were subsequently imaged ex-vivo to measure the total luminescence per organ, demonstrating that mRNA from both ckk-E12 and OF-02 LNPs is predominantly translated in the liver with minimal translation in the spleen and negligible translation in other organs (FIGS. 4A and 4B). Quantification of this data also confirms nearly identical biodistribution profiles for the two formulations, suggesting that the increased efficacy of OF-02 LNPs is not due to a difference in tissue targeting (FIG. 5). Since more than 4000 human diseases are caused by liver genetic disorders such as hemophilias A and B, OF-02 LNPs represent a promising delivery vehicle for therapeutic mRNA delivery to the liver. See, e.g., J. McClellan et al., Cell 2010, 142, 353-355.

Figure 6:
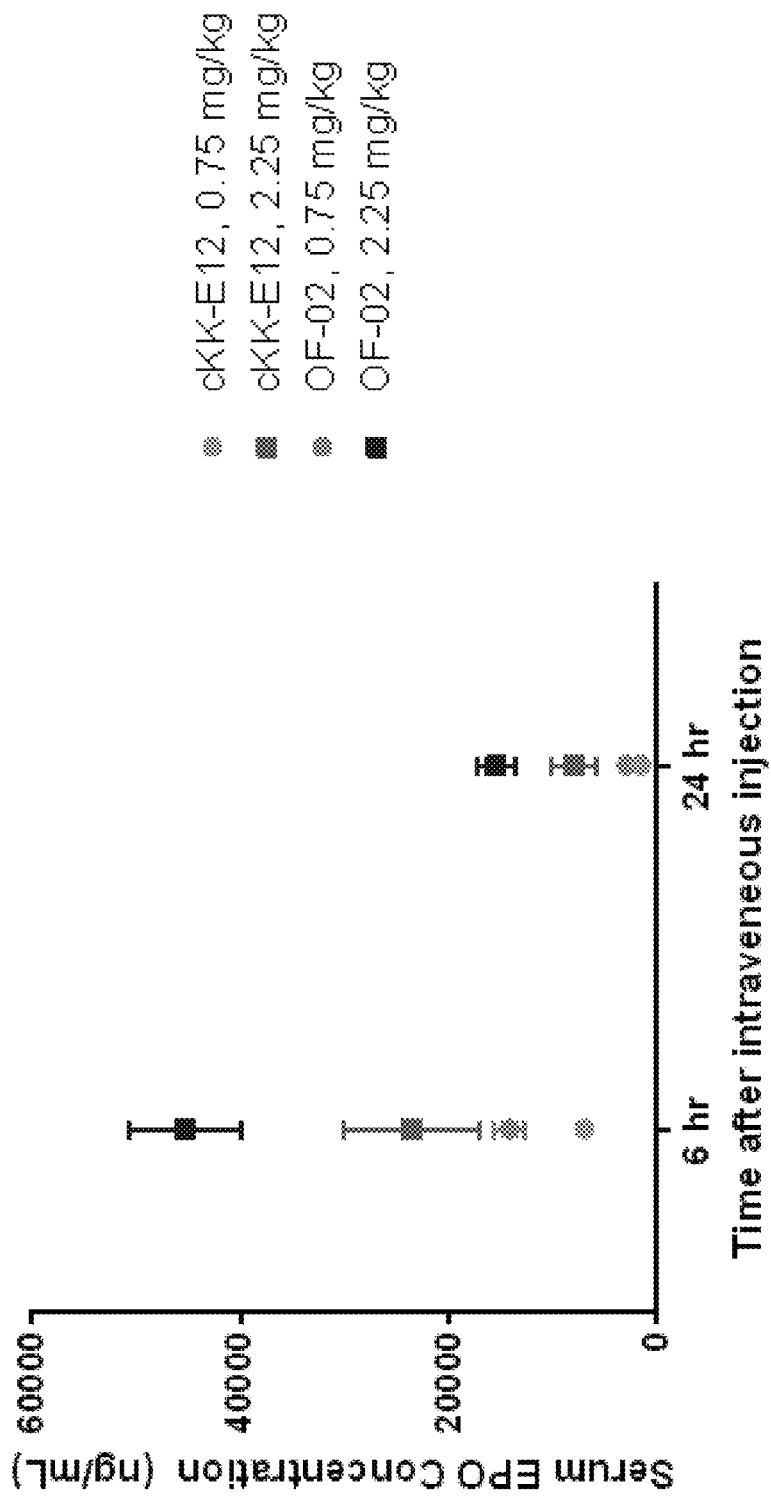
FIG. 6 depicts the EPO Concentrations of OF-02 vs. cKK-E12 LNPs at 6 and 24 h. Data presented as mean±standard deviation (n=3).
Figure 7:
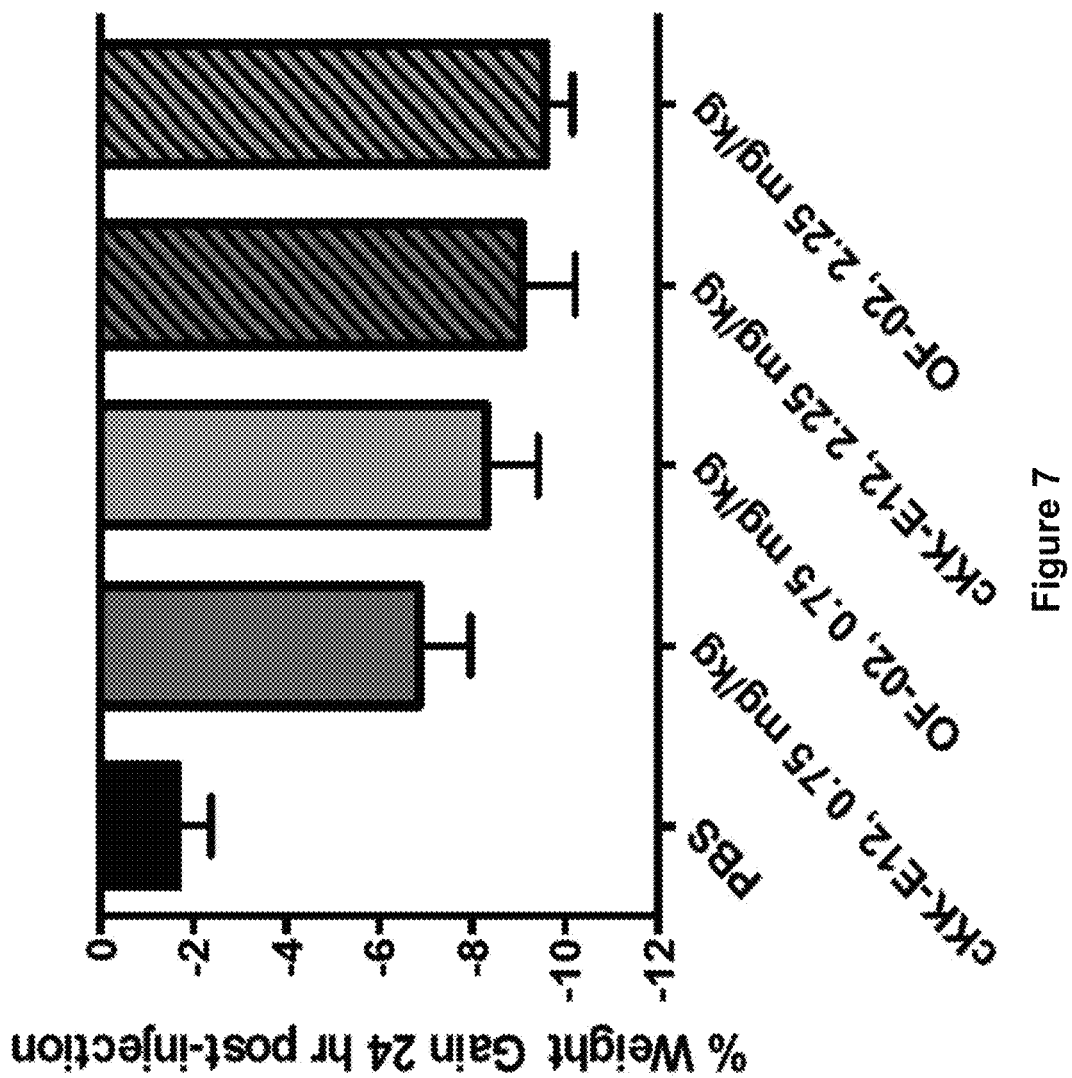
FIG. 7 depicts the percent weight gain for cKK-E12 and OF-02 mRNA LNPs reported as mean−SD (n=3) 24 hours after respective intravenous dose into mice.

Finally, OF-02 LNPs also outperformed their cKK-E12 counterparts at 24 hours, independent of dose (FIG. 6). The sharp decrease in EPO concentration as a function of time highlights one of the many exciting potential therapeutic advantages of mRNA delivery in vivo; in contrast to permanent gene replacement therapies, mRNA delivery offers transient, dose-response dependent protein expression in vivo, a property that could one day prove useful for a variety of genetic disorders. It is important to note that no animal mortality was observed at all doses studied, and that mice treated with both cKK-E12 and OF-02 LNPs displayed similar weight loss profiles at identical doses (FIG. 7). OF-02 LNPs therefore represent a tunable handle for in vivo EPO production readily capable of exceeding normal human EPO levels (40-250 pg/mL) in our chosen mouse model. See, e.g., Cazzola et al., Blood 1997, 89, 4248-4267.

In summary, our study began by creating a new class of ionizable lipid materials for mRNA delivery dubbed AAAs. To the best of our knowledge, compounds OF-00 through OF-03 represent the first examples of these AAA materials in the scientific literature, and we hope that their alkene-epoxide precursors EA-00 through EA-03 can serve as versatile scaffolds for the synthesis of future AAA ionizable lipids. After determining that OF-02 LNPs yielded the highest levels of mRNA promoted EPO levels in vivo in the scientific literature, our attention shifted to the characterization of LNPs derived from lead compound OF-02. Batch-to-batch variability, dose response curves, and cryogenic TEM images were coupled with biodistribution data, highlighting the exceptional potency with which these LNPs can deliver mRNA to the liver.

Materials and Methods

General Lipid Nanoparticle (LNP) Synthesis. The organic phase was prepared by solubilizing with ethanol a mixture of ionizable lipid, 1,2-dioleoyl-sn-glycero-3-phosphoethanolamine (DOPE, Avanti), cholesterol (Sigma), and 1,2-dimyristoyl-sn-glycero-3-phosphoethanolamine-N-[methoxy(polyethyleneglycol)-2000] (ammonium salt) (C14-PEG 2000, Avanti) at a molar ratio of 35:16:46.5:2.5 and ionizable lipid:mRNA weight ratio of 10:1 in accordance with previously optimized formulation parameters for mRNA delivery. The aqueous phase was prepared in 10 mM citrate buffer (pH 3) with either EPO mRNA (human Erythropoietin mRNA, courtesy of Shire Pharmaceuticals, Cambridge, Mass.) or Luc mRNA (Firefly luciferase mRNA, Shire). The ethanol and aqueous phases were mixed at a 3:1 ratio in a microfluidic chip device (ref Delai's paper) using syringe pumps as previously described at a final mRNA concetration of 0.1 mg/mL. See, e.g., Chen et al., J. Am. Chem. Soc. (2012) 134:6948. Resultant LNPs were dialyzed against PBS in a 20,000 MWCO cassette at 4° C. for 2 hours.

LNP Characterization. To calculate the mRNA encapsulation efficiency, a modified Quant-iT RiboGreen RNA assay (Invitrogen) was used as previously described. See, e.g., Heyes et al., J. Controlled Release (2005) 107:276-287. The diameter and polydispersity (PDI) of the LNPs were measured using dynamic light scattering (ZetaPALS, Brookhaven Instruments). LNP diameters are reported as the largest intensity mean peak average, which constituted >95% of the nanoparticles present in the sample.

Cryogenic Transmission Electron Microscopy of Lipid Nanoparticles. LNPs were prepared as previously described in General Lipid Nanoparticle Synthesis, with the exception that they were dialyzed against 0.1×PBS instead of 1×PBS. The batch of LNPs was then split, and the encapsulation efficiency was calculated for a subpopulation of the LNPs using the aforementioned method (section 3: General Lipid Nanoparticle Characterization, Quanti-iT RiboGreen RNA assay from Invitrogen, see above). The remaining LNPs were then prepared for Cryogenic TEM. Briefly, 3 µL of the LNP solution was diluted with buffer and was placed onto a lacey copper grid coated with a continuous carbon film. Excess sample was blotted off using a Gatan Cryo Plunge III. The grid was then mounted on a Gatan 626 cryo-holder equipped within the TEM column. The specimen and holder tip were continually cooled by liquid nitrogen during transfer into the microscope and subsequent imaging. Imaging was performed using a JEOL 2100 FEG microscope using a minimum dose method that was essential to avoiding sample damage under the electron beam. The microscope was operated at 200 kV and with a magnification setting of 60,000 for assessing particle size and distribution. All images were recorded on a Gatan 2 k×2 k UltraScan CCD camera.

Animal Experiments. All animal studies were approved by the M.I.T. Institutional Animal Care and Use Committee and were consistent with local, state and federal regulations as applicable. LNPs were intraveneously injected in female C57BL/6 mice (Charles River Labs, 18-22 grams) via the tail vein. After six or 24 hours, blood was collected via the tail vein and serum was isolated by centrifugation in serum separation tubes. Serum EPO levels were quantified with an ELISA assay (Human Erythropoietin Quantikine IVD ELISA Kit, R&D Systems, Minneapolis, Md.). 24 hours after injection of Luc-mRNA LNPs, mice were injected intraperitoneally with 130 µL of D-luciferin (30 mg/mL in PBS). After fifteen minutes, mice were sacrificed and the organs were isolated (pancreas, spleen, liver, kidneys, lungs, heart, uterus and ovaries) and imaged with an IVIS imaging system (Perkin Elmer, Waltham, Mass.). Luminescence was quantified using LivingImage software (Perkin Elmer).

Synthetic Procedures

Instrumentation and Materials. Microwave reactions were performed in a Biotage Initiator. Other reactions were performed in round bottom flasks. Proton nuclear magnetic resonance ($^1$H NMR) spectra were recorded with a Varian inverse probe INOVA-500 spectrometer (with a Magnex Scientific superconducting actively-shielded magnet), are reported in parts per million on the δ scale, and are referenced from the residual protium in the NMR solvent (CDCl$_3$: δ 7.24; DMSO: δ2.50). Data are reported as follows: chemical shift [multiplicity (br=broad, s=singlet, d=doublet, t=triplet, sp=septet, m=multiplet), integration, assignment. All commercial reagents and solvents were used as received.

General Description. One of the most common and facile synthetic methods to afford epoxides relies on the oxidation of alkenes using meta-chloroperbenzoic acid (mcpba).H However, we immediately recognized this as a poor synthetic strategy for synthesizing alkenyl epoxides EA-00 through EA-03 because the selective oxidation of a terminal alkene in the presence of electronically similar alkenes would be extremely difficult if not impossible. Purification of the reaction medium would also be highly challenging due to the similar polarity of products and the complexity of the mixture ensuing from the reaction. In order to circumvent this problem, we elected to use biologically relevant fatty acids as our general synthetic starting material. We envisioned that fatty acids would serve as excellent synthetic building blocks for our study because they are abundant in large quantities from many commercial vendors and they also offer high levels of regiochemical fidelity in their alkenes. Additionally, fatty acids would allow us to circumvent the forecasted issue with mcpba oxidation; we envisioned that the carboxylic acid termini could be used to directly furnish the epoxide while leaving the alkenes in the substrate fully intact.

Having selected fatty acids as an ideal starting material, we executed our synthesis of alkenyl epoxides. For a general scheme and the fully drawn products, see Scheme 1 below. Briefly, fatty acids were subjected to a lithium aluminum hydride reduction followed by Dess-Martin Periodinane oxidation to afford their corresponding aldehydes. Proline catalyzed alpha-chlorination followed by sodium borohydride reduction in the same reaction flask afforded the 1,2-chloroalcohols in moderate yields. See, e.g., N. Halland et al., Journal of the American Chemical Society 2004, 126, 4790-4791. Finally, gentle heating of these 1,2-chloroalcohols at 35° C. in basic dioxane promoted ring closure to furnish the desired alkene-containing epoxides EA-00 through EA-03 in moderate yields in 4 steps with only a single chromatographic purification. Excitingly, these alkene-containing epoxides represent a virtually unexplored synthetic scaffold for ionizable lipid development. We hope this synthetic route will broadly add to the creation of future generations of ionizable lipids for nucleic acid therapy. Full synthetic procedures and molecular characterization data for each step of the synthetic procedures for EA-00 through EA-03 are available below, as are the final syntheses of OF-00 through OF-03.

Scheme 1.

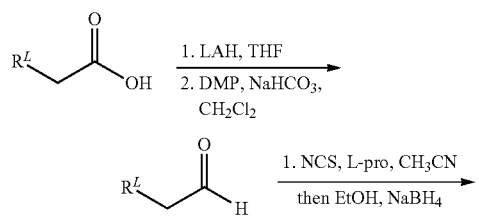

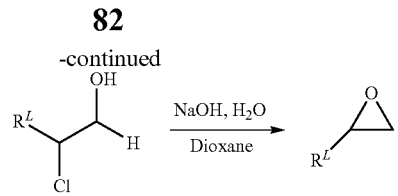

Example 1

OF-00 Synthesis

Step 1. Synthesis of EA-00-aldehyde

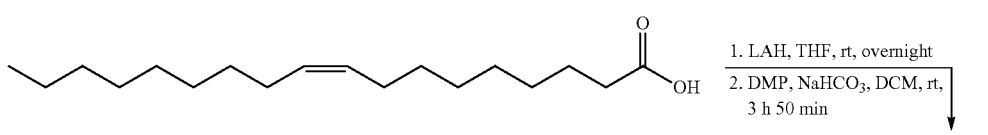

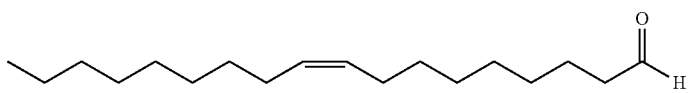

To a solution of oleic acid (5.01 ml, 15 mmol, 1 eq) in THF (190 ml) at 0° C. was added lithium aluminum hydride (1 M in THF, 22.5 ml, 22.5 mmol, 1.5 eq) dropwise. The solution was allowed to warm to room temperature and was stirred overnight. The reaction was quenched with sequential additions of water (0.85 ml), 1N NaOH (0.85 ml), and water (2.6 ml) dropwise. The mixture was filtered through celite, and the filtrate was concentrated under reduced pressure. The crude product, EA-00-aldehyde, a yellow oil, was then dissolved in CH$_2$Cl$_2$ (160 ml). NaHCO$_3$ (8.821 g, 105 mmol, 7 eq) was added followed by Dess-Martin Periodinane (7.63 g, 18 mmol, 1.2 eq). The mixture was stirred for 3 hours, 50 minutes. It was then diluted in petroleum ether, washed sequentially with saturated NaHCO$_3$ and brine, dried over anhydrous sodium sulfate, filtered, and concentrated under reduced pressure. The crude product, a yellow oil, was used without further purification.

Step 2. Synthesis of EA-00-chloroalcohol

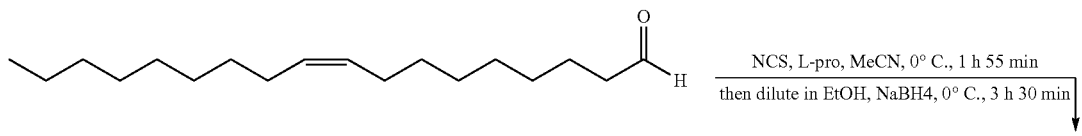

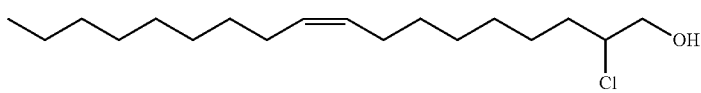

To a solution of EA-00-aldehyde (3.91 g, 14.7 mmol, 1 eq) in MeCN (40 ml) cooled to 0° C. was added L-proline (0.507 g, 4.41 mmol, 0.3 eq) and N-chlorosuccinimide (1.8657 g, 14.0 mmol, 0.95 eq). The solution was stirred at 0° C. for 1 hour, 55 minutes. It was then diluted in ethanol (23 mL) and to it was added NaBH$_4$ (71 mg, 1.875 mmol, 2.5 eq). The mixture was stirred at 0° C. for 3 hours, 30 minutes. It was then diluted in ethyl acetate, washed with brine, dried over anhydrous sodium sulfate, filtered, and concentrated under reduced pressure. The crude product EA-00-chloroalcohol, a yellow oil, was used without further purification.

Step 3. Synthesis of EA-00

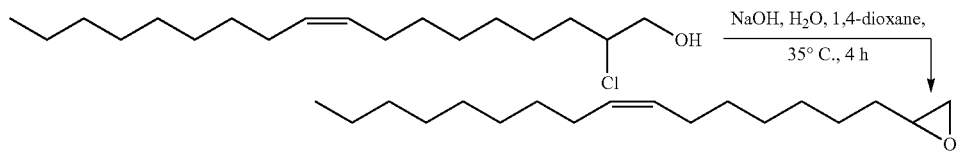

To a solution of EA-00-chloroalcohol (3.495 g, 11.6 mmol, 1 eq) in 1,4-dioxane (35 ml) was added a solution of NaOH (10.44 g, 261 mmol, 22.5 eq) in water (45 ml). The reaction mixture was heated to 35° C. and allowed to stir for 4 hours. The resulting mixture was then diluted in hexanes, washed with brine, dried over anhydrous sodium sulfate, filtered, and concentrated under reduced pressure. The crude product was purified by flash chromatography on silica gel using acetone/hexanes (0:100→6:94) to yield EA-00 (0.441 g, 1.65 mmol, 14% yield over 4 steps) as a pale yellow oil.

$^1$H NMR (500 MHz, CDCl$_3$, 20° C.): 5.34 (m, 2H, CHCH), 2.90 (m, 1H, CH$_2$OCH), 2.74 (ddd, 1 H, CH$_2$OCH), 2.46 (m, 1H, CH$_2$OCH), 2.01 (pd, 4H, CHCHCH$_2$), 1.68-1.18 (m, 22H, CH$_2$), 0.88 (t, 3H, CH$_3$).

Step 4. Synthesis of OF-00

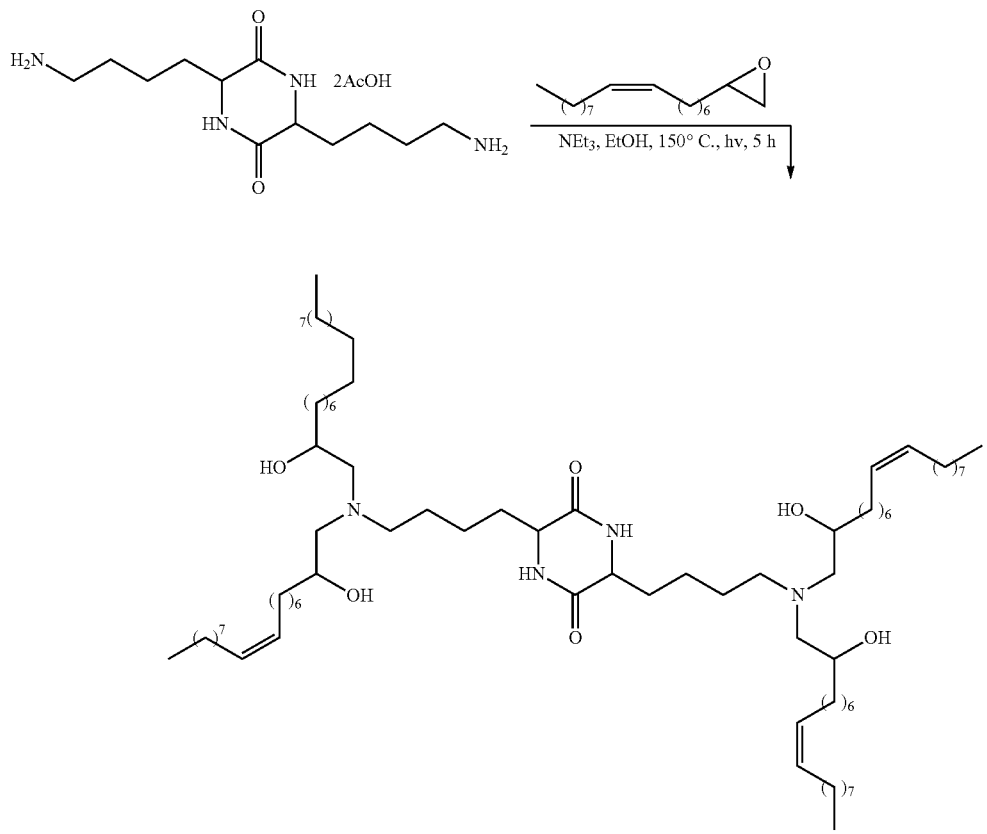

To a solution of EA-00 (359 mg, 1.35 mmol, 6 eq) in ethanol (2 ml) was added diketopiperazine 1 (84.7 mg, 0.225 mmol, 1 eq) followed by triethylamine (125 μl, 0.9 mmol, 4 eq). See, e.g., Y. Dong et al., Proc Natl Acad Sci USA 2014, 111, 3955-3960. The mixture was stirred at room temperature for 5 minutes before being irradiated, with stirring, in a microwave for 5 hours at 150° C. The crude product was purified by flash chromatography to yield the product as a viscous yellow oil (19% yield).

$^1$H NMR (500 MHz, DMSO-$d_6$, 20° C.) 8.11 (br, 2H, CONH), 5.15-5.2 (m, 8H, $CH_2CH$), 4.21 (dd, 4H, OH), 3.79 (br, 2H, COCH), 3.44 (br, 4H, CHOH), 2.25-2.44 (m, 12H, $NCH_2$), 2.1 (m, 16H, $CHCH_2CH_2$), 1.64-1.67 (m, 4H, $CH_2$), 1.21-1.39 (m, 96H, $CH_2$), 0.88 (t, 12H, $CH_3$). HRMS (DART) (m/z): calc'd for $C_{84}H_{160}N_4O_6$ [M+H]*: 1322.23. found: 1322.04.

Example 2

OF-01 Synthesis

Step 1. Synthesis of EA-01-aldehyde

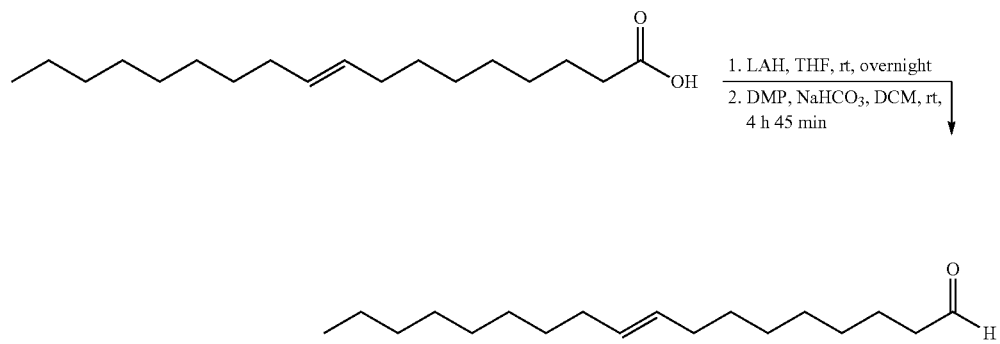

To a solution of elaidic acid (4.717 g, 16.7 mmol, 1 eq) in THF (210 ml) at 0° C. was added Lithium Aluminum Hydride (1 M in THF, 25 ml, 25 mmol, 1.5 eq) dropwise. The solution was allowed to warm to room temperature and was stirred overnight. The reaction was quenched with sequential additions of water (0.95 ml), 1N NaOH (0.95 ml), and water (2.9 ml) dropwise. The mixture was filtered through celite, and the filtrate was concentrated under reduced pressure. The crude product, (E)-octadec-9-en-1-ol, was then dissolved in $CH_2Cl_2$ (180 ml). $NaHCO_3$ (9.820 g, 116.9 mmol, 7 eq) was added followed by Dess Martin Periodinane (8.5 g, 20 mmol, 1.2 eq). The mixture was stirred for 4 hours, 45 minutes. It was then diluted in petroleum ether, washed sequentially with saturated $NaHCO_3$ and brine, dried over anhydrous sodium sulfate, filtered, and concentrated under reduced pressure. The crude product EA-01-aldehyde, a white solid, was used without further purification.

Step 2. Synthesis of EA-01-chloroalcohol

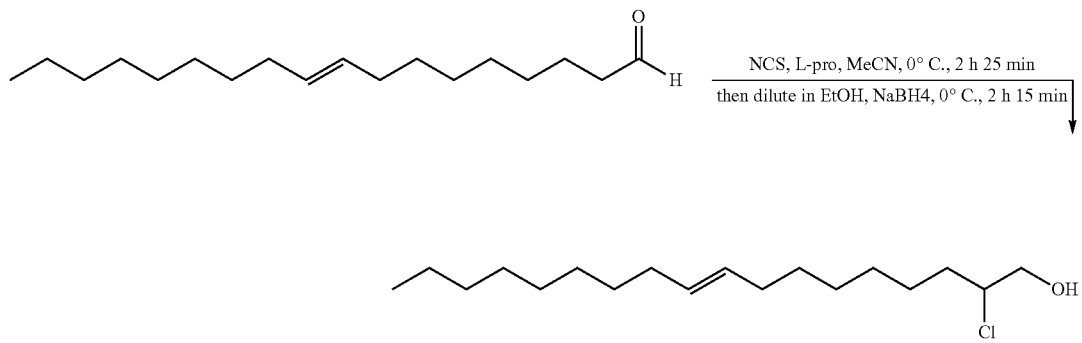

To a solution EA-01-aldehyde (16.7 mmol, 1 eq) in MeCN (46 ml) cooled to 0° C. was added L-proline (0.577 g, 5.01 mmol, 0.3 eq) and N-chlorosuccinimide (2.118 g, 15.8 mmol, 0.95 eq). The solution was stirred at 0° C. for 2 hours, 25 minutes. It was then diluted in ethanol (26 ml) and to it was added NaBH$_4$ (1.579 g, 41.75 mmol, 2.5 eq). The mixture was stirred at 0° C. for 2 hours, 15 minutes. It was then diluted in ethyl acetate, washed with brine, dried over anhydrous sodium sulfate, filtered, and concentrated under reduced pressure. The crude product EA-01-chloroalcohol, a white solid, was used without further purification.

Step 3. Synthesis of EA-01

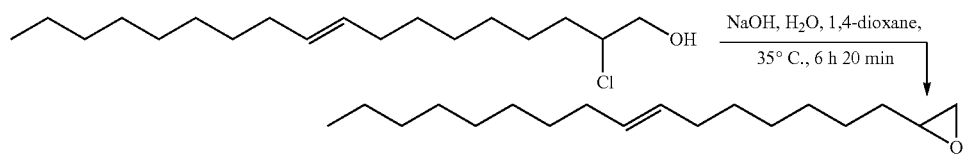

To a solution of EA-01-aldehyde in 1,4-dioxane (50 ml) was added a solution of NaOH (15.03 g, 376 mmol, 22.5 eq) in water (65 ml). The reaction mixture was heated to 35° C. and allowed to stir for 6 hours, 20 minutes. The resulting mixture was then diluted in hexanes, washed with brine, dried over anhydrous sodium sulfate, filtered, and concentrated under reduced pressure. The crude product was purified by flash chromatography on silica gel using acetone/hexanes (0:100→10:90) to yield EA-01 as an off-white oil (19% yield over 4 steps). $^1$H NMR (500 MHz, CDCl$_3$, 20° C.): 5.37 (m, 2H, CHCH), 2.87 (tq, 1H, CH$_2$OCH), 2.71 (m, 1H, CH$_2$OCH), 2.43 (dt, 1H, CH$_2$OCH), 1.95 (m, 4 H, CHCHCH$_2$), 1.36-1.16 (m, 22 H, CH$_2$), 0.86 (t, 3 H, CH$_3$).

Step 4. Synthesis of OF-01

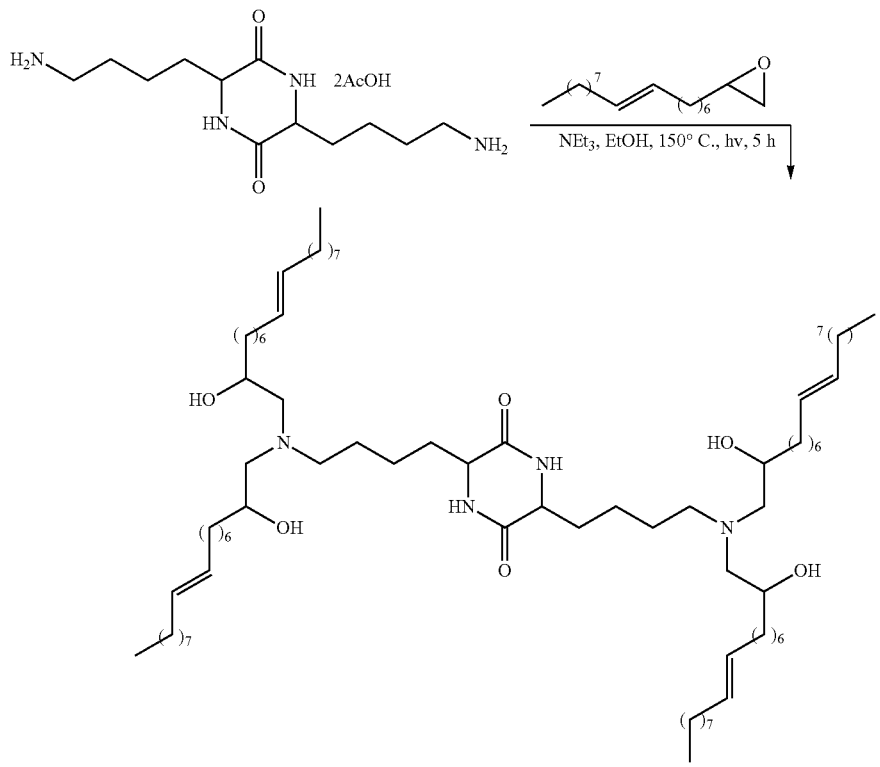

To a solution of EA-01 (359 mg, 1.35 mmol, 6 eq) in ethanol (2 ml) was added diketopiperazine 1 (84.7 mg, 0.225 mmol, 1 eq) followed by triethylamine (125 μl, 0.9 mmol, 4 eq). See, e.g., Y. Dong et al., Proc Natl Acad Sci USA 2014, 111, 3955-3960. The mixture was stirred at room temperature for 5 minutes before being irradiated, with stirring, in a microwave for 5 hours at 150° C. The crude product was purified by flash chromatography to yield the product as a yellow oil (9% yield).

$^1$H NMR (500 MHz, DMSO-$d_6$, 20° C.) 8.11 (br, 2H, CONH), 5.15-5.2 (m, 8H, $CH_2CH$), 4.21 (dd, 4H, OH), 3.79 (br, 2H, COCH), 3.44 (br, 4H, CHOH), 2.25-2.44 (m, 12H, $NCH_2$), 2.1 (m, 16H, $CHCH_2CH_2$), 1.64-1.67 (m, 4H, $CH_2$), 1.21-1.39 (m, 96H, $CH_2$), 0.88 (t, 12H, $CH_3$). HRMS (DART) (m/z): calc'd for $C_{84}H_{160}N_4O_6$ [M+H]*: 1322.23. found: 1322.09.

Example 3

Synthesis of OF-02

Step 1. Synthesis of EA-02-aldehyde

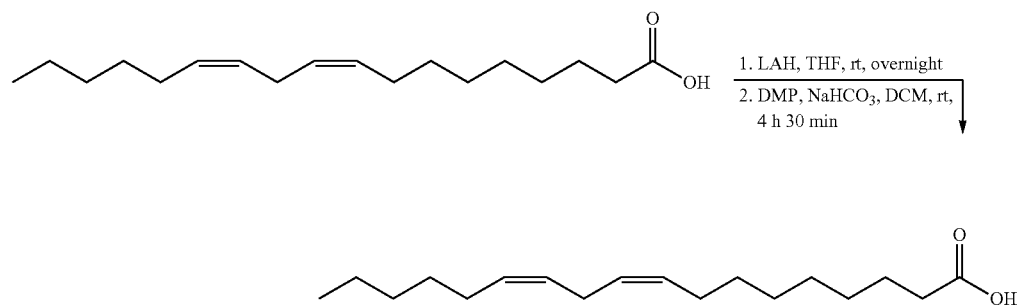

To a solution of linoleic acid (4.66 ml, 15 mmol, 1 eq) in THF (190 ml) at 0° C. was added Lithium Aluminum Hydride (1 M in THF, 22.5 ml, 22.5 mmol, 1.5 eq) dropwise. The solution was allowed to warm to room temperature and was stirred overnight. The reaction was quenched with sequential additions of water (0.85 ml), 1N NaOH (0.85 ml), and water (2.6 ml) dropwise. The mixture was filtered through celite, and the filtrate was concentrated under reduced pressure. The crude product was subsequently dissolved in $CH_2Cl_2$ (160 ml). $NaHCO_3$ (8.821 g, 105 mmol, 7 eq) was added followed by Dess-Martin-Periodinane (7.63 g, 18 mmol, 1.2 eq). The mixture was stirred for 4 hours, 30 minutes. It was then diluted in petroleum ether, washed sequentially with saturated $NaHCO_3$ and brine, dried over anhydrous sodium sulfate, filtered, and concentrated under reduced pressure. The crude product EA-02-aldehyde, a yellow oil, was used without further purification.

Step 2. Synthesis of EA-02-chloroalcohol

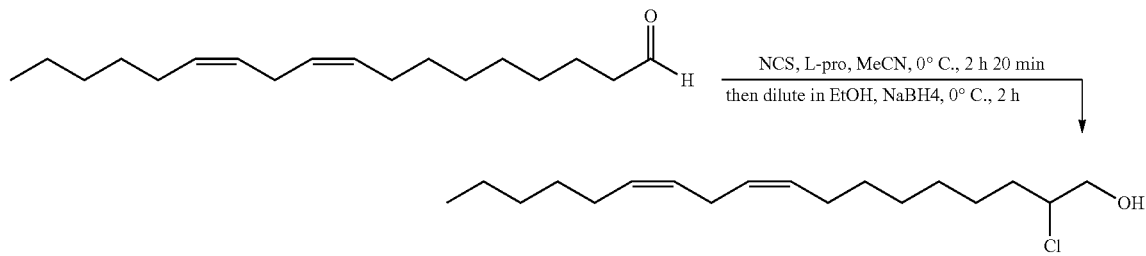

To a solution EA-02-aldehyde (3.3955 g, 12.7 mmol, 1 eq) in MeCN (35 ml) cooled to 0° C. was added L-proline (518 mg, 4.5 mmol, 0.3 eq) and N-chlorosuccinimide (1.903 g, 14.25 mmol, 0.95 eq). The solution was stirred at 0° C. for 2 hours 20 minutes. It was then diluted in ethanol (20 ml) and to it was added NaBH$_4$ (1.418 g, 37.5 mmol, 2.5 eq). The mixture was stirred at 0° C. for 2 hours. It was then diluted with ethyl acetate, washed with brine, dried over anhydrous sodium sulfate, filtered, and concentrated under reduced pressure. The crude product EA-02-chloroalcohol, a yellow oil was used without further purification.

Step 3. Synthesis of EA-02

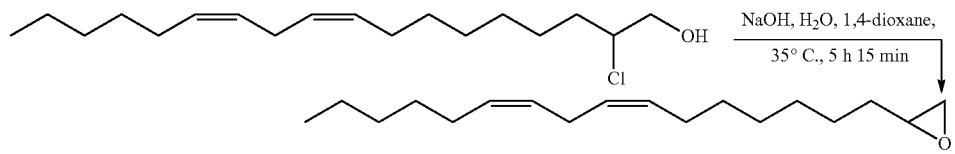

To a solution of EA-02-chloroalcohol (1.4768 g, 4.91 mmol, 1 eq) in 1,4-dioxane (14.7 ml) was added a solution of NaOH (4.417 g, 110.4 mmol, 22.5 eq) in water (19.4 ml). The reaction mixture was heated to 35° C. and allowed to stir for 5 hours, 15 minutes. The resulting mixture was then diluted in hexanes, washed with brine, dried over anhydrous sodium sulfate, filtered, and concentrated under reduced pressure. The crude product was purified by flash chromatography on silica gel using ether/petroleum ether (0:100→20:80) to yield EA-02 (in 41% yield over 4 steps).

$^1$H NMR (500 MHz, CDCl$_3$, 20° C.): 5.33 (m, 4 H, CHCH), 2.88 (tdd, 1H, CH$_2$OCH), 2.73 (m, 3H, CH$_2$OCH and CHCH$_2$CH), 2.44 (m, 1H, CH$_2$OCH), 2.04 (qd, 4H, CH$_2$CH$_2$CHCH), 1.58-1.19 (m, 14H, CH$_2$), 0.87 (t, 3H, CH$_3$).

Step 4. Synthesis of OF-02

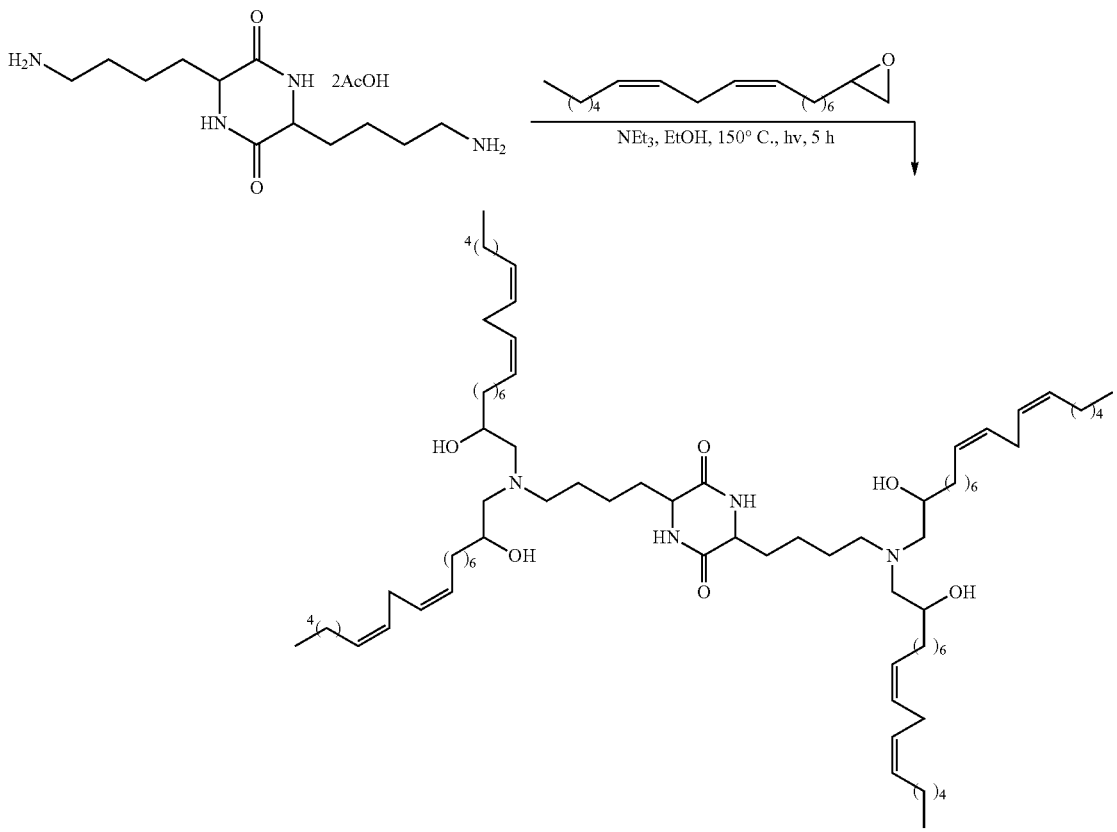

To a solution of EA-02 (357 mg, 1.35 mmol, 6 eq) in ethanol (2 ml) was added diketopiperazine 1 (84.7 mg, 0.225 mmol, 1 eq) followed by triethylamine (125 µl, 0.9 mmol, 4 eq). See, e.g., Y. Dong et al., Proc Natl Acad Sci USA 2014, 111, 3955-3960. The mixture was stirred at room temperature for 7 minutes before being irradiated, with stirring, in a microwave for 5 hours at 150° C. The crude product was purified by flash chromatography to yield the product as a yellow oil (33% yield).

$^1$H NMR (500 MHz, DMSO-$d_6$, 20° C.) 8.11 (br, 2H, CONH), 5.15-5.2 (m, 16H, $CH_2CH$), 4.21 (dd, 4H, OH), 3.79 (br, 2H, COCH), 3.44 (br, 4H, CHOH), 2.7 (m, 8H, $CHCH_2CH$), 2.25-2.44 (m, 12H, $NCH_2$), 2.1 (m, 16H, $CHCH_2CH_2$), 1.64-1.67 (m, 4H, $CH_2$), 1.21-1.39 (m, 72H, $CH_2$), 0.88 (t, 12H, $CH_3$). HRMS (DART) (m/z): calc'd for $C_{84}H_{152}N_4O_6$ [M+H]*: 1314.17. found: 1314.93.

Example 4

Synthesis of OF-03

Step 1. Synthesis of EA-03-aldehyde

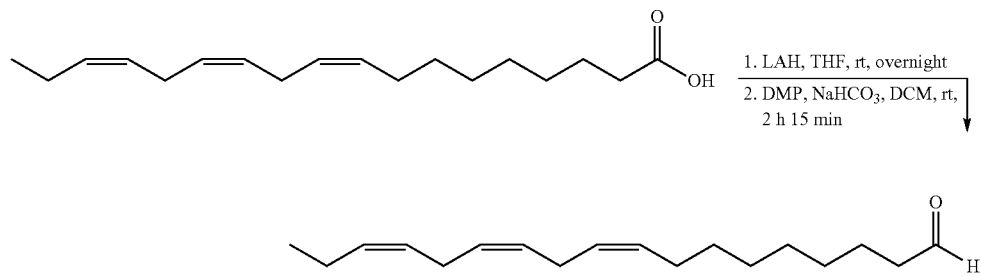 [SMILES: CC/C=C\C/C=C\C/C=C\CCCCCCCC(=O)O ; CC/C=C\C/C=C\C/C=C\CCCCCCCC=O]

To a solution of linolenic acid (4.57 ml, 15 mmol, 1 eq) in THF (190 ml) at 0° C. was added Lithium Aluminum Hydride (1 M in THF, 22.5 ml, 22.5 mmol, 1.5 eq) dropwise. The solution was allowed to warm to room temperature and was stirred overnight. The reaction was quenched with sequential additions of water (0.85 ml), 1N NaOH (0.85 ml), and water (2.6 ml) dropwise. The mixture was filtered through celite, and the filtrate was concentrated under reduced pressure. The crude product was then dissolved in $CH_2Cl_2$ (160 ml). $NaHCO_3$ (8.821 g, 105 mmol, 7 eq) was added followed by Dess-Martin-Periodinane (7.63 g, 18 mmol, 1.2 eq). The mixture was stirred for 2 hours, 15 minutes. It was then diluted in petroleum ether, washed sequentially with saturated $NaHCO_3$ and brine, dried over anhydrous sodium sulfate, filtered, and concentrated under reduced pressure. The crude product EA-03-aldehyde, a yellow oil, was used without further purification.

Step 2. Synthesis of EA-03-chloroalcohol

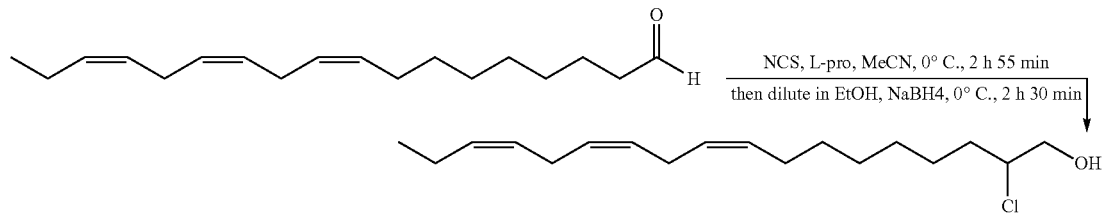

To a solution of EA-03-aldehyde (5.131, 1 eq) in MeCN (14 ml) cooled to 0° C. was added L-proline (177 mg, 1.54 mmol, 0.3 eq) and N-chlorosuccinimide (650 mg, 4.87 mmol, 0.95 eq). The solution was stirred at 0° C. for 2 hours 55 minutes. It was then diluted in ethanol (8 ml) and to it was added NaBH4 (484 mg, 12.8 mmol, 2.5 eq). The solution was stirred at 0° C. for 2 hours, 30 minutes. It was then diluted in ethyl acetate, washed with brine, dried over anhydrous sodium sulfate, filtered, and concentrated under reduced pressure. The crude product EA-03-chloroalcohol, a yellow oil, was used without further purification.

Step 3. Synthesis of EA-03

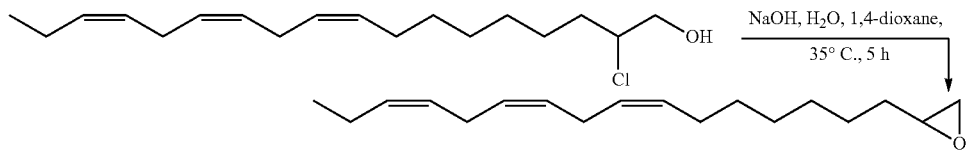

To a solution of EA-03-chloroalcohol (5.13 mmol, 1 eq) in 1,4-dioxane (15.5 ml) was added a solution of NaOH (4.617 g, 115.4 mmol, 22.5 eq) in $H_2O$ (20 ml). The reaction mixture was heated to 35° C. and allowed to stir for 5 hours. The resulting mixture was then diluted in hexanes, washed with brine, dried over anhydrous sodium sulfate, filtered, and concentrated under reduced pressure. The crude product was purified by flash chromatography on silica gel using acetone/hexanes (0:100→10:90) to yield EA-03 as a pale yellow oil (9% yield over 4 steps).

$^1$H NMR (500 MHz, CDCl$_3$, 20° C.): 5.33 (m, 6H, CH), 2.88 (tdd, 1H, CH$_2$OCH), 2.80 (m, 5H, CHCH$_2$CH), 2.73 (m, 1H, CH$_2$OCH), 2.44 (m, 1H CH$_2$OCH), 2.04 (m, 4H, CH$_2$CH$_2$CH), 1.58-1.19 (m, 10H, CH$_2$), 0.87 (t, 3H, CH$_3$).

Step 4. Synthesis of OF-03

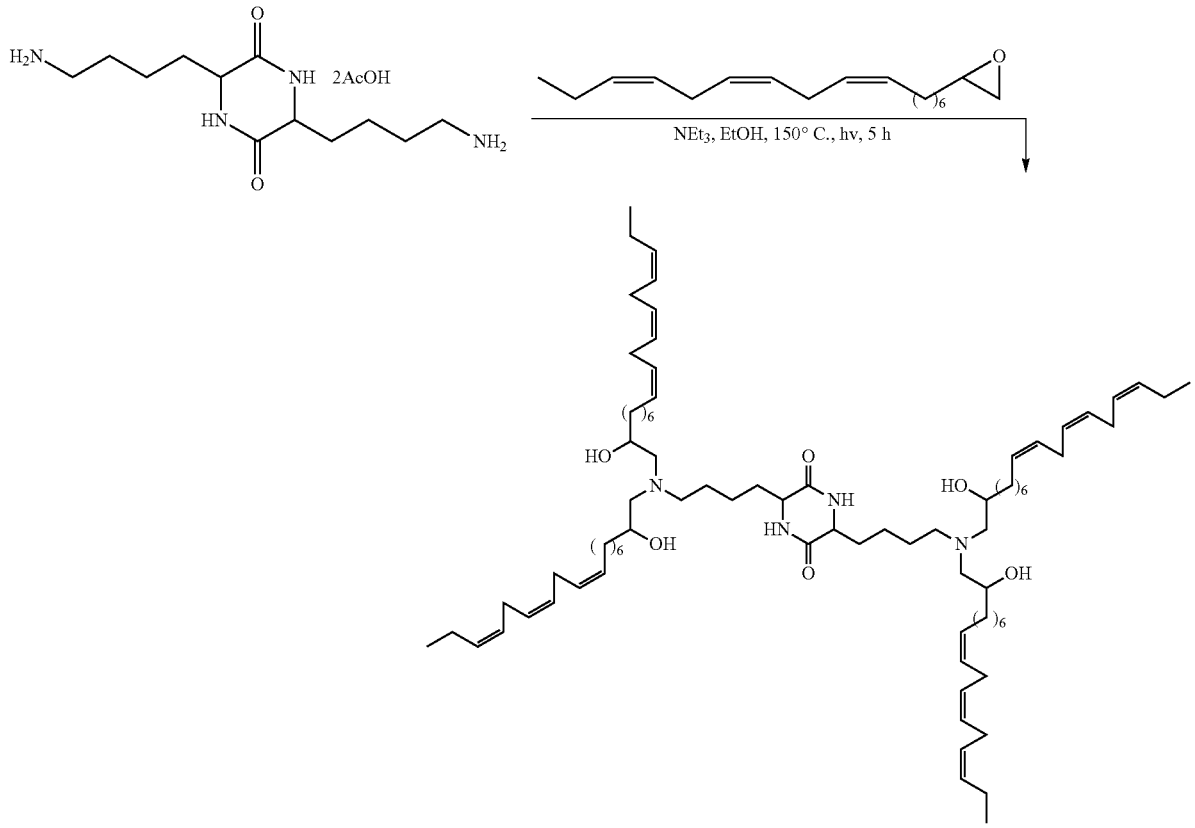

To a solution of EA-03 (357 mg, 1.35 mmol, 6 eq) in ethanol (2 ml) was added diketopiperazine 1 (84.7 mg, 0.225 mmol, 1 eq) followed by triethylamine (125 µl, 0.9 mmol, 4 eq). See, e.g., Y. Dong et al., Proc Natl Acad Sci USA 2014, 111, 3955-3960. The mixture was stirred at room temperature for 10 minutes before being irradiated, with stirring, in a microwave for 5 hours at 150° C. The crude product was purified by flash chromatography to yield the product, as a mix of the desired product and the tri-substituted product, as a yellow oil (6% yield).

$^1$H NMR (500 MHz, DMSO-$d_6$, 20° C.) 8.11 (br, 2H, CONH), 5.15-5.2 (m, 24H, CH$_2$CH), 4.21 (dd, 4H, OH), 3.79 (br, 2H, COCH), 3.44 (br, 4H, CHOH), 2.7 (m, 16H, CHCH$_2$CH), 2.25-2.44 (m, 12H, NCH$_2$), 2.1 (m, 16H, CHCH$_2$CH$_2$), 1.64-1.67 (m, 4H, CH$_2$), 1.21-1.39 (m, 48H, CH$_2$), 0.88 (t, 12H, CH$_3$). HRMS (DART) (m/z): calc'd for C$_{84}$H$_{144}$N$_4$O$_6$ [M+H]*: 1306.11. found: 1306.87.

Additional References

See also Fenton et al., *Advanced Materials* (2016) 28:2939-2943, and references cited therein, each of which is incorporated herein by reference.

OTHER EMBODIMENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, books, manuals, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

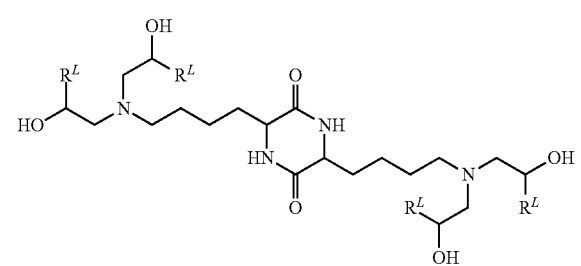

and salts thereof, wherein each instance of $R^L$ is independently optionally substituted $C_6$-$C_{40}$ alkenyl; and each instance of $R^L$ comprises only cis double bonds.

2. The compound of claim 1, wherein at least one instance of $R^L$ is a group of formula:

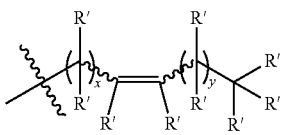

wherein:
x is an integer between 4 and 20, inclusive;
y is an integer between 1 and 20, inclusive; and
each instance of R' is independently hydrogen, optionally substituted $C_{1-6}$alkyl, halogen, substituted hydroxyl, substituted thiol, and substituted amino;

provided the group comprises no more than 40 linear carbon atoms.

3. The compound of claim 2, wherein x is 4, 5, 6, 7, or 8.

4. The compound of claim 1, wherein at least one instance of $R^L$ is a group of formula:

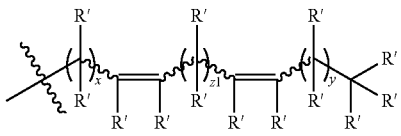

wherein:
x is an integer between 4 and 20, inclusive;
y is an integer between 1 and 20, inclusive;
z1 is 1, 2, or 3; and
each instance of R' is independently hydrogen, optionally substituted $C_{1-6}$alkyl, halogen, substituted hydroxyl, substituted thiol, and substituted amino;
provided the group comprises no more than 40 linear carbon atoms.

5. The compound of claim 1, wherein at least one instance of $R^L$ is a group of formula:

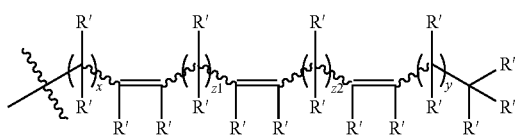

wherein:
x is an integer between 4 and 20, inclusive;
y is an integer between 1 and 20, inclusive;
each instance of z1 and z2 is independently 1, 2, or 3; and
each instance of R' is independently hydrogen, optionally substituted $C_{1-6}$alkyl, halogen, substituted hydroxyl, substituted thiol, and substituted amino;
provided the group comprises no more than 40 linear carbon atoms.

6. The compound of claim 1, wherein at least one instance of $R^L$ is:

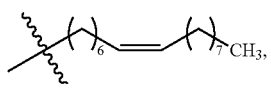

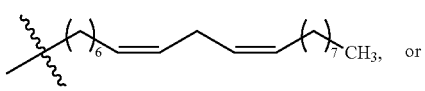 or

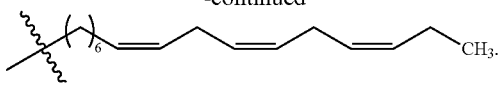

7. A composition comprising:
a compound of claim 1, or a salt thereof;
an agent; and
optionally, an excipient.

8. The composition of claim 7, wherein the composition further comprises cholesterol, a PEGylated lipid, a phospholipid, or an apolipoprotein.

9. The composition of claim 7, wherein the agent is an organic molecule, inorganic molecule, nucleic acid, protein, peptide, polynucleotide, targeting agent, an isotopically labeled chemical compound, vaccine, an immunological agent, or an agent useful in bioprocessing.

10. The composition of claim 9, wherein the agent is a polynucleotide, and the polynucleotide is an RNA.

11. The composition of claim 10, wherein the agent is messenger RNA, single-stranded RNA, double-stranded RNA, small interfering RNA, precursor messenger RNA, small hairpin RNA, microRNA, guide RNA, transfer RNA, antisense RNA, heterogeneous nuclear RNA, coding RNA, non-coding RNA, long non-coding RNA, satellite RNA, viral satellite RNA, signal recognition particle RNA, small cytoplasmic RNA, small nuclear RNA, ribosomal RNA, Piwi-interacting RNA, polyinosinic acid, ribozyme, flexizyme, small nucleolar RNA, spliced leader RNA, viral RNA, or viral satellite RNA.

12. The composition of claim 11, wherein the agent is messenger RNA.

13. The composition of claim 12, wherein the agent is a polynucleotide and the polynucleotide is DNA.

14. The composition of claim 13, wherein the DNA is plasmid DNA.

15. A method of delivering an agent to a subject or cell, the method comprising administering to the subject or contacting the cell with a composition of claim 7.

16. A method of treating or preventing a disease in a subject in need thereof, the method comprising administering to the subject with a composition of claim 7.

17. The method of claim 16, wherein the disease is a genetic disease, proliferative disease, hematological disease, neurological disease, liver disease, spleen disease, lung disease, painful condition, psychiatric disorder, musculoskeletal disease, a metabolic disorder, inflammatory disease, or autoimmune disease.

18. The composition or method of claim 17, wherein the hematological disease is anemia, and the agent is erythropoietin.

19. The method of claim 16, wherein the disease is hepatic carcinoma, hypercholesterolemia, refractory anemia, familial amyloid neuropathy, or hemophelia.

20. The method of claim 16, wherein the disease is a hematological disease.

21. A kit comprising:
a composition of claim 7; and
instructions for using the kit.

22. The composition of claim 7, wherein the composition is in the form of a particle.

23. The composition of claim 22, wherein the particle is a nanoparticle or microparticle.

24. The compound of claim 1 of the formula:
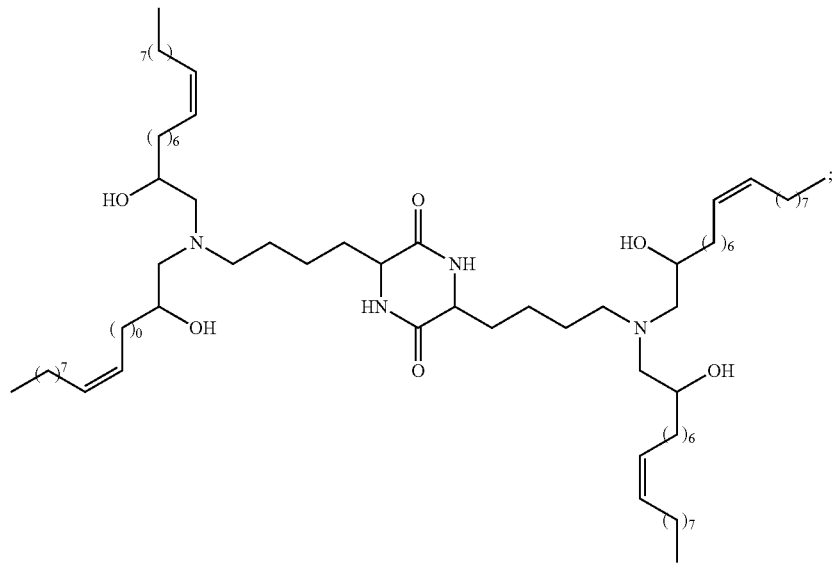
OF-00
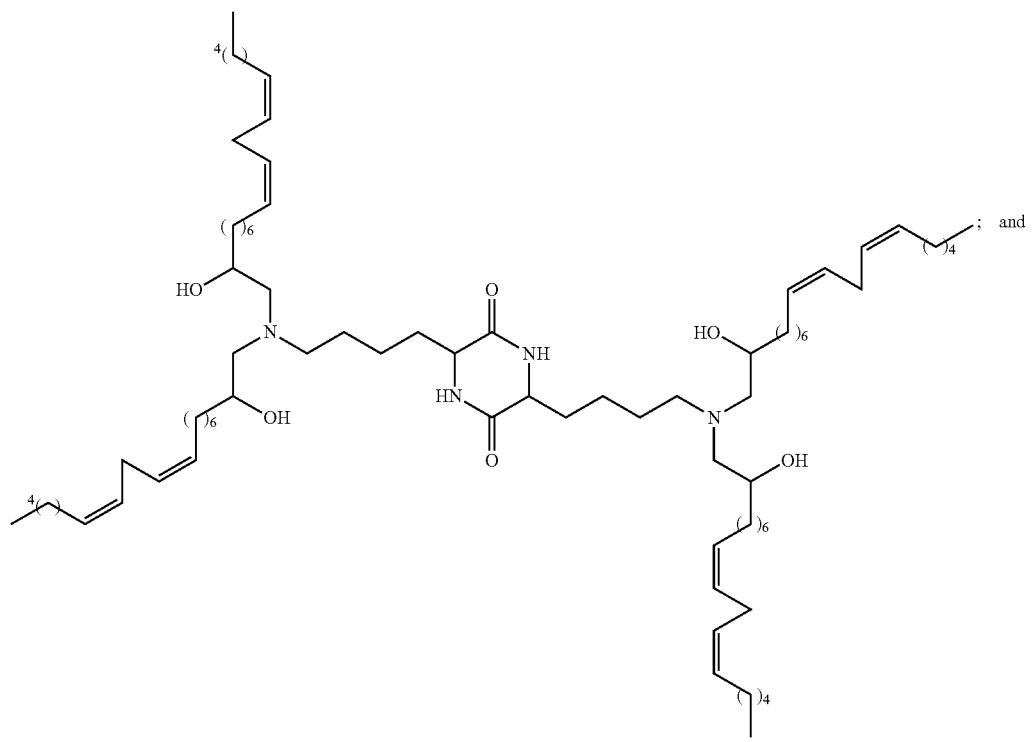
OF-02

OF-03

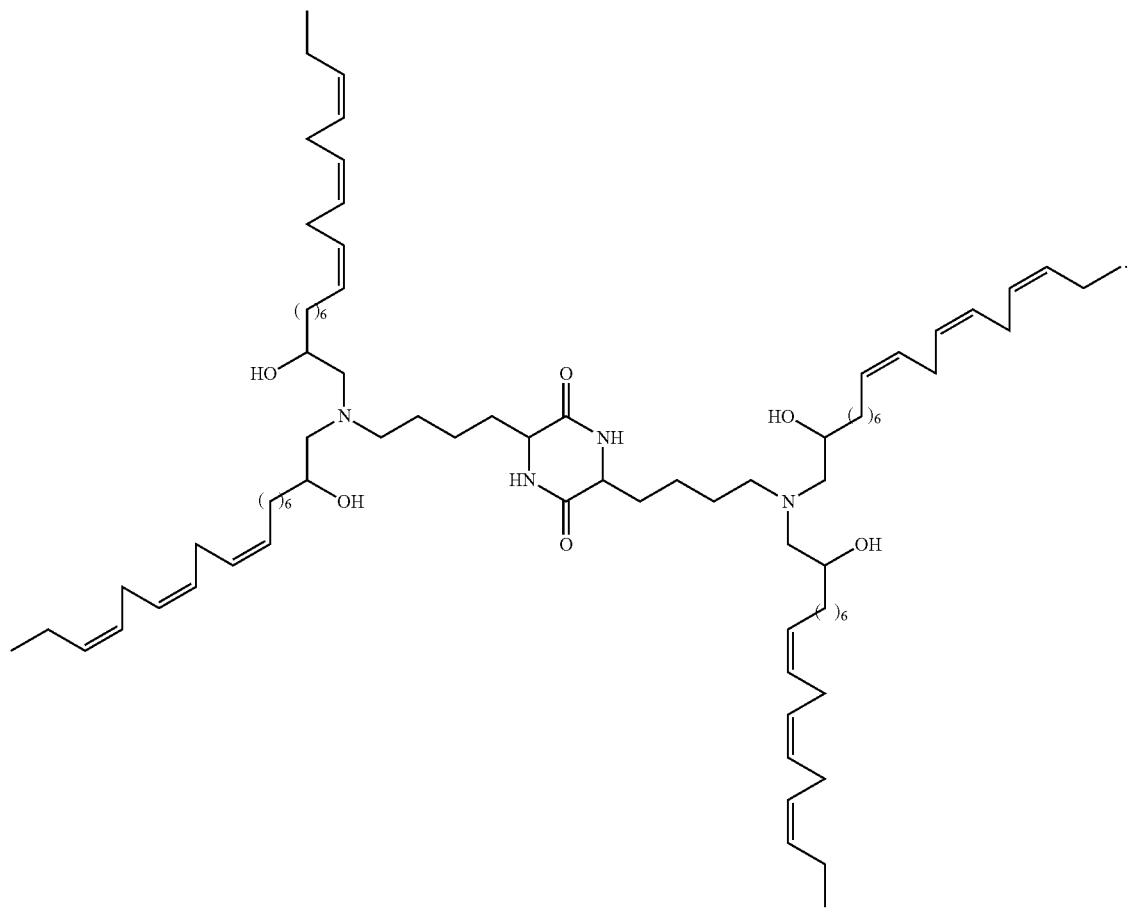

25. A method of preparing a compound of Formula (I), the method comprising reacting the compound:

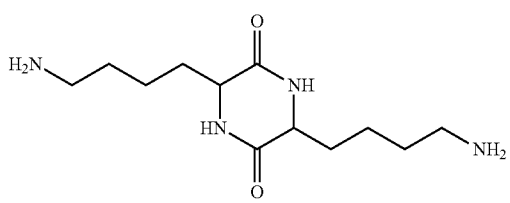 [SMILES: NCCCCC1NC(=O)C(CCCCN)NC1=O]

or salt thereof, with an epoxide of formula:

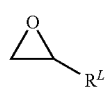

to provide a compound of Formula (I):

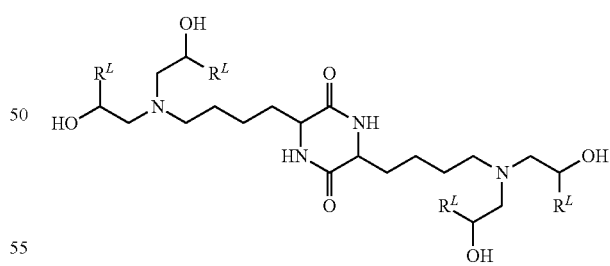

(I)

or salt thereof, wherein each instance of $R^L$ is independently optionally substituted $C_6$-$C_{40}$ alkenyl; and each instance of $R^L$ comprises only cis double bonds.

26. A method of preparing an epoxide of formula:

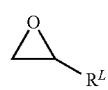

wherein each instance of $R^L$ is independently optionally substituted $C_6$-$C_{40}$ alkenyl; and each instance of $R^L$ comprises only cis double bonds;
the method comprising:
(i) reducing a carboxylic acid of formula:

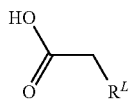

to an aldehyde of formula:

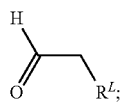

(ii) treating the aldehyde under alpha chlorinating conditions to provide a chlorinated aldehyde of formula:

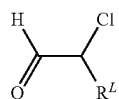

(iii) reducing the chlorinated aldehyde to provide an alcohol of formula:

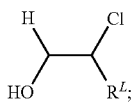

and (iv) treating the alcohol under suitable conditions to provide the epoxide.

* * * * *